（12) United States Patent  
Bell et al.

(10) Patent No.: US 8,367,830 B2  
(45) Date of Patent: Feb. 5, 2013

(54) METHODS FOR THE IDENTIFICATION OF PHOSPHATIDYLINOSITOL KINASE INTERACTING MOLECULES AND FOR THE PURIFICATION OF PHOSPHATIDYLINOSITOL KINASE PROTEINS

(75) Inventors: Kathryn Bell, London (GB); Nigel Ramsden, Royston (GB); Giovanna Bergamini Moore, Heidelberg (DE); Gitte Neubauer, Mannheim (DE)

(73) Assignee: Cellzome AG, Heidelberg (DE)

( * ) Notice: Subject to any disclaimer, the term of this patent is extended or adjusted under 35 U.S.C. 154(b) by 0 days.

(21) Appl. No.: 13/321,122

(22) PCT Filed: May 14, 2010

(86) PCT No.: PCT/EP2010/002987  
§ 371 (c)(1),  
(2), (4) Date: Feb. 9, 2012

(87) PCT Pub. No.: WO2010/133318  
PCT Pub. Date: Nov. 25, 2010

(65) Prior Publication Data  
US 2012/0135421 A1 May 31, 2012

(30) Foreign Application Priority Data

May 20, 2009 (EP) .................................. 09006786

(51) Int. Cl.  
*C07D 471/04* (2006.01)  
*C08B 37/00* (2006.01)  
*G01N 33/573* (2006.01)

(52) U.S. Cl. ............................. 546/119; 435/7.4; 536/53

(58) Field of Classification Search .................. 546/119; 435/7.4; 536/53  
See application file for complete search history.

(56) References Cited

FOREIGN PATENT DOCUMENTS

| WO | WO 2006/134056 | 12/2006 |
| WO | WO 2007/095588 | 8/2007 |
| WO | WO 2008/015013 | 2/2008 |
| WO | WO 2008/025821 | 3/2008 |
| WO | WO 2009/010530 | 1/2009 |

OTHER PUBLICATIONS

Anieto and Gruenberg, "Chapter 4.3 Subcellular Fractionation of Tissue Culture Cells," in *Current Protocols in Protein Science*, Editors: John.E. Coligan, Ben M. Dunn, Hidde L. Ploegh, David W. Speicher, Paul T. Wingfield; John Wiley & Sons, Inc., ISBN: 0-471-14098-8 (2003).  
Ausubel et al., "Chapter 11 Immunology," pp. 11-1 to 11-29 in: *Short Protocols in Molecular Biology.* Fiftth Edition, John Wiley & Sons, Inc., New York, (2002).

Bader et al., "Oncogenic PI3K Deregulates Transcription and Translation," *Nat. Rev. Cancer* 5:921-929 (2005).  
Bain et al., "The Selectivity of Protein Kinase Inhibitors: A Further Update," *Biochem. J.* 408:297-315 (2007).  
Balla and Balla, "Phosphatidylinositol 4-Kinases: Old Enzymes with Emerging Functions," *TRENDS in Cell Biology* 16:351-361 (2006).  
Bantscheff et al., "Quantitative Chemical Proteomics Reveals Mechanisms of Action of Clinical ABL Kinase Inhibitors," *Nat Biotechnol.* 25:1035-1044 (2007).  
Biddison, W.E., "Chapter 2.2 Preparation and Culture of Human Lymphocytes," pp. 2.2.1-2.213 in *Current Protocols in Cell Biology*, John Wiley & Sons, Inc. (1998).  
Breinbauer et al., "Natural Product Guided Compound Library Development," *Curr Med Chem.* 9:2129-2145 (2002).  
Carpenter et al., "Purification and Characterization of Phosphoinositide 3-Kinase from Rat Liver," *J Biol Chem.* 265:19704-19711 (1990).  
Castle, "Chapter 4.2: Purification of Organelles from Mammalian Cells" pp. 4.2.1-4.2.57 in *Current Protocols in Protein Science* John Wiley & Sons, Inc., (2004).  
Deora et al., "A Redox-Triggered Ras-Effector Interaction. Recruitment of Phosphatidylinositol 3'-Kinase to Ras by Redox Stress," *J Biol Chem.* 273:29923-29928 (1998).  
Elias and Gygi, "Target-Decoy Search Strategy for Increased Confidence in Large-Scaled Protein Identifications by Mass Spectrometry," *Nat. Methods* 4:207-214 (2007).  
Fenteany et al., "Inhibition of Proteasome Activities and Subunit-Specific Amino-Terminal Threonine Modification by Lactacystin," *Science* 268:726-731 (1995).  
Fruman et al., "Phosphoinositide Kinases," *Annu Rev Biochem.* 67:481-507 (1998).  
Fuchikami et al., "A Versatile High-Throughput Screen for Inhibitors of Lipid Kinase Activity: Development of an Immobilized Phospholipid Plate Assay for Phosphoinositide 3-Kinase γ," *J. Biomol. Screening* 7:441-450 (2002).  
Garcia-Martinez et al., "Ku-0063794 is a Specific Inhibitor of the Mammalian Target of Rapamycin (mTOR)," *Biochem. J.* 421 :29-42 (2009).  
Gharbi et al., "Exploring the Specificity of the PI3K Family Inhibitor LY294002," *Biochem J.* 404:15-21 (2007).

(Continued)

*Primary Examiner* — Niloofar Rahmani  
(74) *Attorney, Agent, or Firm* — Kristina Bieker-Brady; Clark & Elbing LLP

(57) ABSTRACT

The present invention relates to immobilization compounds of formula (I), immobilization products and preparations thereof as well as methods and uses for the identification of phosphatidylinositol kinase interacting compounds or for the purification or identification of phosphatidylinositol kinase proteins.

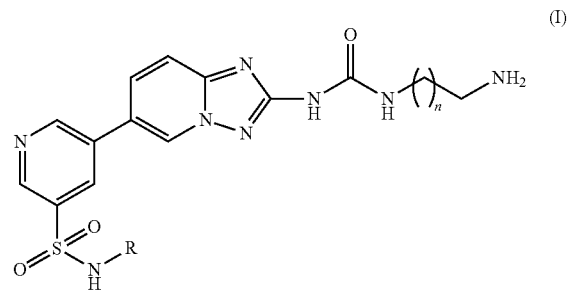

(I)

14 Claims, 17 Drawing Sheets

OTHER PUBLICATIONS

Figure 1:
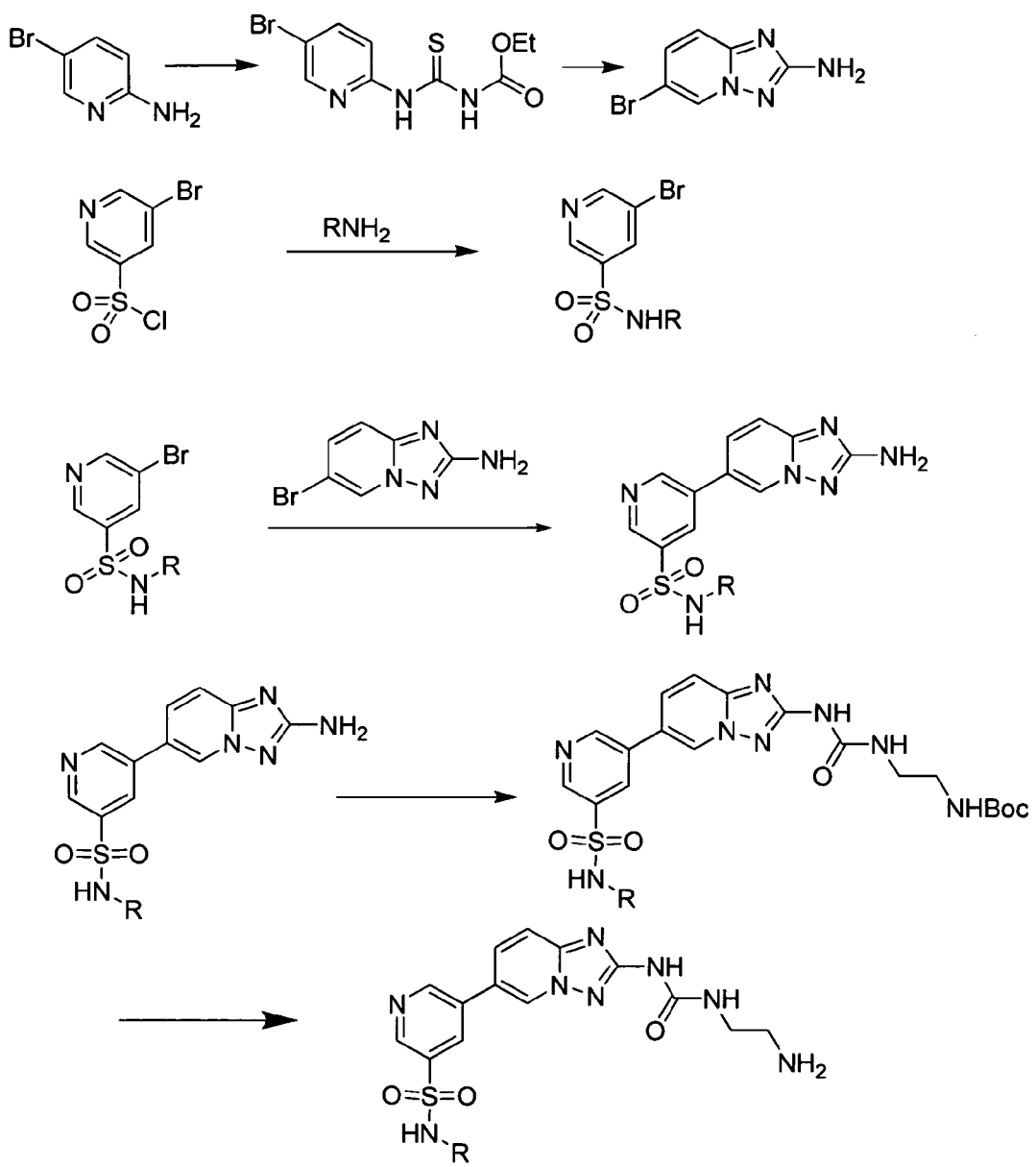

Glickman et al., "A Comparison of ALPHAScreen, TR-FRET, and TRF as Assay Methods for FXR Nuclear Receptors," *J. Biomol Screen* 7:3-10 (2002).

Karaman et al., "A Quantitative Analysis of Kinase Inhibitor Selectivity," *Nat Biotechnol.* 26:127-32 (2008).

Karwa and Mitra 'Techniques for the Extraction, Isolation, and Purification of Nucleic Acids'; Chapter 8 in "Sample Preparation Techniques in Analytical Chemistry," *Chemical Analysis* 162:331-375 (2003).

Kashem et al., "Three Mechanistically Distinct Kinase Assays Compared: Measurement of Intrinsic ATPase Activity Identified the Most Comprehensive Set of ITK Inhibitors," *J. Biomol. Screening* 12:70-83 (2007).

Kersey et al., "Technical Brief: The International Protein Index: An Integrated Database for Proteomics Experiments," *Proteomics* 4:1985-1988 (2004).

Lingaraj et al., "A High-Throughput Liposome Substrate Assay with Automated Lipid Extraction Process for PI 3-Kinase," *J. Biolmol. Screen.* 13:906-911 (2008).

Mann et al., "Analysis of Proteins and Proteomes by Mass Spectrometry," *Ann. Rev. Biochem.* 70:437-473 (2001).

Moger et al., "The Application of Fluorescense Lifetime Readouts in High-Throughput Screening," *J. Biomol. Screening* 11: 765-772 (2006).

Patricelli et al., "Functional Interrogation of the Kinome Using Nucleotide Acyl Phosphates," *Biochemistry*. 46:350-358 (2007).

Perkins et al., "Probability-Based Protein Identification by Searching Sequence Databases Using Mass Spectrometry Data," *Electrophoresis* 20:3551-3567 (1999).

Petty, "Overview of the Physical State of Proteins Chapter 1", Unit 5.1.1-5.1.10 in *Current Protocols in Cell Biology* John Wiley & Sons, Inc., (1998).

Pomel et al., "Furan-2-ylmethylene Thiazolidinediones as Novel, Potent, and Selective Inhibitors of Phosphoinositide 3-Kinase Gamma," *J. Med. Chem.* 49:3857-3871 (2006).

Ross et al., "Multiplexed Protein Quantitation in *Saccharomyces cerevisae* Using Amine-Reactive Isobaric Tagging Reagents," *Mol. Cell. Proteomics* 3:1154-1169 (2004).

Sasaki et al., "Colorectal carcinomas in mice lacking the catalytic subunit of PI(3)Kgamma," *Nature*. 406:897-902 (2000).

Shevchenko et al., "Mass spectrometric sequencing of proteins silver-stained polyacrylamide gels," *Anal Chem*. 68:850-858 (1996).

Subramanian, "Immunoaffinity Chromatography," *Molecular Biotechnology* 20:41-47 (2002).

Tolias et al., "Type I Phosphatidylinositol-4-Phosphate 5-Kinases Synthesize the Novel Lipids Phosphatidylinositol 3, 5-Bisphosphate and Phosphatidylinositol 5-Phosphate," *J. Biol. Chem.* 273:18040-18046 (1998).

Vedvik et al., "Overcoming Compound Interference in Fluorescence Polarization-Based Kinase Assays Using Far-Red Tracers," *Assay Drug Dev. Technol.* 2: 193-203 (2004).

Weernink et al., "Regulation and Cellular Roles of Phosphoinositide 5-Kinases," *Eur. J. Pharmacol.* 500:87-99 (2004).

Wingfield, Paul T., "Production of Recombinant Proteins," Chapter 5, Unit 5.0.1-5.0.3 in: *Current Protocols in Protein Science*, Editors: John. E. Coligan, Ben M. Dunn, Hidde L. Ploegh, David W. Speicher, Paul T. Wingfield; John Wiley & Sons Inc., ISBN: 0-471-14098-8 (2002).

Wu et al., "Comparative Study of Three Proteomic Quantitative Methods, DIGE, cICAT, and iTRAQ, Using 2D Gel- or LC-MALDI TOF/TOF," *J. Proteome Res.* 5:651-658 (2006).

Wymann and Schneiter, "Lipid Signalling in Disease," *Nat. Rev. Mol. Cell. Bio.* 9:162-176 (2008).

Zaman et al., "Fluorescence Assays for High-Throughput Screening of Protein Kinases," *Comb. Chem. High Throughput Screen* 6: 313-320 (2003).

Zaman et al., "Enzyme Fragment Complementation Binding Assay for P38α Mitogen-Activated Protein Kinase to Study the Binding Kinetics of Enzyme Inhibitors," *Assay Drug Dev. Technol.* 4:411-420 (2006).

Zhang et al., "Time-Resolved Forster Resonance Energy Transfer Assays for the Binding of Nucleotide and Protein Substrates to P38α Protein Kinase," *Analytical Biochemistry* 343:76-83 (2005).

International Preliminary Report on Patentability for International Application No. PCT/EP2010/002987, issued Nov. 22, 2011.

International Search Report for International Application No. PCT/EP2010/002987, completed Aug. 13, 2010, mailed Aug. 20, 2010.

Figure 11

MPPRPSSGEL WGIHLMPPRI LVECLLPNGM IVTLECLREA TLITIKHELF
KEARKYPLHQ LLQDESSYIF VSVTQEAERE EFFDETRRLC DLRLFQPFLK
VIEPVGNREE KILNREIGFA IGMPVCEFDM VKDPEVQDFR RNILNVCKEA
VDLRDLNSPH SRAMYVYPPN VESSPELPKH IYNKLDKGQI IVVIWVIVSP
NNDKQKYTLK INHDCVPEQV IAEAIRKKTR SMLLSSEQLK LCVLEYQGKY
ILKVCGCDEY FLEKYPLSQY KYIRSCIMLG RMPNLMLAK ESLYSQLPMD
CFTMPSYSRR ISTATPYMNG ETSTKSLWVI NSALRIKILC ATYVNVNIRD
IDKIYVRTGI YHGGEPLCDN VNTQRVPCSN PRWNEWLNYD IYIPDLPRAA
RLCLSICSVK GRKGAKEEHC PLAWGNINLF DYTDTLVSGK MALNLWPVPH
GLEDLLNPIG VTGSNPNKET PCLELEFDWF SSVVKFPDMS VIEEHANWSV
SREAGFSYSH AGLSNRLARD NELRENDKEQ LKAISTRDPL SEITEQEKDF
LWSHRHYCVT IPEILPKLLL SVKWNSRDEV AQMYCLVKDW PPIKPEQAME
LLDCNYPDPM VRGFAVRCLE KYLTDDKLSQ YLIQLVQVLK YEQYLDNLLV
RFLLKKALTN QRIGHFFFWH LKSEMHNKTV SQRFGLLLES YCRACGMYLK
HLNRQVEAME KLINLTDILK QEKKDETQKV QMKFLVEQMR RPDFMDALQG
FLSPLNPAHQ LGNLRLEECR IMSSAKRPLW LNWENPDIMS ELLFQNNEII
FKNGDDLRQD MLTLQIIRIM ENIWQNQGLD LRMLPYGCLS IGDCVGLIEV
VRNSHTIMQI QCKGGLKGAL QFNSHTLHQW LKDKNKGEIY DAAIDLFTRS
CAGYCVATFI LGIGDRHNSN IMVKDDGQLF HIDFGHFLDH KKKKFGYKRE
RVPFVLTQDF LIVISKGAQE CTKTREFERF QEMCYKAYLA IRQHANLFIN
LFSMMLGSGM PELQSFDDIA YIRKTLALDK TEQEALEYFM KQMNDAHHGG
WTTKMDWIFH TIKQHALN

Figure 12

```
MCFSFIMPPA MADILDIWAV DSQIASDGSI PVDFLLPTGI YIQLEVPREA
TISYIKQMLW KQVHNYPMFN LLMDIDSYMF ACVNQTAVYE ELEDETRRLC
DVRPFLPVLK LVTRSCDPGE KLDSKIGVLI GKGLHEFDSL KDPEVNEFRR
KMRKFSEEKI LSLVGLSWMD WLKQTYPPEH EPSIPENLED KLYGGKLIVA
VHFENCQDVF SFQVSPNMNP IKVNELAIQK RLTIHGKEDE VSPYDYVLQV
SGRVEYVFGD HPLIQFQYIR NCVMNRALPH FILVECCKIK KMYEQEMIAI
EAAINRNSSN LPLPLPPKKT RIISHVWENN NPFQIVLVKG NKLNTEETVK
VHVRAGLFHG TELLCKTIVS SEVSGKNDHI WNEPLEFDIN ICDLPRMARL
CFAVYAVLDK VKTKKSTKTI NPSKYQTIRK AGKVHYPVAW VNTMVFDFKG
QLRTGDIILH SWSSFPDELE EMLNPMGTVQ TNPYTENATA LHVKFPENKK
QPYYYPPFDK IIEKAAEIAS SDSANVSSRG GKKFLPVLKE ILDRDPLSQL
CENEMDLIWT LRQDCREIFP QSLPKLLLSI KWNKLEDVAQ LQALLQIWPK
LPPREALELL DFNYPDQYVR EYAVGCLRQM SDEELSQYLL QLVQVLKYEP
FLDCALSRFL LERALGNRRI GQFLFWHLRS EVHIPAVSVQ FGVILEAYCR
GSVGHMKVLS KQVEALNKLK TLNSLIKLNA VKLNRAKGKE AMHTCLKQSA
YREALSDLQS PLNPCVILSE LYVEKCKYMD SKMKPLWLVY NNKVFGEDSV
GVIFKNGDDL RQDMLTLQML RLMDLLWKEA GLDLRMLPYG CLATGDRSGL
IEVVSTSETI ADIQLNSSNV AAAAAFNKDA LLNWLKEYNS GDDLDRAIEE
FTLSCAGYCV ASYVLGIGDR HSDNIMVKKT GQLFHIDFGH ILGNFKSKFG
IKRERVPFIL TYDFIHVIQQ GKTGNTEKFG RFRQCCEDAY LILRRHGNLF
ITLFALMLTA GLPELTSVKD IQYLKDSLAL GKSEEEALKQ FKQKFDEALR
ESWTTKVNWM AHTVRKDYRS
```

Figure 13

```
MCPVDFHGIF QLDERRRDAV IALGIFLIES DLQHKDCVVP YLLRLLKGLP
KVYWVEESTA RKGRGALPVA ESFSFCLVTL LSDVAYRDPS LRDEILEVLL
QVLHVLLGMC QALEIQDKEY LCKYAIPCLI GISRAFGRYS NMEESLLSKL
FPKIPPHSLR VLEELEGVRR RSFNDFRSIL PSNLLTVCQE GTLKRKTSSV
SSISQVSPER GMPPPSSPGG SAFHYFEASC LPDGTALEPE YYFSTISSSF
SVSPLFNGVT YKEFNIPLEM LRELLNLVKK IVEEAVLKSL DAIVASVMEA
NPSADLYYTS FSDPLYLTMF KMLRDTLYYM KDLPTSFVKE IHDFVLEQFN
TSQGELQKIL HDADRIHNEL SPLKLRCQAS AACVDLMVWA VKDEQGAENL
CIKLSEKLQS KTSSKVIIAH LPLLICCLQG LGRLCERFPV VVHSVTPSLR
DFLVIPSPVL VKLYKYHSQY HTVAGNDIKI SVTNEHSEST LNVMSGKKSQ
PSMYEQLRDI AIDNICRCLK AGLTVDPVIV EAFLASLSNR LYISQESDKD
AHLIPDHTIR ALGHIAVALR DTPKVMEPIL QILQQKFCQP PSPLDVLIID
QLGCLVITGN QYIYQEVWNL FQQISVKASS VVYSATKDYK DHGYRHCSLA
VINALANIAA NIQDEHLVDE LLMNLLELFV QLGLEGKRAS ERASEKGPAL
KASSSAGNLG VLIPVIAVLT RRLPPIKEAK PRLQKLFRDF WLYSVLMGFA
VEGSGLWPEE WYEGVCEIAT KSPLLTFPSK EPLRSVLQYN SAMKNDTVTP
AELSELRSTI INLLDPPPEV SALINKLDFA MSTYLLSVYR LEYMRVLRST
DPDRFQVMFC YFEDKAIQKD KSGMMQCVIA VADKVFDAFL NMMADKAKTK
ENEEELERHA QFLLVNFNHI HKRIRRVADK YLSGLVDKFP HLLWSGTVLK
TMLDILQTLS LSLSADIHKD QPYYDIPDAP YRITVPDTYE ARESIVKDFA
ARCGMILQEA MKWAPTVTKS HLQEYLNKHQ NWVSGLSQHT GLAMATESIL
HFAGYNKQNT TLGATQLSER PACVKKDYSN FMASLNLRNR YAGEVYGMIR
FSGTTGQMSD LNKMMVQDLH SALDRSHPQH YTQAMFKLTA MLISSKDCDP
QLLHHLCWGP LRMFNEHGME TALACWEWLL AGKDGVEVPF MREMAGAWHM
TVEQKFGLFS AEIKEADPLA ASEASQPKPC PPEVTPHYIW IDFLVQRFEI
AKYCSSDQVE IFSSLLQRSM SLNIGGAKGS MNRHVAAIGP RFKLLTLGLS
LLHADVVPNA TIRNVLREKI YSTAFDYFSC PPKFPTQGEK RLREDISIMI
KFWTAMFSDK KYLTASQLVP PDNQDTRSNL DITVGSRQQA TQGWINTYPL
SSGMSTISKK SGMSKKTNRG SQLHKYYMKR RTLLLSLLAT EIERLITWYN
PLSAPELELD QAGENSVANW RSKYISLSEK QWKDNVNLAW SISPYLAVQL
PARFKNTEAI GNEVTRLVRL DPGAVSDVPE AIKFLVTWHT IDADAPELSH
VLCWAPTDPP TGLSYFSSMY PPHPLTAQYG VKVLRSFPPD AILFYIPQIV
QALRYDKMGY VREYILWAAS KSQLLAHQFI WNMKTNIYLD EEGHQKDPDI
```

Figure 13 - continued

GDLLDQLVEE ITGSLSGPAK DFYQREFDFF NKITNVSAII KPYPKGDERK
KACLSALSEV KVQPGCYLPS NPEAIVLDID YKSGTPMQSA AKAPYLAKFK
VKRCGVSELE KEGLRCRSDS EDECSTQEAD GQKISWQAAI FKVGDDCRQD
MLALQIIDLF KNIFQLVGLD LFVFPYRVVA TAPGCGVIEC IPDCTSRDQL
GRQTDFGMYD YFTRQYGDES TLAFQQARYN FIRSMAAYSL LLFLLQIKDR
HNGNIMLDKK GHIIHIDFGF MFESSPGGNL GWEPDIKLTD EMVMIMGGKM
EATPFKWFME MCVRGYLAVR PYMDAVVSLV TLMLDTGLPC FRGQTIKLLK
HRFSPNMTER EAANFIMKVI QSCFLSNRSR TYDMIQYYQN DIPY

Figure 14

MASSSVPPAT VSAATAGPGP GFGFASKTKK KHFVQQKVKV FRAADPLVGV
FLWGVAHSIN ELSQVPPPVM LLPDDFKASS KIKVNNHLFH RENLPSHFKF
KEYCPQVFRN LRDRFGIDDQ DYLVSLTRNP PSESEGSDGR FLISYDRTLV
IKEVSSEDIA DMHSNLSNYH QYIVKCHGNT LLPQFLGMYR VSVDNEDSYM
LVMRNMFSHR LPVHRKYDLK GSLVSREASD KEKVKELPTL KDMDFLNKNQ
KVYIGEEEKK IFLEKLKRDV EFLVQLKIMD YSLLLGIHDI IRGSEPEEEG
PVREDESEVD GDCSLTGPPA LVGSYGTSPE GIGGYIHSHR PLGPGEFESF
IDVYAIRSAE GAPQKEVYFM GLIDILTQYD AKKKAAHAAK TVKHGAGAEI
STVHPEQYAK RFLDFITNIF A

Figure 15

MELENYKQPV VLREDNCRRR RRMKPRSAAA SLSSMELIPI EFVLPTSQRK
CKSPETALLH VAGHGNVEQM KAQVWLRALE TSVAADFYHR LGPHHFLLLY
QKKGQWYEIY DKYQVVQTLD CLRYWKATHR SPGQIHLVQR HPPSEESQAF
QRQLTALIGY DVTDVSNVHD DELEFTRRGL VTPRMAEVAS RDPKLYAMHP
WVTSKPLPEY LWKKIANNCI FIVIHRSTTS QTIKVSPDDT PGAILQSFFT
KMAKKKSLMD IPESQSEQDF VLRVCGRDEY LVGETPIKNF QWVRHCLKNG
EEIHVVLDTP PDPALDEVRK EEWPLVDDCT GVTGYHEQLT IHGKDHESVF
TVSLWDCDRK FRVKIRGIDI PVLPRNTDLT VFVEANIQHG QQVLCQRRTS
PKPFTEEVLW NVWLEFSIKI KDLPKGALLN LQIYCGKAPA LSSKASAESP
SSESKGKVQL LYYVNLLLID HRFLLRRGEY VLHMWQISGK GEDQGSFNAD
KLTSATNPDK ENSMSISILL DNYCHPIALP KHQPTPDPEG DRVRAEMPNQ
LRKQLEAIIA TDPLNPLTAE DKELLWHFRY ESLKHPKAYP KLFSSVKWGQ
QEIVAKTYQL LARREVWDQS ALDVGLTMQL LDCNFSDENV RAIAVQKLES
LEDDDVLHYL LQLVQAVKFE PYHDSALARF LLKRGLRNKR IGHFLFWFLR
SEIAQSRHYQ QRFAVILEAY LRGCGTAMLH DFTQQVQVIE MLQKVTLDIK
SLSAEKYDVS SQVISQLKQK LENLQNSQLP ESFRVPYDPG LKAGALAIEK
CKVMASKKKP LWLEFKCADP TALSNETIGI IFKHGDDLRQ DMLILQILRI
MESIWETESL DLCLLPYGCI STGDKIGMIE IVKDATTIAK IQQSTVGNTG
AFKDEVLNHW LKEKSPTEEK FQAAVERFVY SCAGYCVATF VLGIGDRHND
NIMITETGNL FHIDFGHILG NYKSFLGINK ERVPFVLTPD FLFVMGTSGK
KTSPHFQKFQ DICVKAYLAL RHHTNLLIIL FSMMLMTGMP QLTSKEDIEY
IRDALTVGKN EEDAKKYFLD QIEVCRDKGW TVQFNWFLHL VLGIKQGEKH
SA

Figure 16

MPPGVDCPME FWTKEENQSV VVDFLLPTGV YLNFPVSRNA NLSTIKQLLW
HRAQYEPLFH MLSGPEAYVF TCINQTAEQQ ELEDEQRRLC DVQPFLPVLR
LVAREGDRVK KLINSQISLL IGKGLHEFDS LCDPEVNDFR AKMCQFCEEA
AARRQQLGWE AWLQYSFPLQ LEPSAQTWGP GTLRLPNRAL LVNVKFEGSE
ESFTFQVSTK DVPLALMACA LRKKATVFRQ PLVEQPEDYT LQVNGRHEYL
YGSYPLCQFQ YICSCLHSGL TPHLTMVHSS SILAMRDEQS NPAPQVQKPR
AKPPPIPAKK PSSVSLWSLE QPFRIELIQG SKVNADERMK LVVQAGLFHG
NEMLCKTVSS SEVSVCSEPV WKQRLEFDIN ICDLPRMARL CFALYAVIEK
AKKARSTKKK SKKADCPIAW ANLMLFDYKD QLKTGERCLY MWPSVPDEKG
ELLNPTGTVR SNPNTDSAAA LLICLPEVAP HPVYYPALEK ILELGRHSEC
VHVTEEEQLQ LREILERRGS GELYEHEKDL VWKLRHEVQE HFPEALARLL
LVTKWNKHED VAQMLYLLCS WPELPVLSAL ELLDFSFPDC HVGSFAIKSL
RKLTDDELFQ YLLQLVQVLK YESYLDCELT KFLLDRALAN RKIGHFLFWH
LRSEMHVPSV ALRFGLILEA YCRGSTHHMK VLMKQGEALS KLKALNDFVK
LSSQKTPKPQ TKELMHLCMR QEAYLEALSH LQSPLDPSTL LAEVCVEQCT
FMDSKMKPLW IMYSNEEAGS GGSVGIIFKN GDDLRQDMLT LQMIQLMDVL
WKQEGLDLRM TPYGCLPTGD RTGLIEVVLR SDTIANIQLN KSNMAATAAF
NKDALLNWLK SKNPGEALDR AIEEFTLSCA GYCVATYVLG IGDRHSDNIM
IRESGQLFHI DFGHFLGNFK TKFGINRERV PFILTYDFVH VIQQGKTNNS
EKFERFRGYC ERAYTILRRH GLLFLHLFAL MRAAGLPELS CSKDIQYLKD
SLALGKTEEE ALKHFRVKFN EALRESWKTK VNWLAHNVSK DNRQ

METHODS FOR THE IDENTIFICATION OF PHOSPHATIDYLINOSITOL KINASE INTERACTING MOLECULES AND FOR THE PURIFICATION OF PHOSPHATIDYLINOSITOL KINASE PROTEINS

CROSS-REFERENCE TO RELATED APPLICATIONS

This application is the U.S. national stage filing under 35 U.S.C. §371 of international application PCT/EP2010/002987, filed May 14, 2010, which claims benefit of the filing date of European Application No. 09006786.9, filed May 20, 2009.

The present invention relates to immobilization compounds, immobilization products and preparations thereof as well as methods and uses for the identification of phosphatidylinositol kinase interacting compounds or for the purification or identification of phosphatidylinositol kinase proteins.

Phosphatidylinositol, a component of eukaryotic cell membranes, is unique among phospholipids in that its head group can be phosphorylated at multiple free hydroxyls. Several phosphorylated derivatives of phosphatidylinositol, collectively termed phosphoinositides, have been identified in eukaryotic cells. Phosphoinositides are involved in the regulation of diverse cellular processes, including proliferation, survival, cytoskeletal organization, vesicle trafficking, glucose transport, and platelet function. The enzymes that phosphorylate phosphatidylinositol and its derivatives are termed phosphatidylinositol kinases or phosphoinositide kinases (Fruman et al., 1998. Annual Rev. Biochem. 67:481-507).

Phosphoinositide 3-kinases (also called Phosphatidylinositol 3-kinases, PI3Ks) represent a a superfamily of signaling lipid kinases that catalyse the phosphorylation of phosphatidylinositol-4,5-bisphosphate (PtdIns(4,5)P2 or phosphatidylinositol (PtdIns) at the 3'-OH group, giving rise to the second messengers phosphatidylinositol-3,4,5-trisphosphate (PtdIns(3,4,5)P3) or phosphatidylinositol-3-phosphate (PtdIns(3)P). PtdIns(3,4,5)P3 can be converted into PtdIns(3,4)P2 by SH2-containing inositol phosphatase (SHIP), or can be dephosphorylated by phosphatase and tensin homologue (PTEN) phosphatase to regenerate PtdIns (4,5)P2. The 3'-phosphorylated phosphoinositides, PtdIns(3,4,5)P3, PtdIns(3,4)P2 PtdIns(4,5)P2, PtdIns(5)P and PtdIns(3)P, recruit and activate various signalling proteins (PtdInsbinding proteins; PtdIns-BPs) through direct lipid-protein interactions. Some PI3Ks also display protein kinase activity (Fruman et al., 1998, Annu. Rev. Biochem. 67:481-507).

Different types of PI3K have been identified and grouped into three classes according to their primary and secondary structures, mode of regulation and substrate specificity. Class I PI3K has been the most extensively studied so far, and includes heterodimeric proteins that consist of a catalytic and a regulatory adaptor subunit, the nature of which determines a further subdivision into class IA and IB PI3K. Class II PI3K uses PtdIns as in vivo substrate, yielding phosphatidylinositol-3-phosphate (PtdIns(3)P). Some evidence has been presented that class II enzymes, similarly to class I can be activated by external stimuli via receptor tyrosine kinases (RTKs), cytokine receptors and integrins, suggesting roles in cancer, wound healing and insulin signaling. By contrast, the class III PI3K, represented by a single species (hVps34) in humans, has relatively high activity even in resting cells. The class IA—PI3Kα, β and δ (PIK3CA, PIK3CB and PIK3CD)—consists of a SH2-domain-containing regulatory subunit (p85; five distinct isoforms of which have been identified) that forms a complex with one of three catalytic subunits, p110α, p110β or p110δ. PI3Kγ, the only member of class IB (PIK3CG), associates with either of two regulatory subunits, p101 and p84, that control its activation and subcellular location (Bader et al., 2005, Nat. Rev. Cancer 5 (12): 921-9).

Phosphatidylinositol 4-kinases catalyse the production of phosphatidylinositol 4-phosphate (PtdIns 4-phosphate, PtdIns4P) from phosphatidylinositol, the first step in the formation of PtdIns(4,5)P2 and PtdIns(3,4,5)P3, two lipid products whose functions as regulatory molecules are best understood. Four distinct phosphatidylinositol 4-kinases have been identified in mammalian cells (PI4KIIα, PI4KIIβ, PI4KIIIα (synonym PIK4CA), and PI4KIIIβ (synonym PIK4CB)) (Balla and Balla, 2006. Trends in Cell Biology 16(7):351-361).

Phosphatidylinositol-4-phosphate 5-kinases (PIP5Ks) synthesize phosphatidylinositol 4,5-bisphosphate (PIP2) by phosphorylating phosphatidylinositol 4-phosphate. As a precursor for second messengers generated by phospholipase C isoforms and class I PI3Ks, PIP2 is indispensable for cellular signaling by membrane receptors. Three isoforms of PIP5k with alternative splice variants have been cloned and characterized (PIP5K2A, PIP5K2B and PIP5K2C) so far (Weernink et al., 2004. Europ. J. Pharmacol. 500, 87-99).

The in vitro investigation of phosphatidylinositol kinase activity is typically performed using radioactively labelled ATP and the transfer of phosphor-groups into phospholipid substrates incorporated in unilamellar lipid vesicle (ULVs) followed by thin layer chromatography (TLC) analysis of reaction products. These assays are sensitive and specific but require vesicle preparation which can be challenging for large-scale production necessary for high-throughput screening to identify phosphatidylinositol kinase inhibitors. In addition, typically these assays require the availability of purified or recombinant phosphatidylinositol kinases.

For example, PI3K phosphatidylinositol kinase activity can be measured using purified or recombinant enzyme in a solution-based assay with phospholipid vesicles. The reaction is terminated by the addition of acidified organic solvents and subsequent phase separation by extraction or thin layer chromatography analysis (Carpenter et al., 1990, J. Biol. Chem. 265, 19704-19711). Another PI3K assay described in the art is based on the phosphate transfer from radiolabeled ATP to phosphatidylinositol immobilized on plates. This assay type uses recombinant PI3Kγ enzyme and can be performed in a high-throughput mode as a vesicle free assay format (Fuchikami et al., 2002, J. Biomol. Screening 7, 441-450). A high-throughput liposome PI3K assay with an automated lipid extraction process was described that allows to quantitatively measure inhibitor activity (Lingaraj et al., 2008. J. Biomol. Screening 13(9):906-11). For the phosphatidylinositol-4-phosphate 5-kinases (PIP5K) a vesicle assay was reported that uses radioactive ATP and recombinant PIP5Ks followed by thin layer chromatography or HPLC analysis of the reaction products (Tolias et al, 1998. J. Biol. Chem. 273, 18040-18046).

Another, although not in all instances necessary prerequisite for the identification of selective kinase inhibitors is a method that allows to determine the target selectivity of these molecules. For example, it can be intended to provide molecules that bind to and inhibit a particular drug target but do not interact with a closely related target, inhibition of which could lead to unwanted side effects. Conventionally large panels of individual enzyme assays are used to assess the inhibitory effect of a compound for protein kinases (Bain et al., 2007. Biochemical Journal 408(3):297-315) and lipid kinases (Garcia-Martinez et al., 2009. Biochemical Journal 421(1):29-42, PMID: 19402821).

More recently, kinases or kinase domains displayed on bacteriophages have been employed to assess the ability of a given compound to interact with a large set of kinases (Karaman et al., 2008. Nature Biotechnology 26, 127-132). In addition, chemical proteomics methods have been described which allow the profiling of kinase inhibitors against the proteome (WO 2006/134056; WO2008/015013; Bantscheff et al., 2007. Nature Biotechnology 25, 1035-1044; Patricelly et al., 2007. Biochemistry 46, 350-358; Gharbi et al., 2007. Biochem. J. 404, 15-21).

In view of the above, there is a need for providing effective tools and methods for the identification and selectivity profiling of phosphatidylinositol kinase interacting compounds as well as for the purification of phosphatidylinositol kinases.

The present invention relates inter alia to an immobilization compound of formula (I)

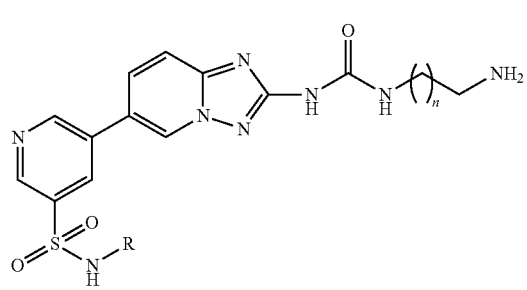

(I)

or a salt thereof, wherein
R is $C_{1-4}$ alkyl optionally substituted with one or more fluoro (preferably unsubstituted $C_{1-4}$ alkyl; more preferably, n-propyl, isopropyl, n-butyl, isobutyl, sec-butyl, or tert-butyl; even more preferably, isopropyl, or tert-butyl); and
n is 1, 2, or 3 (preferably, 1, or 2; more preferably, 1).

"$C_{1-4}$ alkyl" means an alkyl chain having 1-4 carbon atoms, i.e. methyl, ethyl, n-propyl, isopropyl, n-butyl, isobutyl, sec-butyl, tert-butyl. Each hydrogen of a $C_{1-4}$ alkyl carbon may be replaced by a substituent as further specified.

Preferred immobilization compounds of formula (I) are selected from the group consisting of

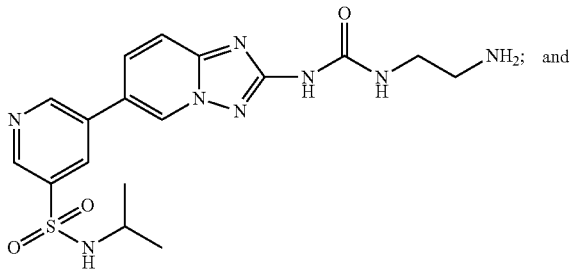

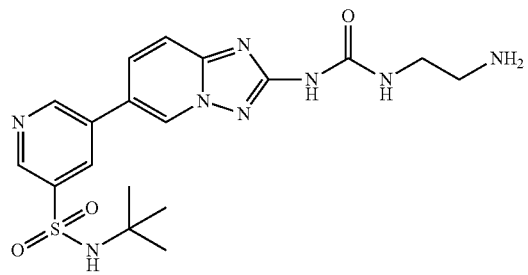

or a mixture of both.

The immobilization compounds of the present invention can be prepared by methods well known in the art. Exemplary analogous routes for the synthesis are described in, for example, in WO-A 2008/025821.

A general route for the synthesis of immobilization compounds of the present invention is shown in Example 1.

The invention further relates to a method for the preparation of an immobilization product, wherein at least one immobilization compound according to the invention is immobilized on a solid support. Such immobilization products obtainable according to the method of the invention are e.g. useful in the methods of the invention for the identification of kinase interacting compounds or in diagnostic methods for the diagnosis of inflammatory diseases, proliferative diseases and metabolic diseases.

According to the method of the invention, at least one immobilization compound of the invention is immobilized on a solid support. Throughout the invention, the term "solid support" relates to every undissolved support being able to immobilize a small molecule ligand on its surface.

According to the invention, the term "at least one immobilization compound" means either that at least one immobilization compound of the same type is immobilized on the solid support or that one or more different immobilization compounds (each of them either in singular or plural) may be immobilized on the solid support. Preferably, one or two different immobilization compounds are immobilized on the solid support, more preferably the preferred immobilization compounds of formula (I) of the present invention selected from the group consisting of

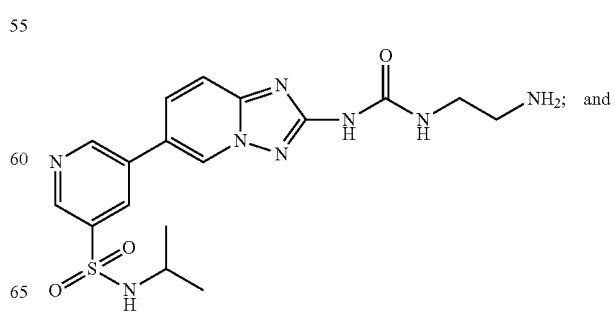

-continued

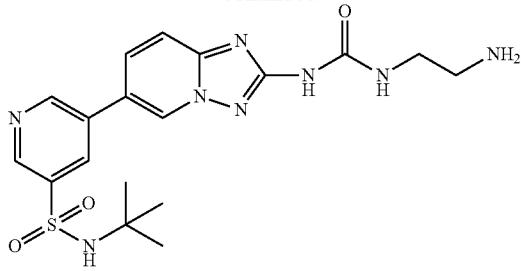

are immobilized.

The solid support may be selected from the group consisting of agarose, modified agarose, sepharose beads (e.g. NHS-activated sepharose), latex, cellulose, and ferro- or ferrimagnetic particles.

In case that the solid support is a material comprising various entities, e.g. in case that the solid support comprises several beads or particles, it is envisaged within the present invention that, if different immobilization compounds are immobilized, on each single entity, e.g. each bead or particle, one or more different immobilization compounds are immobilized. Therefore, in case that two immobilization compounds are used, it is envisaged within the present invention that on each single entity one or two different immobilization compounds are immobilized. If no measures are taken that on one entity only one different immobilization compound is immobilized, it is very likely that on each entity all different immobilization compounds will be present.

The immobilization compound or compounds of the invention may be coupled to the solid support either covalently or non-covalently. Non-covalent binding includes binding via biotin affinity ligands binding to steptavidin matrices.

Preferably, the immobilization compound or compounds are covalently coupled to the solid support.

Methods for immobilizing compounds on solid supports are known in the art and further exemplified in Example 1.

In general, before the coupling, the matrixes can contain active groups such as NHS, Carbodimide etc. to enable the coupling reaction with the immobilization compound. The immobilization compound can be coupled to the solid support by direct coupling (e.g. using functional groups such as amino-, sulfhydryl-, carboxyl-, hydroxyl-, aldehyde-, and ketone groups) and by indirect coupling (e.g. via biotin, biotin being covalently attached to the immobilization product of the invention and non-covalent binding of biotin to streptavidin which is bound directly to the solid support).

The linkage to the solid support material may involve cleavable and non-cleavable linkers. The cleavage may be achieved by enzymatic cleavage or treatment with suitable chemical methods.

Therefore, according to a preferred embodiment of the invention, the immobilization product results from a covalent direct or linker mediated attachment of the at least one immobilization compound of the invention to the solid support.

The linker may be a $C_{1-10}$ alkylene group, which is optionally interrupted or terminated by one or more atoms or functional groups selected from the group consisting of S, O, NH, C(O)O, C(O), and C(O)NH and wherein the linker is optionally substituted with one or more substituents independently selected from the group consisting of halogen, OH, $NH_2$, C(O)H, $C(O)NH_2$, $SO_3H$, $NO_2$, and CN.

The term "$C_{1-10}$ alkylene" means an alkylene chain having 1-10 carbon atoms, e.g. methylene, ethylene, —CH═CH—, —C≡C—, n-propylene and the like, wherein each hydrogen of a carbon atom may be replaced by a substituent.

The term "interrupted" means that the one or more atoms or functional groups are inserted between two carbon atoms of the alkylene chain or—when "terminated"—at the end of said chain.

The invention further relates to an immobilization product, obtainable by the method of the invention.

Furthermore, the present invention relates to an immobilization product, comprising the immobilization compound of the invention immobilized on a solid support, in particular wherein the solid support is selected from the group consisting of agarose, modified agarose, sepharose beads (e.g. NHS-activated sepharose), latex, cellulose, and ferro- or ferrimagnetic particles.

Therefore, an immobilization product which is obtainable by the method of the invention is or comprises an immobilization compound of the present invention immobilized on a solid support. This immobilization product will be referred to in the following as the immobilization product of the invention and is used in the methods of the present invention.

In a preferred embodiment, the immobilization compound or immobilization product of the invention may further be labeled.

By "labeled" is meant that the respective substance is either directly or indirectly labeled with a molecule which provides a detection signal, e.g. radioisotope, fluorescent tag, chemiluminescent tag, a peptide or specific binding molecules. Specific binding molecules include pairs, such as biotin and streptavidin, digoxin and antidigoxin. The label can directly or indirectly provide a detectable signal. The tag can also be a peptide which can be used, for example, in an enzyme fragment complementation assay (e.g. beta-galactosidase enzyme fragment complementation; Zaman et al., 2006. Assay Drug Dev. Technol. 4(4):411-420). The labeled compounds would be useful not only in imaging techniques but also in assays, both in vitro and in vivo, for identifying kinase interacting compounds by inhibition of binding of the labeled compound, for example in kinase assays that contain such labeled compounds.

Radioisotopes are commonly used in biological applications for the detection of a variety of biomolecules and have proven to be useful in binding assays. Several examples of probes have been designed to incorporate $^3H$ (also written as T for tritium) because it can replace hydrogen in a probe without altering its structure (Fenteany et al., 1995. Science 268:726-731). An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written D for Deuterium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$.

Guidance for the selection and methods for the attachment of fluorescent tags (e.g. fluorescein, rhodamine, dansyl, NBD (nitrobenz-2-oxa-1,3-diazole), BODIPY (dipyrromethene boron difluoride), and cyanine (Cy)-dyes) to small molecule ligands are generally known in the art (Vedvik et al., 2004. Assay Drug Dev. Technol. 2(2): 193-203; Zhang et al., 2005. Analytical Biochemistry 343(1):76-83). The application of fluorescent probes (fluorophores) in assays for high throughput screening (HTS) of protein kinases was described (Zaman et al., 2003. Comb. Chem. High Throughput Screen 6(4): 313-320). The change of the fluorescent properties after binding of the fluorescent probe to the target kinase can be determined by measuring for example fluorescence polarization (Kashem et al., 2007. J. Biomol. Screening 12(1):70-83), fluorescence resonance energy transfer (FRET; Zhang et al., 2005. Analytical Biochemistry 343(1):76-83) or fluorescence lifetime (Moger et al., 2006. J. Biomol. Screening 11(7): 765-772). In addition, the ALPHAScreen technology can be used where the excitation of a donor bead at 680 nm produces singlet oxygen which can diffuse to an acceptor bead undergoing a chemiluminescent reaction (Glickman et al., 2002. J. Biomol. Screen. 7(1):3-10).

One possible use of the immobilization products of the invention is in the context of the identification of compounds interacting with phosphatidylinositol kinases. Therefore, the present invention also relates to such methods and uses.

In a first aspect of the methods of the invention, the invention therefore relates to a method for the identification of a phosphatidylinositol kinase interacting compound, comprising the steps of
  a) providing a protein preparation containing a variety of phosphatidylinositol kinases,
  b) contacting the protein preparation with the immobilization product of the invention under conditions allowing the formation of one or more different complexes between one of the phosphatidylinositol kinases and the immobilization product,
  c) incubating the one or more different complexes with a given compound, and
  d) determining whether the compound is able to separate the phosphatidylinositol kinase from the immobilization product.

In a second aspect, the present invention relates into a method for the identification of a phosphatidylinositol kinase interacting compound, comprising the steps of
  a) providing a protein preparation containing a variety of phosphatidylinositol kinases,
  b) contacting the protein preparation with the immobilization product of the invention and with a given compound under conditions allowing the formation of one or more different complexes between one of the phosphatidylinositol kinases and the immobilization product, and
  c) detecting the complex or the complexes formed in step b).

In a third aspect, the present invention relates to a method for the identification of a phosphatidylinositol kinase interacting compound, comprising the steps of:
  a) providing two aliquots of a protein preparation containing a variety of phosphatidylinositol kinases,
  b) contacting one aliquot with the immobilization product of the invention under conditions allowing the formation of one or more different complexes between one of the phosphatidylinositol kinases and the immobilization product,
  c) contacting the other aliquot with the immobilization product of the invention and with a given compound under conditions allowing the formation of one or more different complexes between one of the phosphatidylinositol kinases and the immobilization product, and
  d) determining the amount of the complex or the complexes formed in steps b) and c).

In a fourth aspect, the invention relates to a method for the identification of a phosphatidyl-inositol kinase interacting compound, comprising the steps of:
  a) providing two aliquots of a cell preparation comprising each at least one cell containing a variety of phosphatidylinositol kinases,
  b) incubating one aliquot with a given compound,
  c) harvesting the cells of each aliquot,
  d) lysing the cells in order to obtain protein preparations,
  e) contacting the protein preparations with the immobilization product of the invention under conditions allowing the formation of one or more different complexes between one of the phosphatidylinositol kinases and the immobilization product, and
  f) determining the amount of the complex or the complexes formed in each aliquot in step e).

In the context of the present invention, it has been found that the immobilization products of the present invention are suitable for the identification of compounds interacting with phosphatidylinositol kinases.

The immobilization products of the present invention bind to a variety of kinases, especially phosphatidylinositol kinases. Especially, they bind to kinases listed in tables 4, 5 and 6 shown in the examples.

For example, the following kinases were identified in example 2 (Table 4):
PIK3Ca, PIK3Cb, PIK4Ca, PIP5K2C, PIK3Cg, P1K3Cd.

In addition, for example, the following kinases were identified in example 3 (Table 5):
PIP5K2A, PIK4C2B, PIK3C3.

In addition, for example, the following kinases were identified in example 4 (Table 6):
PIP5K2B, PIK3C2b.

Consequently, in the methods of the present invention, these immobilization products can be used to identify compounds binding to at least one kinase out of said variety of phosphatidylinositol kinases.

According to the present invention, the expression "phosphatidylinositol kinase" means enzymes that phosphorylate phosphatidylinositol or its phosphorylated derivatives.

According to the present invention, the term "variety" means one or more different types of the enzyme class of interest, in the present case phosphatidylinositol kinases.

Examples of phosphatidylinositol kinases are:
Phosphatidylinositol-4,5-bisphosphate 3-kinase catalytic subunit alpha (PIK3Ca),
Phosphatidylinositol-4,5-bisphosphate 3-kinase catalytic subunit beta (PIK3Cb);
Phosphatidylinositol-4,5-bisphosphate 3-kinase catalytic subunit gamma (PIK3Cg);
Phosphatidylinositol-4,5-bisphosphate 3-kinase catalytic subunit delta (PIK3Cd);
Phosphatidylinositol-4-phosphate 3-kinase C2 domain-containing beta (PIK3C2b);
Phosphatidylinositol 3-kinase catalytic subunit type 3 (PIK3C3; VPS34 homolog);
Phosphatidylinositol 4-kinase alpha (PIK4Ca);
Phosphatidylinositol 4-kinase type 2-beta (PIK4C2B);
Phosphatidylinositol-4-phosphate 5-kinase type-2 alpha (PIP5K2A);
Phosphatidylinositol-4-phosphate 5-kinase type-2 beta (PIP5K2B);
Phosphatidylinositol-4-phosphate 5-kinase type-2 gamma (PIP5K2C).

According to the present invention, the expression "phosphatidylinositol kinase" relates to both human and other proteins of this family. The expression especially includes functionally active derivatives thereof, or functionally active fragments thereof, or a homologues thereof, or variants encoded by a nucleic acid that hybridizes to the nucleic acid encoding said protein under low stringency conditions. Preferably, these low stringency conditions include hybridization in a buffer comprising 35% formamide, 5×SSC, 50 mM Tris-HCl (pH 7.5), 5 mM EDTA, 0.02% PVP, 0.02% BSA, 100 ug/ml denatured salmon sperm DNA, and 10% (wt/vol) dextran sulfate for 18-20 hours at 40° C., washing in a buffer consisting of 2×SSC, 25 mM Tris-HCl (pH 7.4), 5 mM EDTA, and 0.1% SDS for 1-5 hours at 55° C., and washing in a buffer consisting of 2×SSC, 25 mM Tris-HCl (pH 7.4) 5 mM EDTA, and 0.1% SDS for 1.5 hours at 60° C.

Moreover, according to the present invention, the expression "phosphatidylinositol kinase" includes mutant forms said kinases. For example, the PIK3CA gene encoding the catalytic subunit p110α is frequently mutated in human solid tumours. Cancer-specific mutations are clustered in the helical and the kinase domains of p110α with amino acid residues E542, E545 and H1047 as prominent mutational hotspots (Bader et al., 2005. Nature Reviews Cancer 5, 921-929), In some aspects of the invention, first a protein preparation containing said phosphatidylinositol kinases or kinase is provided. The methods of the present invention can be performed with any protein preparation as a starting material, as long as the respective kinase is solubilized in the preparation. Examples include a liquid mixture of several proteins, a cell lysate, a partial cell lysate which contains not all proteins present in the original cell or a combination of several cell lysates. The term "protein preparation" also includes dissolved purified protein.

In another aspect of the invention, aliquots of a cell preparation are provided as the starting material. In the context of the present invention, the term "cell preparation" refers to any preparation containing at least one cell with the desired properties. Suitable cell preparation are described below.

The presence of the phosphatidylinositol kinases in a protein preparation of interest can be detected on Western blots probed with antibodies that are specifically directed against said kinase. Alternatively, also mass spectrometry (MS) could be used to detect the kinases (see below).

Cell lysates or partial cell lysates can be obtained by isolating cell organelles (e.g. nucleus, mitochondria, ribosomes, golgi etc.) first and then preparing protein preparations derived from these organelles. Methods for the isolation of cell organelles are known in the art (Chapter 4.2 Purification of Organelles from Mammalian Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

In addition, protein preparations can be prepared by fractionation of cell extracts thereby enriching specific types of proteins such as cytoplasmic or membrane proteins (Chapter 4.3 Subcellular Fractionation of Tissue Culture Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

Furthermore protein preparations from body fluids can be used (e.g. blood, cerebrospinal fluid, peritoneal fluid and urine).

For example whole embryo lysates derived from defined development stages or adult stages of model organisms such as C. elegans can be used. In addition, whole organs such as heart dissected from mice can be the source of protein preparations. These organs can also be perfused in vitro in order to obtain a protein preparation.

Furthermore, the protein preparation may be a preparation containing the kinase or the kinases which has been recombinantely produced. Methods for the production of recombinant proteins in prokaryotic and eukaryotic cells are widely established (Chapter 5 Production of Recombinant Proteins in "Current Protocols in Protein Science", Editors: John. E. Coligan, Ben M. Dunn, Hidde L. Ploegh, David W. Speicher, Paul T. Wingfield; Wiley, 1995, ISBN: 0-471-14098-8).

In a preferred embodiment of the methods of the invention, the provision of a protein preparation includes the steps of harvesting at least one cell containing the phosphatidylinositol kinase or the kinases and lysing the cell.

Suitable cells for this purpose as well as for the cell preparations used as the starting material in one aspect of the present invention are e.g. those cells or tissues where the kinases are expressed. In any given cell or tissue only a subset of the kinome may be expressed. Therefore it may be necessary to generate multiple protein preparations from a variety of cell types and tissues to cover the kinome, especially for selectivity profiling of kinase inhibitors. As established cell lines may not reflect the physiological expression pattern of kinases, primary animal or human cells may be used, for example cells isolated from blood samples.

Therefore, in a preferred embodiment, cells isolated from peripheral blood represent a suitable biological material. Procedures for the preparation and culture of human lymphocytes and lymphocyte subpopulations obtained from peripheral blood (PBLs) are widely known (W. E Biddison, Chapter 2.2 "Preparation and culture of human lymphocytes" in Current Protocols in Cell Biology, 1998, John Wiley & Sons, Inc.). For example, density gradient centrifugation is a method for the separation of lymphocytes from other blood cell populations (e.g. erythrocytes and granulocytes). Human lymphocyte subpopulations can be isolated via their specific cell surface receptors which can be recognized by monoclonal antibodies. The physical separation method involves coupling of these antibody reagents to magnetic beads which allow the enrichment of cells that are bound by these antibodies (positive selection).

As an alternative to primary human cells cultured cell lines (e.g. MOLT-4 cells, Jurkat, Ramos or HeLa cells) can be used.

In a preferred embodiment, the cell is part of a cell culture system and methods for the harvest of a cell out of a cell culture system are known in the art (literature supra).

The choice of the cell will mainly depend on the expression of the phosphatidylinositol kinases, since it has to be ensured that the protein is principally present in the cell of choice. In order to determine whether a given cell is a suitable starting system for the methods of the invention, methods like Westernblot, PCR-based nucleic acids detection methods, Northernblots and DNA-microarray methods ("DNA chips") might be suitable in order to determine whether a given protein of interest is present in the cell.

The choice of the cell may also be influenced by the purpose of the study. If the in vivo efficacy for a given drug needs to be analyzed then cells or tissues may be selected in which the desired therapeutic effect occurs (e.g. B-cells). By contrast, for the elucidation of protein targets mediating unwanted side effects the cell or tissue may be analysed in which the side effect is observed (e.g. cardiomyocytes, vascular smooth muscle or epithelium cells).

Furthermore, it is envisaged within the present invention that the cell containing the phosphatidylinositol kinases or the kinase may be obtained from an organism, e.g. by biopsy. Corresponding methods are known in the art. For example, a biopsy is a diagnostic procedure used to obtain a small amount of tissue, which can then be examined microscopically or with biochemical methods. Biopsies are important to diagnose, classify and stage a disease, but also to evaluate and monitor drug treatment.

It is encompassed within the present invention that by the harvest of the at least one cell, the lysis is performed simultaneously. However, it is equally preferred that the cell is first harvested and then separately lysed.

Methods for the lysis of cells are known in the art (Karwa and Mitra: Sample preparation for the extraction, isolation, and purification of Nuclei Acids; chapter 8 in "Sample Preparation Techniques in Analytical Chemistry", Wiley 2003, Editor: Somenath Mitra, print ISBN: 0471328456; online ISBN: 0471457817). Lysis of different cell types and tissues can be achieved by homogenizers (e.g. Potter-homogenizer), ultrasonic desintegrators, enzymatic lysis, detergents (e.g. NP-40, Triton X-100, CHAPS, SDS), osmotic shock, repeated freezing and thawing, or a combination of these methods.

According to the methods of the invention, the protein preparation containing one or more phosphatidylinositol kinases is contacted with the immobilization product under conditions allowing the formation of a complex between the said kinase and the immobilization product of the invention.

In the present invention, the term "a complex between a phosphatidylinositol kinase and the immobilization product" denotes a complex where the immobilization product interacts with a phosphatidylinositol kinase, e.g. by covalent or, most preferred, by non-covalent binding.

In the context of the present invention, compounds are identified which interfere with the formation of a complex between the immobilization product and a phosphatidylinositol kinase present in a cell or protein preparation. In case that only one phosphatidylinositol kinase is to be detected or present, the formation of one complex is observed and tested. In case that several kinases are to be detected or present, the formation of several, different complexes is observed and tested.

The skilled person will know which conditions can be applied in order to enable the formation of said complex.

In the context of the present invention, the term "under conditions allowing the formation of the complex" includes all conditions under which such formation, preferably such binding is possible. This includes the possibility of having the solid support on an immobilized phase and pouring the lysate onto it. In another preferred embodiment, it is also included that the solid support is in a particulate form and mixed with the cell lysate. Such conditions are known to the person skilled in the art.

In the context of non-covalent binding, the binding between the immobilization product and the kinase is, e.g., via salt bridges, hydrogen bonds, hydrophobic interactions or a combination thereof.

In a preferred embodiment, the steps of the formation of said complex are performed under essentially physiological conditions. The physical state of proteins within cells is described in Petty, 1998 (Howard R. Petty, Chapter 1, Unit 1.5 in: Juan S. Bonifacino, Mary Dasso, Joe B. Harford, Jennifer Lippincott-Schwartz, and Kenneth M. Yamada (eds.) *Current Protocols in Cell Biology* Copyright © 2003 John Wiley & Sons, Inc. All rights reserved. DOI: 10.1002/0471143030.cb0101s00Online Posting Date: May, 2001Print Publication Date: October, 1998).

The contacting under essentially physiological conditions has the advantage that the interactions between the ligand, the cell preparation (i.e. the phosphatidylinositol kinase to be characterized) and optionally the compound reflect as much as possible the natural conditions. "Essentially physiological conditions" are inter alia those conditions which are present in the original, unprocessed sample material. They include the physiological protein concentration, pH, salt concentration, buffer capacity and post-translational modifications of the proteins involved. The term "essentially physiological conditions" does not require conditions identical to those in the original living organism, wherefrom the sample is derived, but essentially cell-like conditions or conditions close to cellular conditions. The person skilled in the art will, of course, realize that certain constraints may arise due to the experimental set-up which will eventually lead to less cell-like conditions. For example, the eventually necessary disruption of cell walls or cell membranes when taking and processing a sample from a living organism may require conditions which are not identical to the physiological conditions found in the organism. Suitable variations of physiological conditions for practicing the methods of the invention will be apparent to those skilled in the art and are encompassed by the term "essentially physiological conditions" as used herein. In summary, it is to be understood that the term "essentially physiological conditions" relates to conditions close to physiological conditions, as e.g. found in natural cells, but does not necessarily require that these conditions are identical.

For example, "essentially physiological conditions" may comprise 50-200 mM NaCl or KCl, pH 6.5-8.5, 20-37° C., and 0.001-10 mM divalent cation (e.g. Mg++, Ca++,); more preferably about 150 m NaCl or KCl, pH7.2 to 7.6, 5 mM divalent cation and often include 0.01-1.0 percent non-specific protein (e.g. BSA). A non-ionic detergent (Tween, NP-40, Triton-X100) can often be present, usually at about 0.001 to 2%, typically 0.05-0.2% (volume/volume). For general guidance, the following buffered aqueous conditions may be applicable: 10-250 mM NaCl, 5-50 mM Tris HCl, pH5-8, with optional addition of divalent cation(s) and/or metal chelators and/or non-ionic detergents.

Preferably, "essentially physiological conditions" mean a pH of from 6.5 to 7.5, preferably from 7.0 to 7.5, and/or a buffer concentration of from 10 to 50 mM, preferably from 25 to 50 mM, and/or a concentration of monovalent salts (e.g. Na or K) of from 120 to 170 mM, preferably 150 mM. Divalent salts (e.g. Mg or Ca) may further be present at a concentration of from 1 to 5 mM, preferably 1 to 2 mM, wherein more preferably the buffer is selected from the group consisting of Tris-HCl or HEPES.

The skilled person will appreciate that between the individual steps of the methods of the invention, washing steps may be necessary. Such washing is part of the knowledge of the person skilled in the art. The washing serves to remove non-bound components of the cell lysate from the solid support. Nonspecific (e.g. simple ionic) binding interactions can be minimized by adding low levels of detergent or by moderate adjustments to salt concentrations in the wash buffer.

According to the identification methods of the invention, the read-out system is either the detection or determination of a phosphatidylinositol kinase (first aspect of the invention), the detection of the complex between a phosphatidylinositol kinase and the immobilization product (second aspect of the invention), or the determination of the amount of the complex between a phosphatidylinositol kinase and the immobilization product (second, third and fourth aspect of the invention).

In the method according to the first aspect of the invention, the detection or determination of the amount of separated phosphatidylinositol kinase is preferably indicative for the fact that the compound is able to separate the phosphatidylinositol kinase from the immobilization product. This capacity indicates that the respective compound interacts, preferably binds to the phosphatidylinositol kinase, which is indicative for its therapeutic potential.

In one embodiment of the method according to the second aspect of the invention, the complex formed during the method of the invention is detected. The fact that such complex is formed preferably indicates that the compound does not completely inhibit the formation of the complex. On the other hand, if no complex is formed, the compound is presumably a strong interactor with the phosphatidylinositol kinase, which is indicative for its therapeutic potential.

According to the methods of the second, third and fourth aspect of the invention the amount of the complex formed during the method is determined. In general, the less complex in the presence of the respective compound is formed, the stronger the respective compound interacts with the phosphatidylinositol kinase, which is indicative for its therapeutic potential.

The detection of the complex formed according to the second aspect of the invention can be performed by using labeled antibodies directed against the phosphatidylinositol kinase and a suitable readout system.

According to a preferred embodiment of the second aspect of the invention, the complex between one phosphatidylinositol kinase and the immobilization product is detected by determining its amount.

In the course of the second, third and fourth aspect of the invention, it is preferred that the phosphatidylinositol kinase are separated from the immobilization product in order to determine the amount of said complex.

According to invention, separating means every action which destroys the interactions between the immobilization compound and the phosphatidylinositol kinase. This includes in a preferred embodiment the elution of the phosphatidylinositol kinase from the immobilization compound.

The elution can be achieved by using non-specific reagents as described in detail below (ionic strength, pH value, detergents). In addition, it can be tested whether a compound of interest can specifically elute the phosphatidylinositol kinase from the immobilization compound. Such phosphatidylinositol kinase interacting compounds are described further in the following sections.

Such non-specific methods for destroying the interaction are principally known in the art and depend on the nature of the ligand enzyme interaction. Principally, change of ionic strength, the pH value, the temperature or incubation with detergents are suitable methods to dissociate the target enzymes from the immobilized compound. The application of an elution buffer can dissociate binding partners by extremes of pH value (high or low pH; e.g. lowering pH by using 0.1 M citrate, pH2-3), change of ionic strength (e.g. high salt concentration using NaI, KI, $MgCl_2$, or KCl), polarity reducing agents which disrupt hydrophobic interactions (e.g. dioxane or ethylene glycol), or denaturing agents (chaotropic salts or detergents such as Sodium-docedyl-sulfate, SDS; Review: Subramanian A., 2002, Immunoaffinty chromatography).

In some cases, the solid support has preferably to be separated from the released material. The individual methods for this depend on the nature of the solid support and are known in the art. If the support material is contained within a column the released material can be collected as column flowthrough. In case the support material is mixed with the lysate components (so called batch procedure) an additional separation step such as gentle centrifugation may be necessary and the released material is collected as supernatant. Alternatively magnetic beads can be used as solid support so that the beads can be eliminated from the sample by using a magnetic device.

In step d) of the method according to the first aspect of the invention, it is determined if the phosphatidylinositol kinase has been separated from the immobilization product of the invention. This may include the detection of the phosphatidylinositol kinase or the determination of the amount of the phosphatidylinositol kinase.

Consequently, at least in preferred embodiments of all identification methods of the invention, methods for the detection of a separated phosphatidylinositol kinase or for the determination of their amount are used. Such methods are known in the art and include physico-chemical methods such as protein sequencing (e.g. Edmann degradation), analysis by mass spectrometry methods or immunodetection methods employing antibodies directed against the kinase.

Throughout the invention, if an antibody is used in order to detect a phosphatidylinositol kinase or in order to determine its amount (e.g. via ELISA), the skilled person will understand that, if a specific phosphatidylinositol kinase is to be detected or if the amount of a phosphatidylinositol kinase is to be determined, a specific antibody may be used (Sasaki et al., 2000, Nature 406, 897-902; Deora et al., 1998, J. Biol. Chem. 273, 29923-29928). As indicated above, such antibodies are known in the art. Furthermore, the skilled person is aware of methods for producing the same.

Preferably, a phosphatidylinositol kinase is detected or the amount of a phosphatidyl-inositol kinase is determined by mass spectrometry or immunodetection methods.

The identification of proteins with mass spectrometric analysis (mass spectrometry) is known in the art (Shevchenko et al., 1996, Analytical Chemistry 68: 850-858; Mann et al., 2001, Analysis of proteins and proteomes by mass spectrometry, Annual Review of Biochemistry 70, 437-473) and is further illustrated in the example section.

Preferably, the mass spectrometry analysis is performed in a quantitative manner, for example by using iTRAQ technology (isobaric tags for relative and absolute quantification) or cICAT (cleavable isotope-coded affinity tags) (Wu et al., 2006. J. Proteome Res. 5, 651-658).

According to a further preferred embodiment of the present invention, the characterization by mass spectrometry (MS) is performed by the identification of proteotypic peptides of the kinase. The idea is that the phosphatidylinositol kinase is digested with proteases and the resulting peptides are determined by MS. As a result, peptide frequencies for peptides from the same source protein differ by a great degree, the most frequently observed peptides that "typically" contribute to the identification of this protein being termed "proteotypic peptide". Therefore, a proteotypic peptide as used in the present invention is an experimentally well observable peptide that uniquely identifies a specific protein or protein isoform.

According to a preferred embodiment, the characterization is performed by comparing the proteotypic peptides obtained in the course of practicing the methods of the invention with known proteotypic peptides. Since, when using fragments prepared by protease digestion for the identification of a protein in MS, usually the same proteotypic peptides are observed for a given phosphatidylinositol kinase, it is possible to compare the proteotypic peptides obtained for a given sample with the proteotypic peptides already known for phosphatidylinositol kinases and thereby identifying the phosphatidylinositol kinase being present in the sample.

As an alternative to mass spectrometry analysis, the eluted phosphatidylinositol kinase (including coeluted binding partners such as regulatory subunits), can be detected or its amount can be determined by using a specific antibody directed against the phosphatidylinositol kinase.

Furthermore, in another preferred embodiment, once the identity of the coeluted binding partner (e.g. regulatory subunit) has been established by mass spectrometry analysis, each binding partner can be detected with specific antibodies directed against this protein.

Suitable antibody-based assays include but are not limited to Western blots, ELISA assays, sandwich ELISA assays and antibody arrays or a combination thereof. The establishment of such assays is known in the art (Chapter 11, Immunology, pages 11-1 to 11-30 in: Short Protocols in Molecular Biology. Fourth Edition, Edited by F. M. Ausubel et al., Wiley, New York, 1999).

These assays can not only be configured in a way to detect and quantify a phosphatidylinositol kinase interacting protein of interest (e.g. a catalytic or regulatory subunit of a kinase complex), but also to analyse posttranslational modification patterns such as phosphorylation or ubiquitin modification.

Furthermore, the identification methods of the invention involve the use of compounds which are tested for their ability to be a phosphatidylinositol kinase interacting compound.

Principally, according to the present invention, such a compound can be every molecule which is able to interact with the phosphatidylinositol kinase, eg. by inhibiting its binding to the immobilization product of the invention. Preferably, the compound has an effect on the phosphatidylinositol kinase, e.g. a stimulatory or inhibitory effect.

Preferably, said compound is selected from the group consisting of synthetic or naturally occurring chemical compounds or organic synthetic drugs, more preferably small molecule organic drugs or natural small molecule compounds. Preferably, said compound is identified starting from a library containing such compounds. Then, in the course of the present invention, such a library is screened.

Such small molecules are preferably not proteins or nucleic acids. Preferably, small molecules exhibit a molecular weight of less than 1000 Da, more preferred less than 750 Da, most preferred less than 500 Da.

A "library" according to the present invention relates to a (mostly large) collection of (numerous) different chemical entities that are provided in a sorted manner that enables both a fast functional analysis (screening) of the different individual entities, and at the same time provide for a rapid identification of the individual entities that form the library. Examples are collections of tubes or wells or spots on surfaces that contain chemical compounds that can be added into reactions with one or more defined potentially interacting partners in a high-throughput fashion. After the identification of a desired "positive" interaction of both partners, the respective compound can be rapidly identified due to the library construction. Libraries of synthetic and natural origins can either be purchased or designed by the skilled artisan.

Examples of the construction of libraries are provided in, for example, Breinbauer R, Manger M, Scheck M, Waldmann H. Natural product guided compound library development. Curr. Med. Chem. 2002; 9(23):2129-2145, wherein natural products are described that are biologically validated starting points for the design of combinatorial libraries, as they have a proven record of biological relevance. This special role of natural products in medicinal chemistry and chemical biology can be interpreted in the light of new insights about the domain architecture of proteins gained by structural biology and bioinformatics. In order to fulfill the specific requirements of the individual binding pocket within a domain family it may be necessary to optimise the natural product structure by chemical variation. Solid-phase chemistry is said to become an efficient tool for this optimisation process, and recent advances in this field are highlighted in this review article. The current drug discovery processes in many pharmaceutical companies require large and growing collections of high quality lead structures for use in high throughput screening assays. Collections of small molecules with diverse structures and "drug-like" properties have, in the past, been acquired by several means: by archive of previous internal lead optimisation efforts, by purchase from compound vendors, and by union of separate collections following company mergers. Although high throughput/combinatorial chemistry is described as being an important component in the process of new lead generation, the selection of library designs for synthesis and the subsequent design of library members has evolved to a new level of challenge and importance. The potential benefits of screening multiple small molecule compound library designs against multiple biological targets offers substantial opportunity to discover new lead structures.

In a preferred embodiment of the second and third aspect of the invention, the phosphatidylinositol kinase containing protein preparation is first incubated with the compound and then with the immobilization product. However, the simultaneous incubation of the compound and the immobilization product of the invention (coincubation) with the phosphatidylinositol kinase containing protein preparation is equally preferred (competitive binding assay).

In case that the incubation with the compound is first, the phosphatidylinositol kinase is preferably first incubated with the compound for 10 to 60 minutes, more preferred 30 to 45 minutes at a temperature of 4° C. to 37° C., more preferred 4° C. to 25° C., most preferred 4° C. Preferably compounds are used at concentrations ranging from 1 nM to 100 µM, preferably from 10 nM to 10 µM. The second step, contacting with the immobilized ligand, is preferably performed for 10 to 60 minutes at 4° C.

In case of simultaneous incubation, the phosphatidylinositol kinase is preferably simultaneously incubated with the compound and the immobilization product of the invention for 30 to 120 minutes, more preferred 60 to 120 minutes at a temperature of 4° C. to 37° C., more preferred 4° C. to 25° C., most preferred 4° C. Preferably compounds are used at concentrations ranging from 1 nM to 100 µM, preferably from 10 nM to 10 µM.

Furthermore, steps a) to c) of the second aspect of the invention may be performed with several protein preparations in order to test different compounds. This embodiment is especially interesting in the context of medium or high throughput screenings (see below).

In a preferred embodiment of the method of the invention according to the third or fourth aspect, the amount of the complex formed in step c) is compared to the amount formed in step b)

In a preferred embodiment of the method of the invention according to the third or fourth aspect, a reduced amount of the complex formed in step c) in comparison to step b) indicates that a phosphatidylinositol kinase is a target of the compound. This results from the fact that in step c) of this method of the invention, the compound competes with the immobilized compound for the binding of the kinase. If less kinase is present in the aliquot incubated with the compound, this means preferably that the compound has competed with the inhibitor for the interaction with the enzyme and is, therefore, a direct target of the protein and vice versa.

Preferably, the identification methods of the invention are performed as a medium or high throughput screening.

The interaction compound identified according to the present invention may be further characterized by determining whether it has an effect on the phosphatidylinositol kinase, for example on its kinase activity (Carpenter et al., 1990, J. Biol. Chem. 265, 19704-19711).

The compounds identified according to the present invention may further be optimized (lead optimisation). This subsequent optimisation of such compounds is often accelerated because of the structure-activity relationship (SAR) information encoded in these lead generation libraries. Lead optimisation is often facilitated due to the ready applicability of high-throughput chemistry (HTC) methods for follow-up synthesis. An example for lead optimization of PI3Kγ inhibitors was reported (Pomel et al., 2006. J. Med. Chem. 49(13): 3857-3871).

The invention further relates to a method for the preparation of a pharmaceutical composition comprising the steps of
a) identifying a phosphatidylinositol kinase interacting compound as described above, and
b) formulating the interacting compound to a pharmaceutical composition.

Methods for the formulation of identified compounds are known in the art. Furthermore, it is known in the art how to administer such pharmaceutical compositions.

The obtained pharmaceutical composition can be used for the prevention or treatment of diseases where the respective phosphatidylinositol kinase plays a role, e.g. for the prevention or treatment of cancer (Wymann and Schneiter, 2008. Nature Reviews Molecular cell Biology 9, 162-176). For example, phosphatidylinositol kinase inhibitors may be useful for the treatment of inflammatory diseases, cancer or metabolic diseases.

The invention further relates to a method for the purification of a phosphatidylinositol kinase, comprising the steps of
a) providing a protein preparation containing said kinase,
b) contacting the protein preparation with the immobilization product of the invention under conditions allowing the formation of a complex between the phosphatidylinositol kinase and the immobilization product, and
c) separating the phosphatidylinositol kinase from the immobilization product.

As mentioned above, it has been surprisingly found that the compound of the invention and therefore also the immobilization product of the invention is a ligand which recognizes the kinases mentioned above. This enables efficient purification methods for said kinases.

Preferred kinases to be purified include:
PIK3Ca, PIK3Cb, PIK4Ca, PIP5K2C, PIK3Cg, PIK3Cd, PIP5K2A, PIK4C2B, PIK3C3, PIP5K2B, PIK3C2b.

With respect to the phosphatidylinositol kinases, the protein preparation containing the phosphatidylinositol kinases, the conditions for contacting with the immobilization product of the invention, the immobilization product of the invention, the complex between the phosphatidylinositol kinases and the immobilization product of the invention, the separation of the phosphatidylinositol kinases from the immobilization product of the invention, and the detection of the phosphatidylinositol kinases or the determination of its amount, the embodiments as defined above for the identification methods of the invention also apply to the purification method of the invention.

In a preferred embodiment, the purification method of the invention further comprises after step c) the identification of proteins being capable of binding to said phosphatidylinositol kinases. This is especially interesting when the formation of the complex is performed under essentially physiological conditions, because it is then possible to preserve the natural condition of the enzyme which includes the existence of binding partners, enzyme subunits or post-translational modifications, which can then be identified with the help of mass spectrometry (MS).

Consequently, in a preferred embodiment, the purification method of the invention further comprises after step c) the determination whether the phosphatidylinositol kinase is further posttranslationally modified, e.g. by ubiquitin modification.

The binding proteins or the posttranslational modifications can be determined as explained above for the detection of phosphatidylinositol kinases or the determination of the amount of phosphatidylinositol kinases. Preferably, said methods include mass spectrometry of immunodetection methods as described above.

The invention further relates to a method for determining the presence of one or more kinases in a sample, comprising the steps of:
a) providing a protein preparation expected to contain said one or more phosphatidylinositol kinases,
b) contacting the protein preparation with the immobilization product of the invention under conditions allowing the formation of a complex between one of the phosphatidylinositol kinases and the immobilization product, and
c) detecting whether one or more phosphatidylinositol kinases have formed a complex with the immobilization product.

In a preferred embodiment of the invention, said detecting in step c) is performed by separating said one or more phosphatidylinositol kinases from the immobilization product and further identification of said one or more phosphatidylinositol kinases.

Said identification may be performed by mass spectrometry or immunodetection methods as described above.

Preferably, also in the context of this method of the invention the phosphatidylinositol kinase is PIK3Ca, PIK3Cb, PIK4Ca, PIP5K2C, PIK3Cg, PIK3Cd, PIP5K2A, PIK4C2B, PIK3C3, PIP5K2B, PIK3C2b.

According to an especially preferred embodiment of this method of the invention, the kinase contains at least one mutation.

With respect to said one or more phosphatidylinositol kinases, the protein preparation containing said phosphatidylinositol kinases, the conditions for contacting with the immobilization product of the invention, the immobilization product of the invention, the complex between said phosphatidylinositol kinase and the immobilization product of the invention, the separation of phosphatidylinositol kinases from the immobilization product of the invention, and the detection of kinases or the determination of its amount, the embodiments as defined above for the identification methods of the invention also apply to the purification method of the invention.

The invention further relates to the use of the immobilization compound or the immobilization product of the invention for the identification of a phosphatidylinositol kinase interacting compound and for the purification of a phosphatidylinositol kinase. The embodiments as defined above also apply to the uses of the invention.

The invention further relates to a kit comprising the compound or the immobilization product of the invention. Such a kit is especially useful for performing the methods of the invention. Further components of the kit may be antibodies for the detection of kinase proteins, for example antibodies specific for phosphoinositide kinases. Such antibodies and their use are known in the art and they are commercially available (Sasaki et al., 2000, Nature 406, 897-902; Deora et al., 1998, J. Biol. Chem. 273, 29923-29928). Furthermore, the kit may contain further auxiliary components like buffers, means for the detection of antibodies, and positive controls. Such components are known in the art.

The invention is further illustrated by the following figures and examples, which are not considered as being limiting for the scope of protection conferred by the claims of the present application. In case where in the following examples the term "affinity matrix" is used, this term refers to an immobilization product as defined in the present application.

SHORT DESCRIPTION OF THE FIGURES

FIG. 1: Methods used in the synthesis of immobilization compounds as described in example 1.

Figure 2:
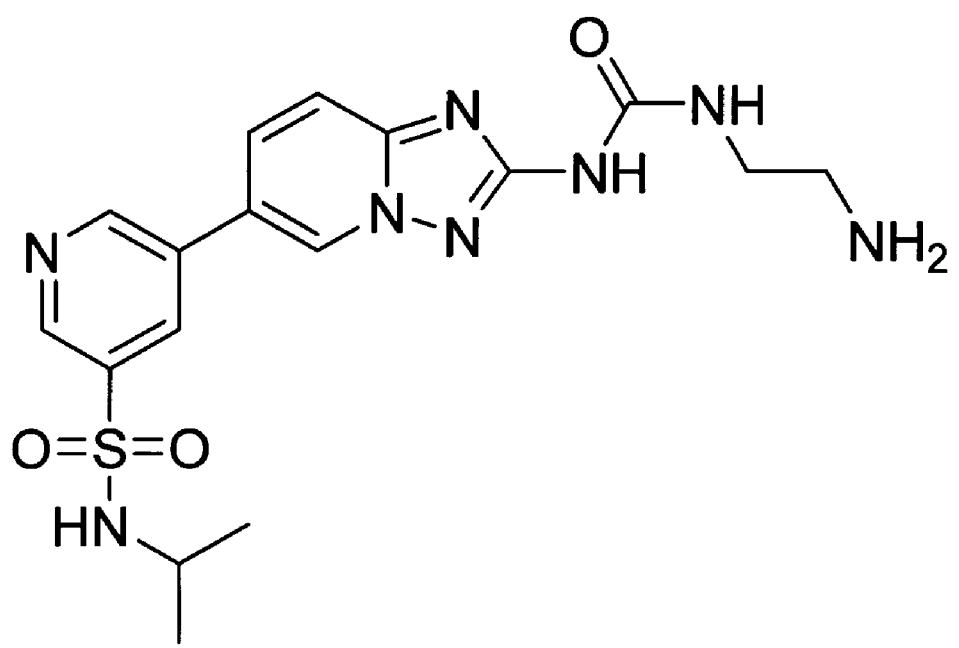

FIG. 2: Structure of 5-(2-(3-(2-aminoethyl)ureido)-[1,2,4]triazolo[1,5-a]pyridin-6-yl)-N-isopropylpyridine-3-sulfonamide (CZC00031207).

Figure 3:
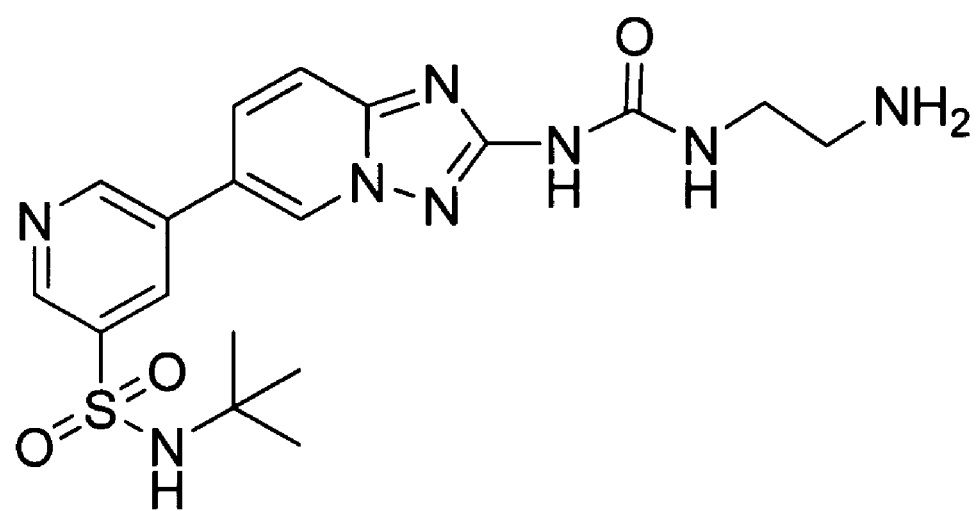

FIG. 3: Structure of 5-(2-(3-(2-aminoethyl)ureido)-[1,2,4]triazolo[1,5-a]pyridin-6-yl)-N-tert-butylpyridine-3-sulfonamide (CZC00025236).

Figure 4:
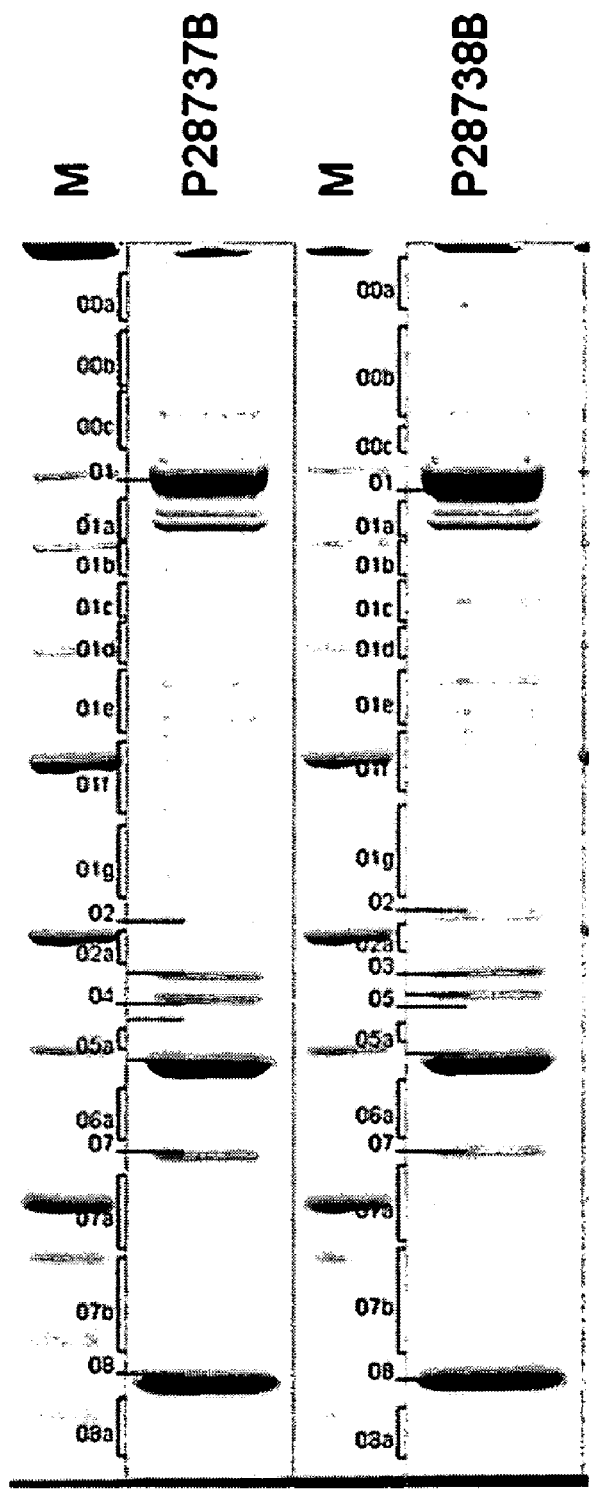

FIG. 4: Kinobeads experiment with the immobilized compound CZC31207 for mass spectrometry analysis of captured proteins.

A protein gel after staining with Coomassie brilliant blue is shown. The experiment was performed as described in example 2 with a mix of HeLa and placenta cell lysates. Proteins bound to the affinity matrix were eluted with SDS sample buffer and separated by SDS-polyacrylamide gel electrophoresis. The indicated gel areas were cut out as gel slices, proteins were treated with trypsin and ITRAQ-labeled peptides were analysed by mass spectrometry. Left lane (P28737B): cell lysate treated with 10 µM free compound CZC31207; middle lane: protein molecular weight marker; right lane (P28738B): DMSO control.

Figure 5:
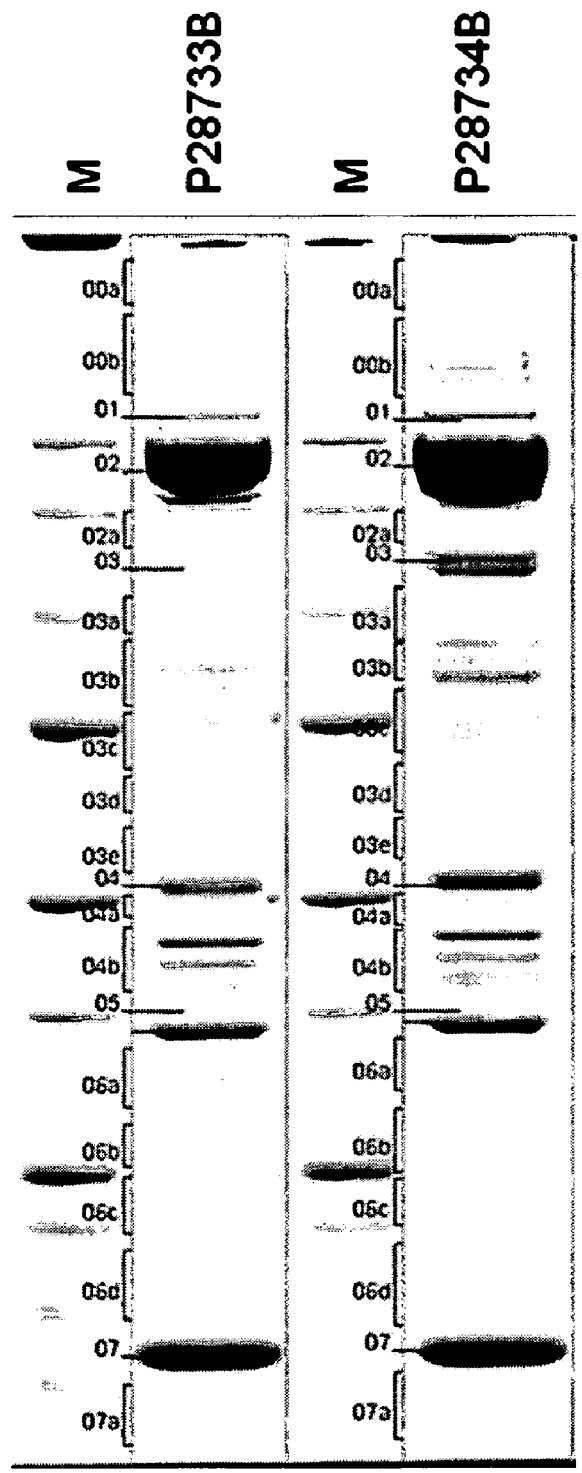

FIG. 5: Kinobeads experiment with the immobilized compound CZC31207 for mass spectrometry analysis of captured proteins.

A protein gel after staining with Coomassie brilliant blue is shown. The experiment was performed as described in example 3 with a mix of Jurkat and Ramos cell lysates. Proteins bound to the affinity matrix were eluted with SDS sample buffer and separated by SDS-polyacrylamide gel electrophoresis. The indicated gel areas were cut out as gel slices, proteins were treated with trypsin and ITRAQ-labeled peptides were analysed by mass spectrometry. Left lane (P28733B): cell lysate treated with 10 µM free compound CZC31207; middle lane: protein molecular weight marker; right lane (P28734B): DMSO control.

Figure 6:
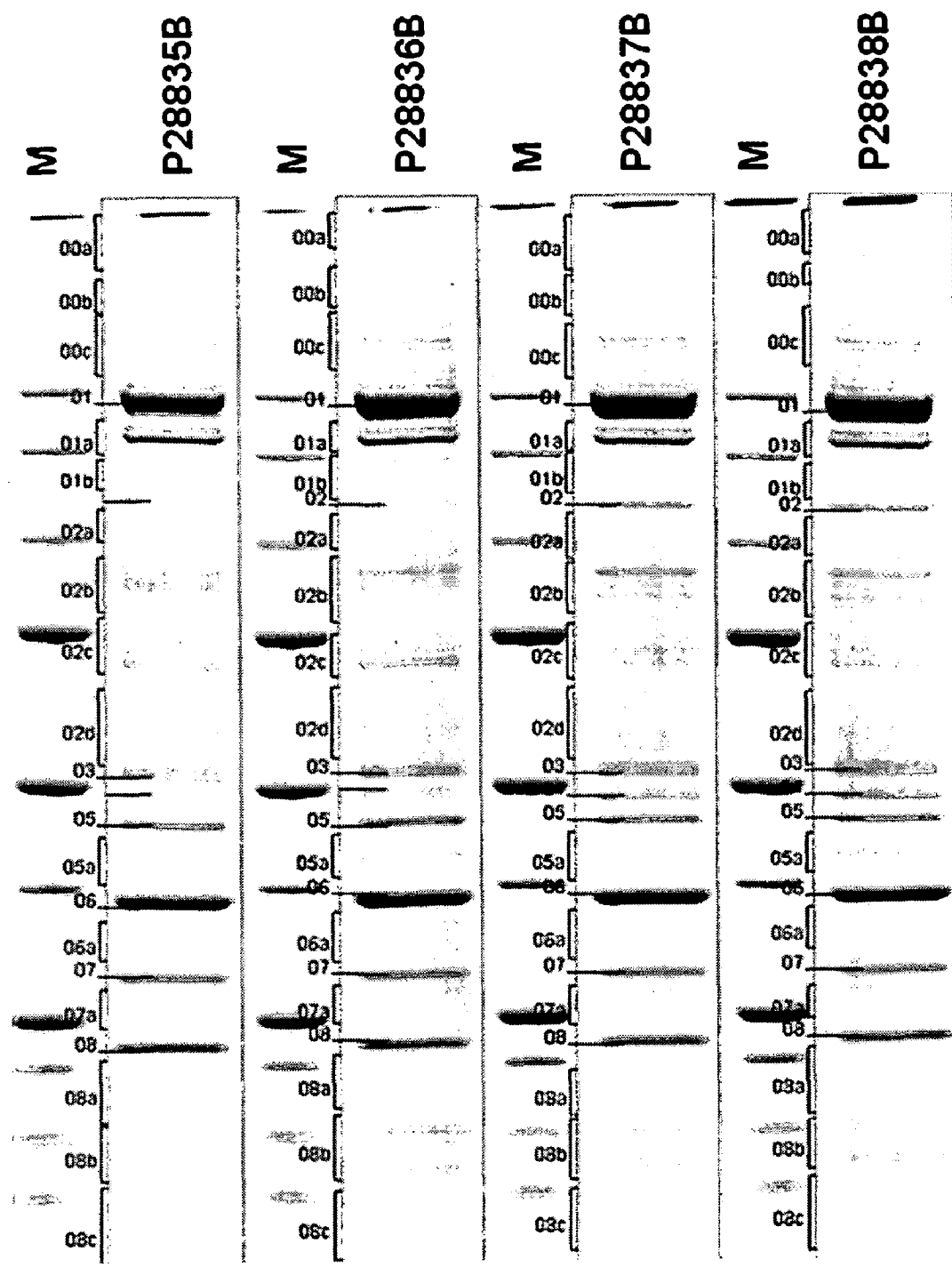

FIG. 6: Selectivity profiling experiment for test compound CZC00024513 using CZC00025236 as a capture compound.

A protein gel after staining with Coomassie brilliant blue is shown. The experiment was performed as described in example 4 with a mix of HeLa and placenta cell lysates. Proteins bound to the affinity matrix were eluted with SDS sample buffer and separated by SDS-polyacrylamide gel electrophoresis. The indicated gel areas were cut out as gel slices, proteins were treated with trypsin and ITRAQ-labeled peptides were analysed by mass spectrometry.

First lane (P28835B): cell lysate treated with 10 µM of test compound CZC00024513;
Second lane (P28836B): cell lysate treated with 1 µM of test compound CZC00024513;
Third lane (P28837B): cell lysate treated with 0.1 µM of test compound CZC00024513;
Fourth lane (P28838B): cell lysate treated 0.5% DMSO.
M: protein molecular weight marker.

Figure 7:
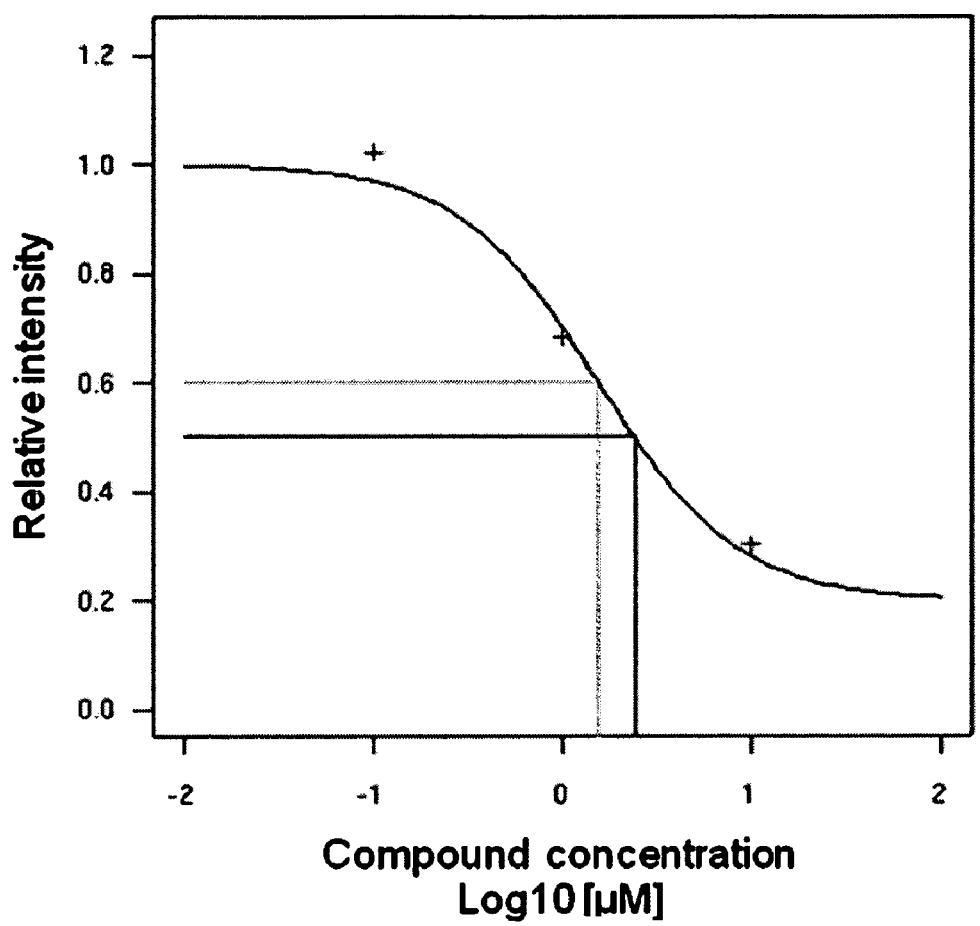

FIG. 7: Dose response curve for PI3Kalpha (PIK3CA; $IC_{50}$=1.55 µM)

Figure 8:
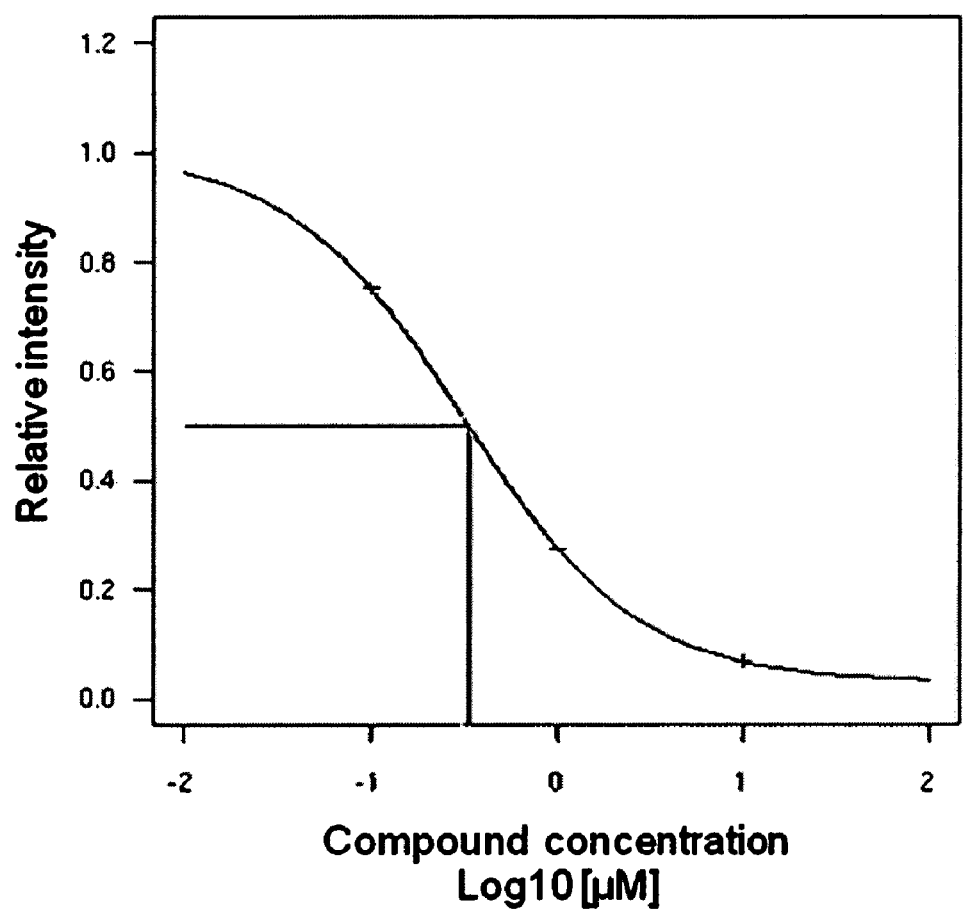

FIG. 8: Dose response curve for PI3 Kbeta (PIK3CB; $IC_{50}$=0.31 µM)

Figure 9:
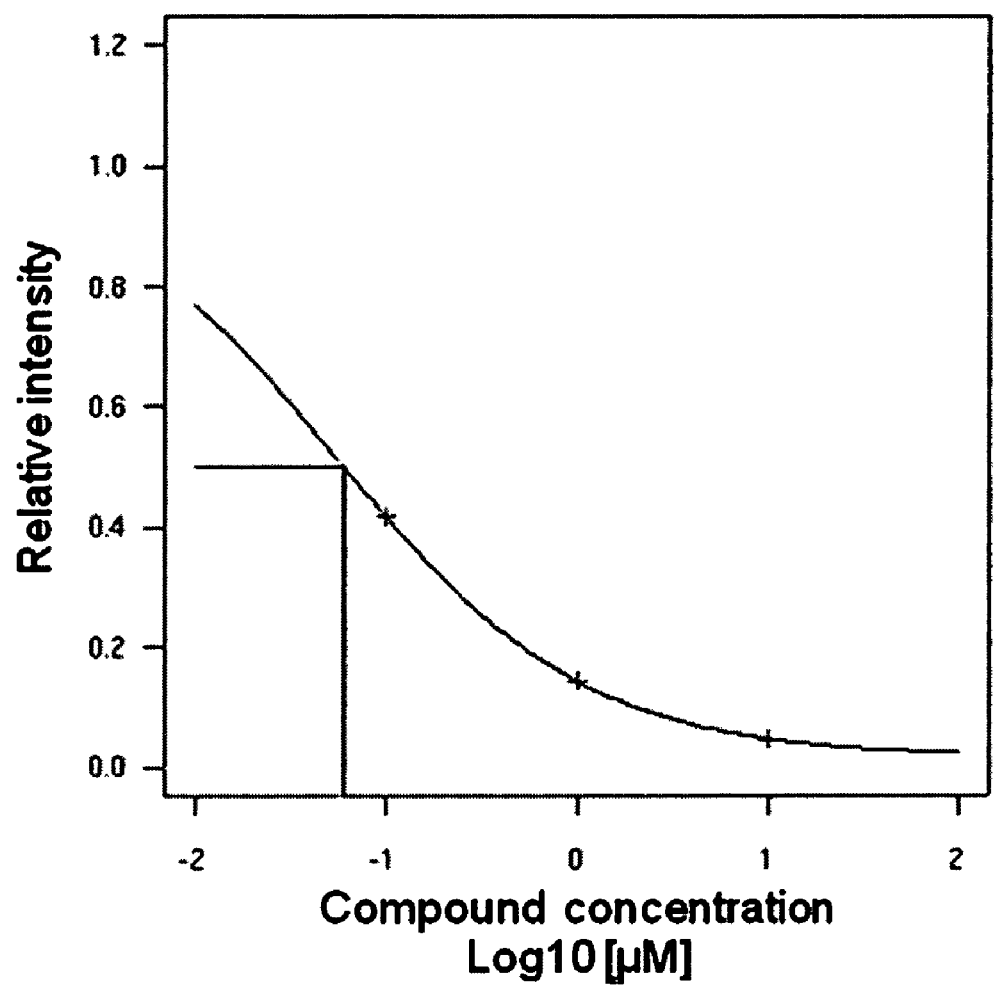

FIG. 9: Dose response curve for PI3 Kgamma (PIK3CG; $IC_{50}$=0.06 µM)

Figure 10:
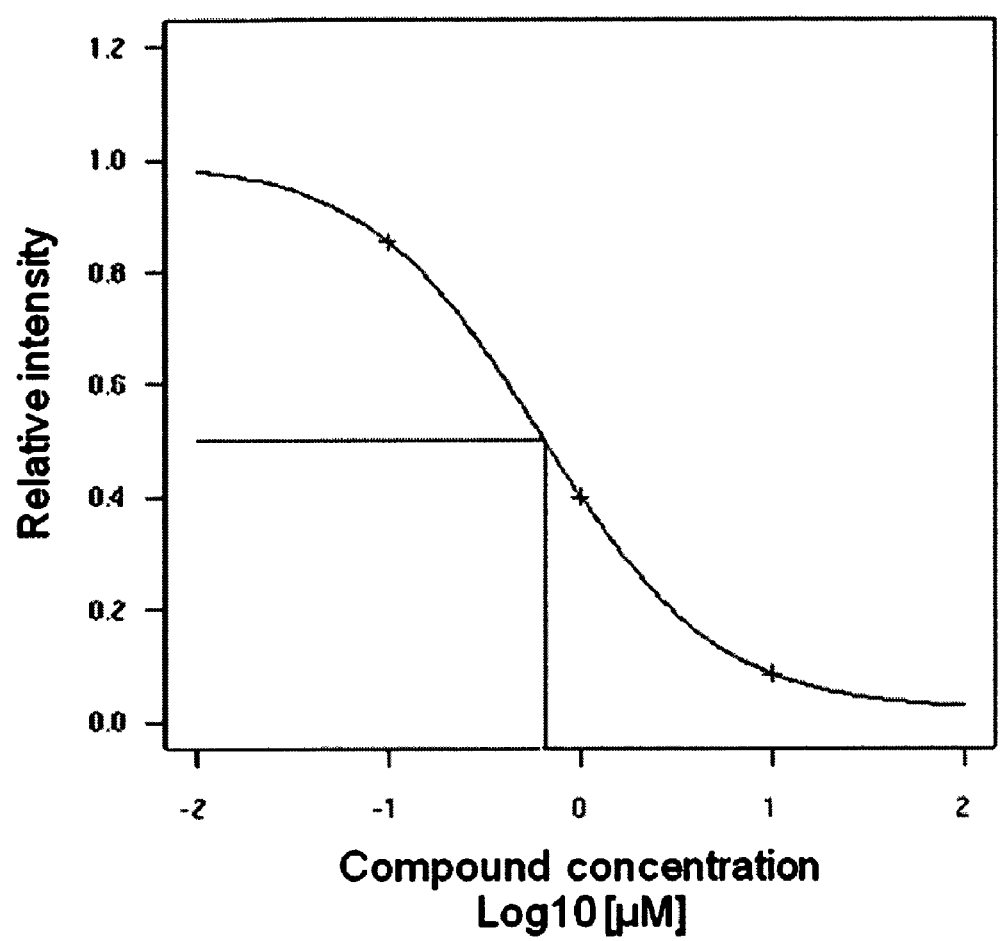

FIG. 10: Dose response curve for PI3 Kdelta (PIK3CD; $IC_{50}$=0.62 µM)

FIG. 11: Amino acid sequence of human PIK3CA (IPI0031386.2). Peptides identified by mass spectrometry are underlined (HeLa Placenta experiment, P28738B)

FIG. 12: Amino acid sequence of human PIK3CB (IPI00031388.1). Peptides identified by mass spectrometry are underlined (HeLa Placenta experiment, P28738B)

FIG. 13: Amino acid sequence of human PIK4Ca (IPI00070943.3). Peptides identified by mass spectrometry are underlined (HeLa Placenta experiment, P28738B)

FIG. 14: Amino acid sequence of human PIP5K2C (IPI00152303.7). Peptides identified by mass spectrometry are underlined (HeLa Placenta experiment, P28738B)

FIG. 15: Amino acid sequence of human PIK3Cg (IPI00292690.1). Peptides identified by mass spectrometry are underlined (HeLa Placenta experiment, P28738B)

FIG. 16: Amino acid sequence of human PIK3Cd (IPI00298410.2). Peptides identified by mass spectrometry are underlined (HeLa Placenta experiment, P28738B)

EXAMPLES

Example 1

Preparation of the Affinity Matrix

This example describes the synthesis of compounds and methods for their immobilization on a solid support yielding the affinity matrix used in the following examples for the capturing of kinases from cell lysates.

Analytical Methods

NMR spectra were obtained on a Brucker dpx400.

LCMS was carried out on an Agilent 1100 using a Gemini C18, 3×30 mm, 3 microns column. Column flow was 1.2 mL/min. and solvents used were water and acetonitrile (0.1% formic acid) with an injection volume of 3 or 10 ul. Wavelengths were 254 and 210 nm.

TABLE 1

| Chromatography | | |
|---|---|---|
| Time (min) | Water | Acetonitrile |
| 0 | 95 | 5 |
| 3 | 5 | 95 |
| 4.5 | 5 | 95 |
| 4.6 | 95 | 5 |
| 5.00 | | STOP |

Synthesis of Compounds 1-(5-Bromo-pyridin-2-yl)-3-carboethoxy-thiourea

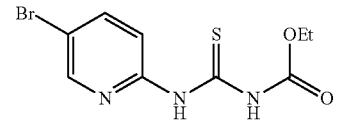 [SMILES: CCOC(=O)NC(=S)Nc1ccc(Br)cn1]

To a solution of 2-amino-5-bromopyridine (200.0 g, 1.156 mol) in DCM (2.0 L) cooled to 5° C. was added ethoxycarbonyl isothiocyanate (134.9 mL, 1.156 mol) dropwise over 15 min. The reaction mixture was then allowed to warm to room temperature (20° C.) and stirred for 16 h. Evaporation in vacuo gave a yellow solid which was collected by filtration, thoroughly washed with petrol (3×500 mL) and air-dried to afford the title compound (351.5 g, quantitative). No further purification was required.

¹H NMR (d₆-DMSO) δ 12.22 (br s, 1H), 11.75 (br s, 1H), 8.66 (br s, 1H), 8.57 (d, 1H), 8.16 (dd, 1H), 4.26 (q, 2H), 1.28 (t, 3H).

LCMS, (M+H⁺) 304/406, Rt=2.84 min.

6-Bromo-[1,2,4]triazolo[1,5-a]pyridin-2-ylamine (A)

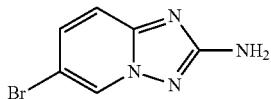 [SMILES: Nc1nc2ccc(Br)cn2n1]

To a suspension of hydroxylamine hydrochloride (409.2 g, 5.888 mol) in EtOH/MeOH (1:1, 2.5 L) was added N,N-diisopropylethylamine (606.1 mL, 3.480 mol), the mixture was stirred at room temperature (20° C.) for 1 h. 1-(6-Bromopyridin-2-yl)-3-carboethoxy-thiourea (352.8 g, 1.160 mol) was then added and the mixture slowly heated to reflux (Note: bleach scrubber required to quench H₂S evolved). After 2 h at reflux the mixture was allowed to cool and filtered to collect the precipitated solid. The collected solid was washed successively with water (1.0 L), EtOH/MeOH (1:1, 1.0 L) and diethyl ether (500 mL) then air-dried to afford the title compound as a white solid (169.2 g, 69%). No further purification was required.

¹H NMR (d₆-DMSO) δ 8.94 (d, 1H), 7.58 (dd, 1H), 7.36 (d, 1H), 6.16 (br s, 2H).

LCMS (M+H⁺) 213/214, Rt=1.45 min.

Method 1 Synthesis of Sulfonamides 5-bromo-N-tert-butylpyridine-3-sulfonamide

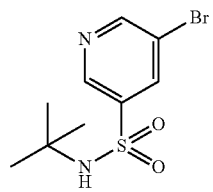

To a solution of 5-bromopyridine-3-sulfonyl chloride (5 g, 17 mmol) in pyridine (10 mL) at 0° C. was added tert-butylamine (3.6 mL, 2 equiv., 34 mmol). The reaction mixture was allowed to warm to room temperature and then heated to 40° C. for 14 h. After this time the crude reaction mixture was again cooled to 0° C. and diluted with dilute HCl (0.05M, 40 mL). The reaction was stirred at 0° C. for 30 min and the resulting precipitate collected by filtration. The solid was washed with water and dried to afford the title compound as a yellow solid (2.12 g, 7.3 mmol, 42%). No further purification was required.

LCMS (method A) (M+H⁺) 292/294, Rt=2.41 min 5-bromo-N-isopropylpyridine-3-sulfonamide

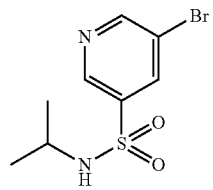

Prepared according to Method 1 using isopropylamine.

LCMS (method A) (M+H⁺) 281/283, Rt=2.28 min

Method 2 Suzuki Coupling 5-(2-Amino-[1,2,4]triazolo[1,5-a]pyridin-6-yl)-pyridine-3-sulfonic acid tert-butylamide

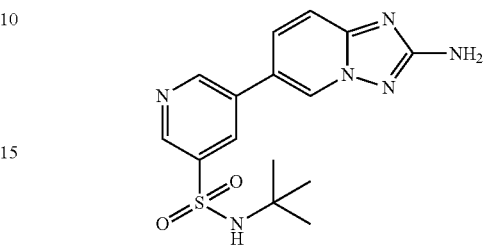

5-bromo-N-tert-butylpyridine-3-sulfonamide (375 mg, 0.986 mmol), bis(pinacolato) diboron (276 mg, 1.085 mmol), potassium acetate (290 mg, 2.96 mmol), [1,1'bis(diphenylphosphino)ferrocene]dichloro-palladium (II) complex with CH₂Cl₂ (40 mg, 0.049 mmol) and dioxane (3 ml) were heated to 120° C. for 60 minutes in the microwave. After this time aryl bromide (A) (147 mg, 0.69 mmol), Na₂CO₃ (2M aqueous solution, 2 mL), EtOH (0.4 ml) and a further portion of [1,1'bis(diphenylphosphino)ferrocene]dichloro-palladium (II) complex with CH₂Cl₂ was added and reaction mixture heated further for 60 minutes at 120° C. in the microwave. After this time the solvents were removed in vacuo and the brown residue redissolved in 2M HCl (30 mL), the aqueous phase was washed with ethyl acetate (3×20 mL) and then neutralized with concentrated NaOH to pH 7.0. The aqueous phase was then extracted with ethyl acetate (3×20 mL), the organic extracts were combined, dried over sodium sulfate, filtered and the solvent removed in vacuo to afford the desired product as a brown solid (441 mg, 54%).

LCMS, (M+H⁺) 347, RT=1.89 min.

5-(2-amino-[1,2,4]triazolo[1,5-a]pyridin-6-yl)-N-isopropylpyridine-3-sulfonamide

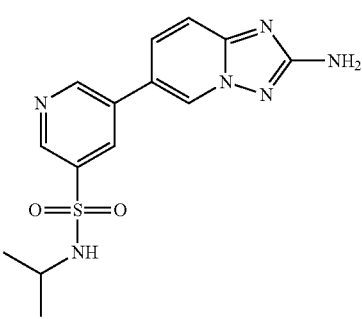 [SMILES: CC(C)NS(=O)(=O)c1cncc(-c2ccc3nc(N)nn3c2)c1]

Prepared according to method 2
LCMS, (M+H⁺) 333, Rt=1.86 min
Method 3 Synthesis of Ureas tert-butyl 2-(3-(6-(5-(N-tert-butylsulfamoyl)pyridin-3-yl)-[1,2,4]triazolo[1,5-a]pyridin-2-yl)ureido)ethyl-carbamate

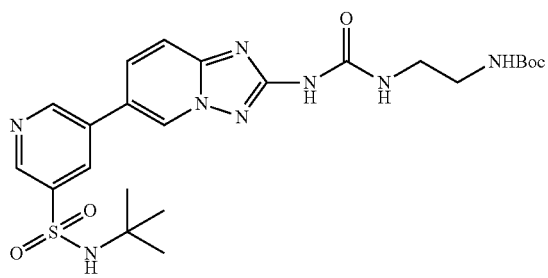 [SMILES: CC(C)(C)NS(=O)(=O)c1cncc(-c2ccc3nc(NC(=O)NCCNC(=O)OC(C)(C)C)nn3c2)c1]

5-(2-Amino-[1,2,4]triazolo[1,5-a]pyridin-6-yl)-pyridine-3-sulfonic acid tert-butylamide (50 mg, 0.14 mmol) was suspended in tetrahydrofuran:pyridine (30 mL, 5:1) and cooled to 0° C. Triphosgene (41 mg, 0.14 mmol) was added in one portion and the reaction mixture heated at 35° C. for 2 hours. After this time the solvent was decanted and the resultant semi-solid dissolved in DMF:pyridine (1 mL, 10:1), N-Boc-ethylenediamine (50 mg, 0.32 mmol) was added in one portion and the reaction mixture heated for 18 hours at 65° C. The desired product was isolated as a white solid, directly from the reaction mixture, by preparative HPLC (35 mg)
LCMS, (M+H⁺) 533, RT=1.66 min.

tert-butyl 2-(3-(6-(5-(N-isopropylsulfamoyl)pyridin-3-yl)-[1,2,4]triazolo[1,5-a]pyridin-2-yl)ureido)ethyl-carbamate

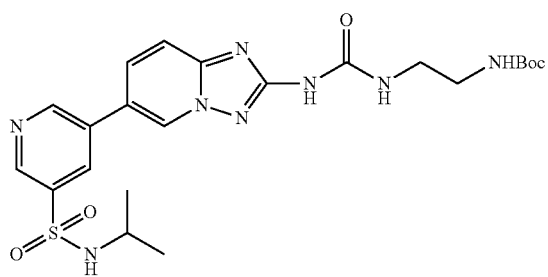 [SMILES: CC(C)NS(=O)(=O)c1cncc(-c2ccc3nc(NC(=O)NCCNC(=O)OC(C)(C)C)nn3c2)c1]

Prepared according to method 3. LCMS, (M+H⁺) 519, Rt=1.59 min.
Method 4 Boc Deprotection 5-(2-(3-(2-aminoethyl)ureido)-[1,2,4]triazolo[1,5-a]pyridin-6-yl)-N-tert-butylpyridine-3-sulfonamide

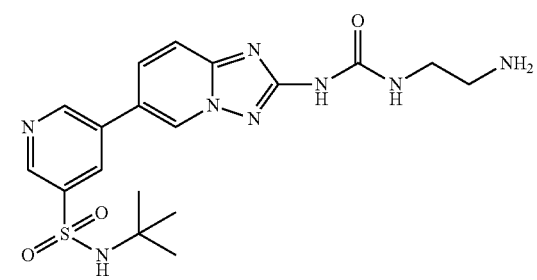 [SMILES: CC(C)(C)NS(=O)(=O)c1cncc(-c2ccc3nc(NC(=O)NCCN)nn3c2)c1]

tert-butyl 2-(3-(6-(5-(N-tert-butylsulfamoyl)pyridin-3-yl)-[1,2,4]triazolo[1,5-a]pyridin-2-yl)ureido)ethylcarbamate (35 mg) was suspended in HCl (4M in dioxane, 2 mL) and DCM (2 mL) and the reaction mixture stirred overnight at room temperature. After this time the reaction mixture was pippeted slowly onto diethyl ether at −78° C. and maintained at this temperature for 20 minutes. The resultant white solid was filtered, washed with further diethyl ether and dried under vacuum to afford the title compound (21 mg).
¹H NMR δ (d₆-DMSO) δ 10.27 (s, 1H), 9.42 (d, 1H), 9.23 (d, 1H), 9.01 (d, 1H), 8.59 (t, 1H), 8.37 (t, 1H), 8.10 (dd, 1H), 7.99-7.92 (m, 2H), 7.86 (s, 1H), 7.83 (d, 1H), 7.35 (s, 1H), 7.23 (s, 1H), 7.10 (s, 1H), 3.50 (q, 2H), 3.0-2.96 (m, 2H), 1.16 (s, 9H).
LCMS, (M+H⁺) 433, Rt=1.60 min.

5-(2-(3-(2-aminoethyl)ureido)-[1,2,4]triazolo[1,5-a]pyridin-6-yl)-N-isopropylpyridine-3-sulfonamide

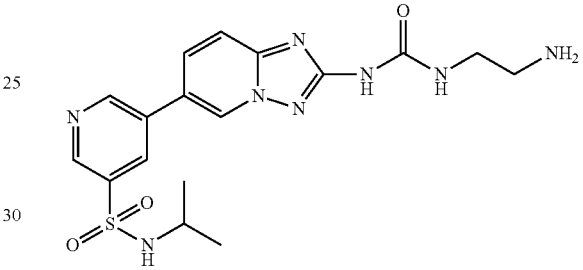

Prepared according to method 4
¹H NMR δ (d₆-DMSO) δ 10.30 (s, 1H), 9.43 (d, 1H), 9.25 (d, 1H), 8.99 (d, 1H), 8.56 (t, 1H), 8.36 (t, 1H), 8.12 (dd, 1H), 7.96-7.93 (m, 3H), 7.82 (d, 1H), 3.50 (q, 2H), 3.41 (septet, 1H), 2.98 (q, 2H), 0.99 (d, 6H). LCMS, (M+H⁺) 419, Rt=1.50 min.

TABLE 2

| Abbreviations | |
|---|---|
| Boc | tert-butoxycarbonyl |
| DCM | Dichloromethane |
| DMSO | dimethylsulfoxide |
| MeOH | Methanol |
| EtOH | Ethanol |
| ⁱPr₂NEt | Diisopropylethylamine |
| NH₂OH•HCl | hydroxylaminehydrochloride |
| Pd(dppf)(Cl)₂ | [1,1'bis(diphenylphosphino)ferrocene] dichloro-palladium (II) |
| DMF | N,N-Dimethylformamide |
| THF | tetrahydrofuran |
| s | singlet |
| d | Doublet |
| dd | Doubledoublet |
| br | Broad |
| mL | millilitres |
| L | litre |
| t | Triplet |
| m | Multiplet |
| Rt | Retention time |

Immobilization of Compounds on Beads (Affinity Matrix)
NHS-activated Sepharose 4 Fast Flow (Amersham Biosciences, 17-0906-01) was equilibrated with anhydrous DMSO (Dimethylsulfoxid, Fluka, 41648, H20<=0.005%). 1 ml of settled beads was placed in a 15 ml Falcon tube, compound stock solution (usually 100 mM in DMF or DMSO) was added (final concentration 0.2-2 μmol/ml beads) as well as 15 µl of triethylamine (Sigma, T-0886, 99% pure). Beads were incubated at room temperature in darkness on an end-over-end shaker (Roto Shake Genie, Scientific Industries Inc.) for 16-20 hours. Coupling efficiency is determined by HPLC. Non-reacted NHS-groups were blocked by incubation with aminoethanol at room temperature on the end-over-end shaker over night. Beads were washed with 10 ml of DMSO and were stored in isopropanol at −20° C. These beads were used as the affinity matrix in the following examples. Control beads (no compound immobilized) were generated by blocking the NHS-groups by incubation with aminoethanol as described above.

Example 2

Kinobeads Experiment Using Immobilized Compound CZC31207 and a Mix of HeLa and Placenta Cell Lysates This example demonstrates the use of an immobilized compound (structure shown in FIG. 2, CZC31207) for the capturing and identification of phosphatidylinositol kinases from cell lysate in a competition binding assay. To the first aliquot of cell lysate 10 µM of the free compound (CZC31207) was added and allowed to bind to proteins in the lysate. Then the affinity matrix with the immobilized compound (Example 1) was added to capture proteins that were not interacting with the previously added free compound. Beads were separated from the lysate and bead bound proteins were eluted in SDS sample buffer and subsequently separated by SDS-Polyacrylamide gel electrophoresis (FIG. 4). Suitable gel bands were cut out and subjected to in-gel proteolytic digestion with trypsin. The second lysate aliquot was processed identically, however no free compound was added (DMSO solvent control). Peptides originating from samples 1 and 2 were labeled with iTRAQ reagents (iTRAQ 115 and iTRAQ 117) and the combined samples were analyzed with a nano-flow liquid chromatography system coupled online to a tandem mass spectrometer (LC-MS/MS) experiment followed by iTRAQ reporter ion quantification in the MS/MS spectra (Ross et al., 2004. Mol. Cell. Proteomics 3(12):1154-1169). Further experimental protocols can be found in WO2006/134056 and a previous publication (Bantscheff et al., 2007. Nature Biotechnology 25, 1035-1044).

The identified kinases are shown in Table 4 including the percent competition values for the sample to which 10 µM free compound had been added. In total 18 different kinases were identified and competed by different degrees. For illustration, the identified peptides for PIK3Ca, PIK3Cb, PIK4Ca, PIP5K2C, PIK3Cg and PIK3Cd are shown in FIGS. 11 to 16. Sequence identifiers are defined by the International Protein Index (IPI) (Kersey et al., 2004. Proteomics 4(7): 1985-1988).

1. Cell Culture

In this example a mix of HeLa and placenta cell lysates was used (Bantscheff et al., 2007. Nature Biotechnology 25, 1035-1044). HeLa cells (American Type Culture Collection-No CCL-2) were either obtained from an external supplier (CIL SA, Mons, Belgium) or grown in one litre Spinner flasks (Integra Biosciences, #182101) in suspension in RPMI 1640 medium (Invitrogen, #21875-034) supplemented with 10% Fetal Bovine Serum (Invitrogen, #10270-106). Cells were harvested by centrifugation, washed once with 1×PBS buffer (Invitrogen, #14190-094) and cell pellets were frozen in liquid nitrogen and subsequently stored at −80° C.

2. Preparation of Cell Lysates

Cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1 873 580) per 25 ml buffer was added. The material was dounced 20 times using a mechanized POTTER S, transferred to 50 ml falcon tubes, incubated for 30 minutes rotating at 4° C. and spun down for 10 minutes at 20,000×g at 4° C. (10,000 rpm in Sorvall SLA600, precooled). The supernatant was transferred to an ultracentrifuge (UZ)-polycarbonate tube (Beckmann, 355654) and spun for 1 hour at 145.000×g at 4° C. (40.000 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

3. Capturing of Kinases from Cell Lysate

Sepharose-beads with the immobilized compound (100 µl beads per pull-down experiment) were equilibrated in lysis buffer and incubated with a cell lysate sample containing 50 mg of protein on an end-over-end shaker (Roto Shake Genie, Scientific Industries Inc.) for 2 hours at 4° C. Beads were collected, transferred to Mobicol-columns (MoBiTech 10055) and washed with 10 ml lysis buffer containing 0.4% NP40 detergent, followed by 5 ml lysis buffer containing 0.2% detergent. To elute bound proteins, 60 µl 2×SDS sample buffer was added to the column. The column was incubated for 30 minutes at 50° C. and the eluate was transferred to a siliconized microfuge tube by centrifugation. Proteins were then alkylated with 108 mM iodoacetamid. Proteins were then separated by SDS-Polyacrylamide electrophoresis (SDS-PAGE).

4. Protein Identification by Mass Spectrometry 4.1 Protein Digestion Prior to Mass Spectrometric Analysis Gel-separated proteins were digested in-gel essentially following a previously described procedure (Shevchenko et al., 1996, Anal. Chem. 68:850-858). Briefly, gel-separated proteins were excised from the gel using a clean scalpel, destained twice using 100 µl 5 mM triethylammonium bicarbonate buffer (TEAB; Sigma T7408) and 40% ethanol in water and dehydrated with absolute ethanol. Proteins were subsequently digested in-gel with porcine trypsin (Promega) at a protease concentration of 10 ng/µl in 5 mM TEAB. Digestion was allowed to proceed for 4 hours at 37° C. and the reaction was subsequently stopped using 5 µl 5% formic acid.

4.2 Sample Preparation Prior to Analysis by Mass Spectrometry

Gel plugs were extracted twice with 20 µl 1% formic acid and three times with increasing concentrations of acetonitrile. Extracts were subsequently pooled with acidified digest supernatants and dried in a vacuum centrifuge.

4.3 iTRAQ Labeling of Peptide Extracts

The peptide extracts of samples treated with 10 µM of free compound (CZC31326) and the solvent control (0.5% DMSO) were treated with different variants of the isobaric tagging reagent (iTRAQ Reagents Multiplex Kit, part number 4352135, Applied Biosystems, Foster City, Calif., USA). The iTRAQ reagents are a set of multiplexed, amine-specific, stable isotope reagents that can label peptides on amino groups in up to four different biological samples enabling simultaneous identification and quantitation of peptides. The iTRAQ reagents were used according to instructions provided by the manufacturer. The samples were resuspended in 10 µl 50 mM TEAB solution, pH 8.5 and 10 µl ethanol were added. The iTRAQ reagent was dissolved in 120 µl ethanol and 10 μl of reagent solution were added to the sample. The labeling reaction was performed at room temperature for one hour on a horizontal shaker and stopped by adding 5 μl of 100 mM TEAB and 100 mM glycine in water. The two labeled sampled were then combined, dried in a vacuum centrifuge and resuspended in 10 μl of 0.1% formic acid in water.

4.4 Mass Spectrometric Data Acquisition

Peptide samples were injected into a nano LC system (CapLC, Waters or nano-LC 1D+, Eksigent) which was directly coupled either to a quadrupole TOF (QTOF Ultima, QTOF Micro, Waters), ion trap (LTQ) or Orbitrap mass spectrometer. Peptides were separated on the LC system using a gradient of aqueous and organic solvents (see below). Solvent A was 0.1% formic acid and solvent B was 70% acetonitrile in 0.1% formic acid.

TABLE 3

Peptides elution off the LC system

| Time (min) | % solvent A | % solvent B |
|---|---|---|
| 0 | 95 | 5 |
| 8.0 | 95 | 5 |
| 15 | 85 | 15 |
| 64.5 | 60 | 40 |
| 84.5 | 38 | 62 |
| 87 | 5 | 95 |
| 91 | 250 | 95 |
| 91.5 | 2095 | 5 |

4.5 Protein Identification

The peptide mass and fragmentation data generated in the LC-MS/MS experiments were used to query a protein data base consisting of an in-house curated version of the International Protein Index (IPI) protein sequence database combined with a decoy version of this database (Elias and Gygi, 2007, Target-decoy search strategy for increased confidence in large-scale protein identifications by mass spectrometry. Nature Methods 4, 207-214). Proteins were identified by correlating the measured peptide mass and fragmentation data with data computed from the entries in the database using the software tool Mascot (Matrix Science; Perkins et al., 1999. Probability-based protein identification by searching sequence databases using mass spectrometry data. Electrophoresis 20, 3551-3567). Search criteria varied depending on which mass spectrometer was used for the analysis. Protein acceptance thresholds were adjusted to achieve a false discovery rate of below 1% as suggested by hit rates on the decoy data base (Elias and Gygi, 2007, Target-decoy search strategy for increased confidence in large-scale protein identifications by mass spectrometry. Nature Methods 4, 207-214).

4.6 Protein Quantitation

Relative protein quantitation was performed using peak areas of iTRAQ reporter ion signals essentially as described in an earlier publication (Bantscheff et al., 2007. Nature Biotechnology 25, 1035-1044).

TABLE 4

Identified kinases with compound CZC31207 from mixed HeLa and placenta cell lysates

| Representative Sequence | Kinase Name | Kinase Group | Quantified Spectra | Competition % |
|---|---|---|---|---|
| IPI00003479.3 | Erk2 | CMGC | 6 | −2.9 |
| IPI00021331.1 | NEK2 | Other | 5 | 40.4 |
| IPI00022633.3 | TNK1 | TK | 8 | −1.9 |
| IPI00031386.2 | PIK3Ca | Lipid Kinase | 7 | 68.6 |

TABLE 4-continued

Identified kinases with compound CZC31207 from mixed HeLa and placenta cell lysates

| Representative Sequence | Kinase Name | Kinase Group | Quantified Spectra | Competition % |
|---|---|---|---|---|
| IPI00031388.1 | PIK3Cb | Lipid Kinase | 67 | 85.6 |
| IPI00070943.3 | PIK4Ca | Lipid Kinase | 477 | 39.9 |
| IPI00152303.7 | PIP5K2C | Lipid Kinase | 57 | 78.3 |
| IPI00169392.5 | CaMK2g | CAMK | 8 | 15.2 |
| IPI00180781.3 | MLKL | TKL | 23 | 34.2 |
| IPI00292690.1 | PIK3Cg | Lipid Kinase | 28 | 80 |
| IPI00296337.2 | DNAPK | Atypical | 44 | 35.3 |
| IPI00298410.2 | PIK3Cd | Lipid Kinase | 57 | 83.6 |
| IPI00298612.1 | BCKDK | Atypical | 187 | 8 |
| IPI00298940.3 | AurA | Other | 4 | 12.8 |
| IPI00303550.2 | JNK2 | CMGC | 5 | 24.6 |
| IPI00418221.3 | MAP3K6 | STE | 3 | 10.3 |
| IPI00513678.1 | FRAP | Atypical | 33 | 25.9 |
| IPI00787127.1 | MAP3K1 | STE | 12 | 13.3 |

Example 3

Kinobeads Experiment Using Immobilized Compound CZC31207 and a Mix of Jurkat and Ramos Cell Lysates This example demonstrates the use of an immobilized compound (structure shown in FIG. 2, CZC31207) for the capturing and identification of kinases from amix of Jurkat and Ramos cell lysates in a competition binding assay. To the first aliquot of cell lysate 10 μM of the free compound CZC31207 was added and allowed to bind to proteins in the lysate. Then the affinity matrix with the immobilized compound was added to capture proteins that were not interacting with the previously added free compound. Beads were separated from the lysate and bead bound proteins were eluted in SDS sample buffer and subsequently separated by SDS-Polyacrylamide gel electrophoresis (FIG. 5). Suitable gel bands were cut out and subjected to in-gel proteolytic digestion with trypsin. The second lysate aliquot was processed identically, however no free compound was added (DMSO solvent control). Peptides originating from samples 1 and 2 were labeled with iTRAQ reagents (iTRAQ 114 and iTRAQ 116) and the combined samples were analyzed with a nano-flow liquid chromatography system coupled online to a tandem mass spectrometer (LC-MS/MS) experiment followed by iTRAQ reporter ion quantification in the MS/MS spectra as described in Example 2.

Jurkat cells (ATCC number T1B-152) and Ramos cells (ATCC number CRL-1596) were either obtained from an external supplier (CIL SA, Mons, Belgium) or grown in one litre Spinner flasks (Integra Biosciences, #182101) in suspension in RPMI 1640 medium (Invitrogen, #21875-034) supplemented with 10% Fetal Bovine Serum (Invitrogen, #10270-106) at a density between $0.2 \times 10^6$ and $1.0 \times 10^6$ cells/ml. Cells were harvested by centrifugation, washed once with 1×PBS buffer (Invitrogen, #14190-094) and cell pellets were frozen in liquid nitrogen and subsequently stored at −80° C.

The identified kinases are shown in Table 5 including the percent competition values for the sample to which 10 μM free compound had been added. In total of 20 different kinases were identified and competed by different degrees.

TABLE 5

Identified kinases with compound CZC31207 from a mix of Jurkat and Ramos cell lysates

| Representative Sequence | Kinase Name | Kinase Group | Quantified Spectra | Competition % |
|---|---|---|---|---|
| IPI00009334.4 | PKD2 | CAMK | 12 | 37.9 |
| IPI00009688.1 | PIP5K2A | Lipid Kinase | 8 | 68.5 |
| IPI00011488.4 | MST1 | STE | 4 | 24.5 |
| IPI00021331.1 | NEK2 | Other | 21 | 17 |
| IPI00023529.1 | CDK6 | CMGC | 4 | −1.6 |
| IPI00026689.4 | CDC2 | CMGC | 4 | 34.1 |
| IPI00031388.1 | PIK3Cb | Lipid Kinase | 48 | 94.8 |
| IPI00070943.3 | PIK4Ca | Lipid Kinase | 111 | 28.5 |
| IPI00152303.7 | PIP5K2C | Lipid Kinase | 23 | 75.5 |
| IPI00169392.5 | CaMK2g | CAMK | 58 | −3.1 |
| IPI00291068.3 | PIK4C2B | Lipid Kinase | 3 | 20.3 |
| IPI00292690.1 | PIK3Cg | Lipid Kinase | 273 | 91.5 |
| IPI00296337.2 | DNAPK | Atypical | 126 | 38.2 |
| IPI00298410.2 | PIK3Cd | Lipid Kinase | 160 | 91.3 |
| IPI00298612.1 | BCKDK | Atypical | 62 | −0.1 |
| IPI00299755.2 | PIK3C3 | Lipid Kinase | 9 | 52.4 |
| IPI00337426.1 | BIKE | Other | 90 | 26.1 |
| IPI00513678.1 | FRAP | Atypical | 5 | −87.1 |
| IPI00787127.1 | MAP3K1 | STE | 68 | 14.1 |
| IPI00828081.1 | CaMK2d | CAMK | 21 | −1.3 |

Example 4

Kinobeads Selectivity Profiling

This example illustrates the use of a competition binding assay in cell lysate to establish the kinase selectivity profile of the test compound CZC24513. This compound was added at defined concentrations (10 µM, 1 µM and 0.1 µM CZC24513) to a mix of HeLa and placenta cell lysates thereby allowing the test compound to bind to the target proteins in the lysate. Then the lysate was contacted with the immobilized compound CZC25236 to capture remaining free target proteins. The proteins bound to the immobilized compound were eluted with detergent-containing buffer, separated on a SDS-polyacrylamide gel and analyzed by mass spectrometry as described in example 2.

The peptide extracts corresponding to samples treated with different concentrations of the test compound (10 µM, 1 µM and 0.1 µM CZC24513) and the solvent control (0.5% DMSO) were treated with different variants of the isobaric tagging reagent (iTRAQ Reagents Multiplex Kit, part number 4352135, Applied Biosystems, Foster City, Calif., USA). The iTRAQ reagents are a set of multiplexed, amine-specific, stable isotope reagents that can label peptides in up to four different biological samples enabling simultaneous identification and quantitation of peptides. The iTRAQ reagents were used according to instructions provided by the manufacturer.

The test compound CZC24513 was used at three different concentrations in the cell lysate and the $IC_{50}$ values were normalized to the DMSO control. For selected kinases the $IC_{50}$ values were plotted against the concentration of CZC24513 and curve fitting was performed using the Xlfit program (ID Business Solutions Ltd.) as previously described. (Bantscheff et al., 2007. Nature Biotechnology 25, 1035-1044). The $IC_{50}$ value corresponds to the test compound concentration at which the relative intensity of the MS signal for a kinase is 50% compared to the solvent (DMSO) control. Examples of dose response curves for individual kinases are shown in FIGS. 7 to 10.

TABLE 6

Selectivity profiling of test compound CZC24513

| Representative Sequence | Kinase Name | Kinase Group | Quantified Spectra | $IC_{50}$ (µM) |
|---|---|---|---|---|
| IPI00003479.3 | Erk2 | CMGC | 5 | 10 |
| IPI00009688.1 | PIP5K2A | Lipid Kinase | 11 | 0.61 |
| IPI00022633.3 | TNK1 | TK | 9 | 10 |
| IPI00024006.3 | PIK3R4 | Other | 2 | 6.01 |
| IPI00031386.2 | PIK3Ca | Lipid Kinase | 10 | 1.55 |
| IPI00031388.1 | PIK3Cb | Lipid Kinase | 104 | 0.31 |
| IPI00070943.3 | PIK4Ca | Lipid Kinase | 593 | 2.26 |
| IPI00152303.7 | PIP5K2C | Lipid Kinase | 78 | 0.75 |
| IPI00216470.1 | PIP5K2B | Lipid Kinase | 1 | 0.27 |
| IPI00292056.4 | PIK3C2b | Lipid Kinase | 46 | 0.99 |
| IPI00292690.1 | PIK3Cg | Lipid Kinase | 18 | 0.1 |
| IPI00296337.2 | DNAPK | Atypical | 148 | 3.04 |
| IPI00298410.2 | PIK3Cd | Lipid Kinase | 50 | 0.62 |
| IPI00337426.1 | BIKE | Other | 30 | 10 |
| IPI00479760.6 | AAK1 | Other | 7 | 4.31 |
| IPI00513678.1 | FRAP | Atypical | 22 | 10 |
| IPI00787127.1 | MAP3K1 | STE | 5 | 10 |

TABLE 7

Preparation of 5x-DP buffer

| Substance: | Stock solution | Final conc. in 1x lysis buffer | Add for 11 5x lysis buffer |
|---|---|---|---|
| Tris/HCl pH 7.5 | 1M | 50 mM | 250 ml |
| Glycerol | 87% | 5% | 288 ml |
| $MgCl_2$ | 1M | 1.5 mM | 7.5 ml |
| NaCl | 5M | 150 mM | 150 ml |
| $Na_3VO_4$ | 100 mM | 1 mM | 50 ml |

The 5x-DP buffer was filtered through a 0.22 µm filter and stored in 40 ml-aliquots at −80° C. Stock solutions were obtained from the following suppliers: 1.0 M Tris/HCl pH 7.5 (Sigma, T-2663), 87% Glycerol (Merck, catalogue number 04091.2500); 1.0 M $MgCl_2$ (Sigma, M-1028); 5.0 M NaCl (Sigma, S-5150).

The invention claimed is:

1. An immobilization compound of formula (I)

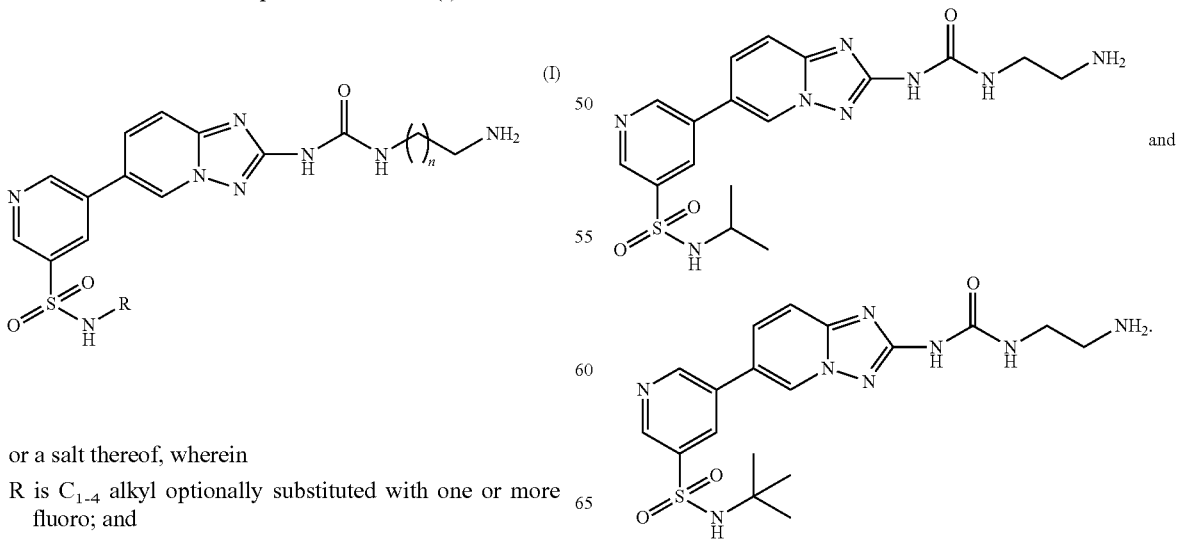

or a salt thereof, wherein

R is $C_{1-4}$ alkyl optionally substituted with one or more fluoro; and n is 1, 2, or 3.

2. The immobilization compound of claim 1, selected from the group consisting of 3. A method for the preparation of an immobilization product, said method comprising immobilizing the immobilization compound of claim 1 to a solid support by a covalent direct or linker mediated attachment.

4. The method of claim 3, wherein the solid support is selected from the group consisting of agarose, modified agarose, sepharose beads latex, cellulose, and ferro- or ferrimagnetic particles.

5. An immobilization product, comprising the immobilization compound of claim 1 immobilized on a solid support.

6. A method for the identification of a phosphatidylinositol kinase interacting compound, comprising the steps of
   a) providing a protein preparation containing a variety of phosphatidylinositol kinases,
   b) contacting the protein preparation with the immobilization product of claim 5 and with a given compound under conditions allowing the formation of one or more different complexes between one of the phosphatidylinositol kinases and the immobilization product, and
   c) detecting the complex or the complexes formed in step b).

7. A method for the identification of a phosphatidylinositol kinase interacting compound, comprising the steps of:
   a) providing two aliquots of a protein preparation containing a variety of phosphatidylinositol kinases,
   b) contacting one aliquot with the immobilization product of claim 5 under conditions allowing the formation of one or more different complexes between one of the phosphatidylinositol kinases and the immobilization product,
   c) contacting the other aliquot with the immobilization product of claim 5 and with a given compound under conditions allowing the formation of one or more different complexes between one of the phosphatidylinositol kinases and the immobilization product, and
   d) determining the amount of the complex or the complexes formed in steps b) and c).

8. A method for the identification of a phosphatidylinositol kinase interacting compound, comprising the steps of:
   a) providing two aliquots of a cell preparation comprising each at least one cell containing a variety of phosphatidylinositol kinases,
   b) incubating one aliquot with a given compound,
   c) harvesting the cells of each aliquot,
   d) lysing the cells in order to obtain protein preparations,
   e) contacting the protein preparations with the immobilization product of claim 5 under conditions allowing the formation of one or more different complexes between one of the phosphatidylinositol kinases and the immobilization product, and
   f) determining the amount of the complex or the complexes formed in each aliquot in step e).

9. The method of claim 7, wherein a reduced amount of the complex formed in the aliquot incubated with the compound in comparison to the aliquot not incubated with the compound indicates that said phosphatidylinositol kinase interacts with the compound.

10. The method of claim 7, wherein the amount of the complex is determined by separating the phosphatidylinositol kinase from the immobilization product and subsequent detection of the separated phosphatidylinositol kinase or subsequent determination of the amount of the separated phosphatidylinositol kinase.

11. The method of claim 7, wherein said given compound is selected from the group consisting of synthetic compounds, or organic synthetic drugs and natural small molecule compounds.

12. The method of claim 7, wherein the given compound is a phosphatidylinositol kinase inhibitor.

13. The method of claim 7, wherein the provision of a protein preparation includes the steps of harvesting at least one cell containing phosphatidylinositol kinases and lysing the cell.

14. The method of claim 7, wherein the steps of the formation of the complex are performed under essentially physiological conditions.

* * * * *

SEQUENCE LISTING

<160> NUMBER OF SEQ ID NOS: 6

<210> SEQ ID NO 1
<211> LENGTH: 1068
<212> TYPE: PRT
<213> ORGANISM: Homo sapiens
<220> FEATURE:
<221> NAME/KEY: MISC_FEATURE
<222> LOCATION: (39)..(46)
<223> OTHER INFORMATION: peptide identified by mass spectrometry
<220> FEATURE:

```
<221> NAME/KEY: MISC_FEATURE
<222> LOCATION: (94)..(100)
<223> OTHER INFORMATION: peptide identified by mass spectrometry
<220> FEATURE:
<221> NAME/KEY: MISC_FEATURE
<222> LOCATION: (211)..(226)
<223> OTHER INFORMATION: peptide identified by mass spectrometry
<220> FEATURE:
<221> NAME/KEY: MISC_FEATURE
<222> LOCATION: (241)..(249)
<223> OTHER INFORMATION: peptide identified by mass spectrometry
<220> FEATURE:
<221> NAME/KEY: MISC_FEATURE
<222> LOCATION: (402)..(410)
<223> OTHER INFORMATION: peptide identified by mass spectrometry
<220> FEATURE:
<221> NAME/KEY: MISC_FEATURE
<222> LOCATION: (568)..(573)
<223> OTHER INFORMATION: peptide identified by mass spectrometry
<220> FEATURE:
<221> NAME/KEY: MISC_FEATURE
<222> LOCATION: (684)..(693)
<223> OTHER INFORMATION: peptide identified by mass spectrometry
<220> FEATURE:
<221> NAME/KEY: MISC_FEATURE
<222> LOCATION: (705)..(720)
<223> OTHER INFORMATION: peptide identified by mass spectrometry
<220> FEATURE:
<221> NAME/KEY: MISC_FEATURE
<222> LOCATION: (885)..(899)
<223> OTHER INFORMATION: peptide identified by mass spectrometry

<400> SEQUENCE: 1

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
```

```
            245                 250                 255
Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
            275                 280                 285

Ala Lys Glu Ser Leu Tyr Ser Gln Leu Pro Met Asp Cys Phe Thr Met
            290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                    325                 330                 335

Lys Ile Leu Cys Ala Thr Tyr Val Asn Val Asn Ile Arg Asp Ile Asp
                340                 345                 350

Lys Ile Tyr Val Arg Thr Gly Ile Tyr His Gly Gly Glu Pro Leu Cys
                355                 360                 365

Asp Asn Val Asn Thr Gln Arg Val Pro Cys Ser Asn Pro Arg Trp Asn
            370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
                420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
            450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
                500                 505                 510

Leu Ser Asn Arg Leu Ala Arg Asp Asn Glu Leu Arg Glu Asn Asp Lys
                515                 520                 525

Glu Gln Leu Lys Ala Ile Ser Thr Arg Asp Pro Leu Ser Glu Ile Thr
            530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670
```

```
Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg
        1010                1015                1020

Lys Thr Leu Ala Leu Asp Lys Thr Glu Gln Glu Ala Leu Glu Tyr
        1025                1030                1035

Phe Met Lys Gln Met Asn Asp Ala His His Gly Gly Trp Thr Thr
        1040                1045                1050

Lys Met Asp Trp Ile Phe His Thr Ile Lys Gln His Ala Leu Asn
        1055                1060                1065

<210> SEQ ID NO 2
<211> LENGTH: 1070
<212> TYPE: PRT
<213> ORGANISM: Homo sapiens
```

```
<220> FEATURE:
<221> NAME/KEY: MISC_FEATURE
<222> LOCATION: (49)..(61)
<223> OTHER INFORMATION: peptide identified by mass spectrometry
<220> FEATURE:
<221> NAME/KEY: MISC_FEATURE
<222> LOCATION: (91)..(110)
<223> OTHER INFORMATION: peptide identified by mass spectrometry
<220> FEATURE:
<221> NAME/KEY: MISC_FEATURE
<222> LOCATION: (115)..(121)
<223> OTHER INFORMATION: peptide identified by mass spectrometry
<220> FEATURE:
<221> NAME/KEY: MISC_FEATURE
<222> LOCATION: (133)..(149)
<223> OTHER INFORMATION: peptide identified by mass spectrometry
<220> FEATURE:
<221> NAME/KEY: MISC_FEATURE
<222> LOCATION: (154)..(159)
<223> OTHER INFORMATION: peptide identified by mass spectrometry
<220> FEATURE:
<221> NAME/KEY: MISC_FEATURE
<222> LOCATION: (192)..(196)
<223> OTHER INFORMATION: peptide identified by mass spectrometry
<220> FEATURE:
<221> NAME/KEY: MISC_FEATURE
<222> LOCATION: (232)..(319)
<223> OTHER INFORMATION: peptide identified by mass spectrometry
<220> FEATURE:
<221> NAME/KEY: MISC_FEATURE
<222> LOCATION: (340)..(350)
<223> OTHER INFORMATION: peptide identified by mass spectrometry
<220> FEATURE:
<221> NAME/KEY: MISC_FEATURE
<222> LOCATION: (355)..(396)
<223> OTHER INFORMATION: peptide identified by mass spectrometry
<220> FEATURE:
<221> NAME/KEY: MISC_FEATURE
<222> LOCATION: (400)..(412)
<223> OTHER INFORMATION: peptide identified by mass spectrometry
<220> FEATURE:
<221> NAME/KEY: MISC_FEATURE
<222> LOCATION: (425)..(429)
<223> OTHER INFORMATION: peptide identified by mass spectrometry
<220> FEATURE:
<221> NAME/KEY: MISC_FEATURE
<222> LOCATION: (434)..(449)
<223> OTHER INFORMATION: peptide identified by mass spectrometry
<220> FEATURE:
<221> NAME/KEY: MISC_FEATURE
<222> LOCATION: (501)..(510)
<223> OTHER INFORMATION: peptide identified by mass spectrometry
<220> FEATURE:
<221> NAME/KEY: MISC_FEATURE
<222> LOCATION: (515)..(529)
<223> OTHER INFORMATION: peptide identified by mass spectrometry
<220> FEATURE:
<221> NAME/KEY: MISC_FEATURE
<222> LOCATION: (540)..(562)
<223> OTHER INFORMATION: peptide identified by mass spectrometry
<220> FEATURE:
<221> NAME/KEY: MISC_FEATURE
<222> LOCATION: (567)..(581)
<223> OTHER INFORMATION: peptide identified by mass spectrometry
<220> FEATURE:
<221> NAME/KEY: MISC_FEATURE
<222> LOCATION: (585)..(600)
<223> OTHER INFORMATION: peptide identified by mass spectrometry
<220> FEATURE:
<221> NAME/KEY: MISC_FEATURE
<222> LOCATION: (605)..(628)
<223> OTHER INFORMATION: peptide identified by mass spectrometry
<220> FEATURE:
<221> NAME/KEY: MISC_FEATURE
<222> LOCATION: (648)..(663)
<223> OTHER INFORMATION: peptide identified by mass spectrometry
<220> FEATURE:
<221> NAME/KEY: MISC_FEATURE
<222> LOCATION: (670)..(679)
<223> OTHER INFORMATION: peptide identified by mass spectrometry
```

-continued

```
<220> FEATURE:
<221> NAME/KEY: MISC_FEATURE
<222> LOCATION: (712)..(718)
<223> OTHER INFORMATION: peptide identified by mass spectrometry
<220> FEATURE:
<221> NAME/KEY: MISC_FEATURE
<222> LOCATION: (721)..(732)
<223> OTHER INFORMATION: peptide identified by mass spectrometry
<220> FEATURE:
<221> NAME/KEY: MISC_FEATURE
<222> LOCATION: (740)..(747)
<223> OTHER INFORMATION: peptide identified by mass spectrometry
<220> FEATURE:
<221> NAME/KEY: MISC_FEATURE
<222> LOCATION: (753)..(775)
<223> OTHER INFORMATION: peptide identified by mass spectrometry
<220> FEATURE:
<221> NAME/KEY: MISC_FEATURE
<222> LOCATION: (778)..(847)
<223> OTHER INFORMATION: peptide identified by mass spectrometry
<220> FEATURE:
<221> NAME/KEY: MISC_FEATURE
<222> LOCATION: (879)..(896)
<223> OTHER INFORMATION: peptide identified by mass spectrometry
<220> FEATURE:
<221> NAME/KEY: MISC_FEATURE
<222> LOCATION: (921)..(928)
<223> OTHER INFORMATION: peptide identified by mass spectrometry
<220> FEATURE:
<221> NAME/KEY: MISC_FEATURE
<222> LOCATION: (930)..(946)
<223> OTHER INFORMATION: peptide identified by mass spectrometry
<220> FEATURE:
<221> NAME/KEY: MISC_FEATURE
<222> LOCATION: (982)..(994)
<223> OTHER INFORMATION: peptide identified by mass spectrometry
<220> FEATURE:
<221> NAME/KEY: MISC_FEATURE
<222> LOCATION: (1020)..(1050)
<223> OTHER INFORMATION: peptide identified by mass spectrometry
<220> FEATURE:
<221> NAME/KEY: MISC_FEATURE
<222> LOCATION: (1057)..(1065)
<223> OTHER INFORMATION: peptide identified by mass spectrometry

<400> SEQUENCE: 2

Met Cys Phe Ser Phe Ile Met Pro Pro Ala Met Ala Asp Ile Leu Asp
1               5                   10                  15

Ile Trp Ala Val Asp Ser Gln Ile Ala Ser Asp Gly Ser Ile Pro Val
            20                  25                  30

Asp Phe Leu Pro Thr Gly Ile Tyr Ile Gln Leu Glu Val Pro Arg
        35                  40                  45

Glu Ala Thr Ile Ser Tyr Ile Lys Gln Met Leu Trp Lys Gln Val His
    50                  55                  60

Asn Tyr Pro Met Phe Asn Leu Leu Met Asp Ile Asp Ser Tyr Met Phe
65                  70                  75                  80

Ala Cys Val Asn Gln Thr Ala Val Tyr Glu Glu Leu Glu Asp Glu Thr
                85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
        115                 120                 125

Leu Ile Gly Lys Gly Leu His Glu Phe Asp Ser Leu Lys Asp Pro Glu
    130                 135                 140

Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175
```

-continued

```
Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Lys Lys Thr
305                 310                 315                 320

Arg Ile Ile Ser His Val Trp Glu Asn Asn Pro Phe Gln Ile Val
                325                 330                 335

Leu Val Lys Gly Asn Lys Leu Asn Thr Glu Thr Val Lys Val His
            340                 345                 350

Val Arg Ala Gly Leu Phe His Gly Thr Glu Leu Leu Cys Lys Thr Ile
        355                 360                 365

Val Ser Ser Glu Val Ser Gly Lys Asn Asp His Ile Trp Asn Glu Pro
370                 375                 380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Lys Ser
                405                 410                 415

Thr Lys Thr Ile Asn Pro Ser Lys Tyr Gln Thr Ile Arg Lys Ala Gly
            420                 425                 430

Lys Val His Tyr Pro Val Ala Trp Val Asn Thr Met Val Phe Asp Phe
        435                 440                 445

Lys Gly Gln Leu Arg Thr Gly Asp Ile Ile Leu His Ser Trp Ser Ser
    450                 455                 460

Phe Pro Asp Glu Leu Glu Glu Met Leu Asn Pro Met Gly Thr Val Gln
465                 470                 475                 480

Thr Asn Pro Tyr Thr Glu Asn Ala Thr Ala Leu His Val Lys Phe Pro
                485                 490                 495

Glu Asn Lys Lys Gln Pro Tyr Tyr Tyr Pro Pro Phe Asp Lys Ile Ile
            500                 505                 510

Glu Lys Ala Ala Glu Ile Ala Ser Ser Asp Ser Ala Asn Val Ser Ser
        515                 520                 525

Arg Gly Gly Lys Lys Phe Leu Pro Val Leu Lys Glu Ile Leu Asp Arg
530                 535                 540

Asp Pro Leu Ser Gln Leu Cys Glu Asn Glu Met Asp Leu Ile Trp Thr
545                 550                 555                 560

Leu Arg Gln Asp Cys Arg Glu Ile Phe Pro Gln Ser Leu Pro Lys Leu
                565                 570                 575

Leu Leu Ser Ile Lys Trp Asn Lys Leu Glu Asp Val Ala Gln Leu Gln
            580                 585                 590

Ala Leu Leu Gln Ile Trp Pro Lys Leu Pro Pro Arg Glu Ala Leu Glu
        595                 600                 605
```

```
Leu Leu Asp Phe Asn Tyr Pro Asp Gln Tyr Val Arg Glu Tyr Ala Val
        610                 615                 620
Gly Cys Leu Arg Gln Met Ser Asp Glu Glu Leu Ser Gln Tyr Leu Leu
625                 630                 635                 640
Gln Leu Val Gln Val Leu Lys Tyr Glu Pro Phe Leu Asp Cys Ala Leu
                    645                 650                 655
Ser Arg Phe Leu Leu Glu Arg Ala Leu Gly Asn Arg Arg Ile Gly Gln
                660                 665                 670
Phe Leu Phe Trp His Leu Arg Ser Glu Val His Ile Pro Ala Val Ser
            675                 680                 685
Val Gln Phe Gly Val Ile Leu Glu Ala Tyr Cys Arg Gly Ser Val Gly
        690                 695                 700
His Met Lys Val Leu Ser Lys Gln Val Glu Ala Leu Asn Lys Leu Lys
705                 710                 715                 720
Thr Leu Asn Ser Leu Ile Lys Leu Asn Ala Val Lys Leu Asn Arg Ala
                    725                 730                 735
Lys Gly Lys Glu Ala Met His Thr Cys Leu Lys Gln Ser Ala Tyr Arg
                740                 745                 750
Glu Ala Leu Ser Asp Leu Gln Ser Pro Leu Asn Pro Cys Val Ile Leu
            755                 760                 765
Ser Glu Leu Tyr Val Lys Cys Lys Tyr Met Asp Ser Lys Met Lys
        770                 775                 780
Pro Leu Trp Leu Val Tyr Asn Asn Lys Val Phe Gly Glu Asp Ser Val
785                 790                 795                 800
Gly Val Ile Phe Lys Asn Gly Asp Asp Leu Arg Gln Asp Met Leu Thr
                    805                 810                 815
Leu Gln Met Leu Arg Leu Met Asp Leu Leu Trp Lys Glu Ala Gly Leu
                820                 825                 830
Asp Leu Arg Met Leu Pro Tyr Gly Cys Leu Ala Thr Gly Asp Arg Ser
            835                 840                 845
Gly Leu Ile Glu Val Val Ser Thr Ser Glu Thr Ile Ala Asp Ile Gln
        850                 855                 860
Leu Asn Ser Ser Asn Val Ala Ala Ala Ala Phe Asn Lys Asp Ala
865                 870                 875                 880
Leu Leu Asn Trp Leu Lys Glu Tyr Asn Ser Gly Asp Asp Leu Asp Arg
                    885                 890                 895
Ala Ile Glu Glu Phe Thr Leu Ser Cys Ala Gly Tyr Cys Val Ala Ser
                900                 905                 910
Tyr Val Leu Gly Ile Gly Asp Arg His Ser Asp Asn Ile Met Val Lys
            915                 920                 925
Lys Thr Gly Gln Leu Phe His Ile Asp Phe Gly His Ile Leu Gly Asn
        930                 935                 940
Phe Lys Ser Lys Phe Gly Ile Lys Arg Glu Arg Val Pro Phe Ile Leu
945                 950                 955                 960
Thr Tyr Asp Phe Ile His Val Ile Gln Gln Gly Lys Thr Gly Asn Thr
                    965                 970                 975
Glu Lys Phe Gly Arg Phe Arg Gln Cys Cys Glu Asp Ala Tyr Leu Ile
                980                 985                 990
Leu Arg Arg His Gly Asn Leu Phe Ile Thr Leu Phe Ala Leu Met Leu
            995                 1000                1005
Thr Ala Gly Leu Pro Glu Leu Thr Ser Val Lys Asp Ile Gln Tyr
        1010                1015                1020
Leu Lys Asp Ser Leu Ala Leu Gly Lys Ser Glu Glu Glu Ala Leu
```

-continued

```
                    1025                1030                1035

Lys Gln  Phe Lys Gln Lys  Phe Asp Glu Ala Leu Arg  Glu Ser Trp
         1040                1045                1050

Thr Thr  Lys Val Asn Trp  Met Ala His Thr Val Arg  Lys Asp Tyr
         1055                1060                1065

Arg Ser
    1070

<210> SEQ ID NO 3
<211> LENGTH: 2044
<212> TYPE: PRT
<213> ORGANISM: Homo sapiens
<220> FEATURE:
<221> NAME/KEY: MISC_FEATURE
<222> LOCATION: (52)..(61)
<223> OTHER INFORMATION: peptide identified by mass spectrometry
<220> FEATURE:
<221> NAME/KEY: MISC_FEATURE
<222> LOCATION: (139)..(149)
<223> OTHER INFORMATION: peptide identified by mass spectrometry
<220> FEATURE:
<221> NAME/KEY: MISC_FEATURE
<222> LOCATION: (161)..(169)
<223> OTHER INFORMATION: peptide identified by mass spectrometry
<220> FEATURE:
<221> NAME/KEY: MISC_FEATURE
<222> LOCATION: (340)..(358)
<223> OTHER INFORMATION: peptide identified by mass spectrometry
<220> FEATURE:
<221> NAME/KEY: MISC_FEATURE
<222> LOCATION: (438)..(462)
<223> OTHER INFORMATION: peptide identified by mass spectrometry
<220> FEATURE:
<221> NAME/KEY: MISC_FEATURE
<222> LOCATION: (509)..(517)
<223> OTHER INFORMATION: peptide identified by mass spectrometry
<220> FEATURE:
<221> NAME/KEY: MISC_FEATURE
<222> LOCATION: (521)..(540)
<223> OTHER INFORMATION: peptide identified by mass spectrometry
<220> FEATURE:
<221> NAME/KEY: MISC_FEATURE
<222> LOCATION: (575)..(586)
<223> OTHER INFORMATION: peptide identified by mass spectrometry
<220> FEATURE:
<221> NAME/KEY: MISC_FEATURE
<222> LOCATION: (628)..(637)
<223> OTHER INFORMATION: peptide identified by mass spectrometry
<220> FEATURE:
<221> NAME/KEY: MISC_FEATURE
<222> LOCATION: (772)..(784)
<223> OTHER INFORMATION: peptide identified by mass spectrometry
<220> FEATURE:
<221> NAME/KEY: MISC_FEATURE
<222> LOCATION: (795)..(807)
<223> OTHER INFORMATION: peptide identified by mass spectrometry
<220> FEATURE:
<221> NAME/KEY: MISC_FEATURE
<222> LOCATION: (899)..(908)
<223> OTHER INFORMATION: peptide identified by mass spectrometry
<220> FEATURE:
<221> NAME/KEY: MISC_FEATURE
<222> LOCATION: (970)..(982)
<223> OTHER INFORMATION: peptide identified by mass spectrometry
<220> FEATURE:
<221> NAME/KEY: MISC_FEATURE
<222> LOCATION: (1091)..(1113)
<223> OTHER INFORMATION: peptide identified by mass spectrometry
<220> FEATURE:
<221> NAME/KEY: MISC_FEATURE
<222> LOCATION: (1138)..(1146)
<223> OTHER INFORMATION: peptide identified by mass spectrometry
<220> FEATURE:
<221> NAME/KEY: MISC_FEATURE
<222> LOCATION: (1206)..(1228)
<223> OTHER INFORMATION: peptide identified by mass spectrometry
```

```
<220> FEATURE:
<221> NAME/KEY: MISC_FEATURE
<222> LOCATION: (1269)..(1278)
<223> OTHER INFORMATION: peptide identified by mass spectrometry
<220> FEATURE:
<221> NAME/KEY: MISC_FEATURE
<222> LOCATION: (1362)..(1387)
<223> OTHER INFORMATION: peptide identified by mass spectrometry
<220> FEATURE:
<221> NAME/KEY: MISC_FEATURE
<222> LOCATION: (1432)..(1444)
<223> OTHER INFORMATION: peptide identified by mass spectrometry
<220> FEATURE:
<221> NAME/KEY: MISC_FEATURE
<222> LOCATION: (1506)..(1516)
<223> OTHER INFORMATION: peptide identified by mass spectrometry
<220> FEATURE:
<221> NAME/KEY: MISC_FEATURE
<222> LOCATION: (1520)..(1533)
<223> OTHER INFORMATION: peptide identified by mass spectrometry
<220> FEATURE:
<221> NAME/KEY: MISC_FEATURE
<222> LOCATION: (1613)..(1621)
<223> OTHER INFORMATION: peptide identified by mass spectrometry
<220> FEATURE:
<221> NAME/KEY: MISC_FEATURE
<222> LOCATION: (1683)..(1695)
<223> OTHER INFORMATION: peptide identified by mass spectrometry
<220> FEATURE:
<221> NAME/KEY: MISC_FEATURE
<222> LOCATION: (1702)..(1711)
<223> OTHER INFORMATION: peptide identified by mass spectrometry
<220> FEATURE:
<221> NAME/KEY: MISC_FEATURE
<222> LOCATION: (1733)..(1742)
<223> OTHER INFORMATION: peptide identified by mass spectrometry
<220> FEATURE:
<221> NAME/KEY: MISC_FEATURE
<222> LOCATION: (1784)..(1792)
<223> OTHER INFORMATION: peptide identified by mass spectrometry
<220> FEATURE:
<221> NAME/KEY: MISC_FEATURE
<222> LOCATION: (1828)..(1847)
<223> OTHER INFORMATION: peptide identified by mass spectrometry
<220> FEATURE:
<221> NAME/KEY: MISC_FEATURE
<222> LOCATION: (1853)..(1878)
<223> OTHER INFORMATION: peptide identified by mass spectrometry
<220> FEATURE:
<221> NAME/KEY: MISC_FEATURE
<222> LOCATION: (2011)..(2028)
<223> OTHER INFORMATION: peptide identified by mass spectrometry

<400> SEQUENCE: 3

Met Cys Pro Val Asp Phe His Gly Ile Phe Gln Leu Asp Glu Arg Arg
1               5                   10                  15

Arg Asp Ala Val Ile Ala Leu Gly Ile Phe Leu Ile Glu Ser Asp Leu
            20                  25                  30

Gln His Lys Asp Cys Val Val Pro Tyr Leu Leu Arg Leu Leu Lys Gly
        35                  40                  45

Leu Pro Lys Val Tyr Trp Val Glu Glu Ser Thr Ala Arg Lys Gly Arg
    50                  55                  60

Gly Ala Leu Pro Val Ala Glu Ser Phe Ser Phe Cys Leu Val Thr Leu
65                  70                  75                  80

Leu Ser Asp Val Ala Tyr Arg Asp Pro Ser Leu Arg Asp Glu Ile Leu
                85                  90                  95

Glu Val Leu Leu Gln Val Leu His Val Leu Leu Gly Met Cys Gln Ala
            100                 105                 110

Leu Glu Ile Gln Asp Lys Glu Tyr Leu Cys Lys Tyr Ala Ile Pro Cys
        115                 120                 125

Leu Ile Gly Ile Ser Arg Ala Phe Gly Arg Tyr Ser Asn Met Glu Glu
```

```
                130                 135                 140
Ser Leu Leu Ser Lys Leu Phe Pro Lys Ile Pro Pro His Ser Leu Arg
145                 150                 155                 160

Val Leu Glu Glu Leu Glu Gly Val Arg Arg Arg Ser Phe Asn Asp Phe
                165                 170                 175

Arg Ser Ile Leu Pro Ser Asn Leu Leu Thr Val Cys Gln Glu Gly Thr
            180                 185                 190

Leu Lys Arg Lys Thr Ser Val Ser Ser Ile Ser Gln Val Ser Pro
        195                 200                 205

Glu Arg Gly Met Pro Pro Ser Ser Pro Gly Gly Ser Ala Phe His
210                 215                 220

Tyr Phe Glu Ala Ser Cys Leu Pro Asp Gly Thr Ala Leu Glu Pro Glu
225                 230                 235                 240

Tyr Tyr Phe Ser Thr Ile Ser Ser Phe Ser Val Ser Pro Leu Phe
                245                 250                 255

Asn Gly Val Thr Tyr Lys Glu Phe Asn Ile Pro Leu Glu Met Leu Arg
            260                 265                 270

Glu Leu Leu Asn Leu Val Lys Lys Ile Val Glu Glu Ala Val Leu Lys
        275                 280                 285

Ser Leu Asp Ala Ile Val Ala Ser Val Met Glu Ala Asn Pro Ser Ala
290                 295                 300

Asp Leu Tyr Tyr Thr Ser Phe Ser Asp Pro Leu Tyr Leu Thr Met Phe
305                 310                 315                 320

Lys Met Leu Arg Asp Thr Leu Tyr Tyr Met Lys Asp Leu Pro Thr Ser
                325                 330                 335

Phe Val Lys Glu Ile His Asp Phe Val Leu Glu Gln Phe Asn Thr Ser
            340                 345                 350

Gln Gly Glu Leu Gln Lys Ile Leu His Asp Ala Asp Arg Ile His Asn
        355                 360                 365

Glu Leu Ser Pro Leu Lys Leu Arg Cys Gln Ala Ser Ala Ala Cys Val
370                 375                 380

Asp Leu Met Val Trp Ala Val Lys Asp Glu Gln Gly Ala Glu Asn Leu
385                 390                 395                 400

Cys Ile Lys Leu Ser Glu Lys Leu Gln Ser Lys Thr Ser Ser Lys Val
                405                 410                 415

Ile Ile Ala His Leu Pro Leu Leu Ile Cys Cys Leu Gln Gly Leu Gly
            420                 425                 430

Arg Leu Cys Glu Arg Phe Pro Val Val His Ser Val Thr Pro Ser
        435                 440                 445

Leu Arg Asp Phe Leu Val Ile Pro Ser Pro Val Leu Val Lys Leu Tyr
450                 455                 460

Lys Tyr His Ser Gln Tyr His Thr Val Ala Gly Asn Asp Ile Lys Ile
465                 470                 475                 480

Ser Val Thr Asn Glu His Ser Glu Ser Thr Leu Asn Val Met Ser Gly
                485                 490                 495

Lys Lys Ser Gln Pro Ser Met Tyr Glu Gln Leu Arg Asp Ile Ala Ile
            500                 505                 510

Asp Asn Ile Cys Arg Cys Leu Lys Ala Gly Leu Thr Val Asp Pro Val
        515                 520                 525

Ile Val Glu Ala Phe Leu Ala Ser Leu Ser Asn Arg Leu Tyr Ile Ser
530                 535                 540

Gln Glu Ser Asp Lys Asp Ala His Leu Ile Pro Asp His Thr Ile Arg
545                 550                 555                 560
```

```
Ala Leu Gly His Ile Ala Val Ala Leu Arg Asp Thr Pro Lys Val Met
            565                 570                 575

Glu Pro Ile Leu Gln Ile Leu Gln Gln Lys Phe Cys Gln Pro Pro Ser
            580                 585                 590

Pro Leu Asp Val Leu Ile Ile Asp Gln Leu Gly Cys Leu Val Ile Thr
            595                 600                 605

Gly Asn Gln Tyr Ile Tyr Gln Glu Val Trp Asn Leu Phe Gln Gln Ile
610                 615                 620

Ser Val Lys Ala Ser Ser Val Val Tyr Ser Ala Thr Lys Asp Tyr Lys
625                 630                 635                 640

Asp His Gly Tyr Arg His Cys Ser Leu Ala Val Ile Asn Ala Leu Ala
            645                 650                 655

Asn Ile Ala Ala Asn Ile Gln Asp Glu His Leu Val Asp Glu Leu Leu
            660                 665                 670

Met Asn Leu Leu Glu Leu Phe Val Gln Leu Gly Leu Glu Gly Lys Arg
            675                 680                 685

Ala Ser Glu Arg Ala Ser Glu Lys Gly Pro Ala Leu Lys Ala Ser Ser
            690                 695                 700

Ser Ala Gly Asn Leu Gly Val Leu Ile Pro Val Ile Ala Val Leu Thr
705                 710                 715                 720

Arg Arg Leu Pro Pro Ile Lys Glu Ala Lys Pro Arg Leu Gln Lys Leu
            725                 730                 735

Phe Arg Asp Phe Trp Leu Tyr Ser Val Leu Met Gly Phe Ala Val Glu
            740                 745                 750

Gly Ser Gly Leu Trp Pro Glu Trp Tyr Glu Gly Val Cys Glu Ile
            755                 760                 765

Ala Thr Lys Ser Pro Leu Leu Thr Phe Pro Ser Lys Glu Pro Leu Arg
770                 775                 780

Ser Val Leu Gln Tyr Asn Ser Ala Met Lys Asn Asp Thr Val Thr Pro
785                 790                 795                 800

Ala Glu Leu Ser Glu Leu Arg Ser Thr Ile Ile Asn Leu Leu Asp Pro
            805                 810                 815

Pro Pro Glu Val Ser Ala Leu Ile Asn Lys Leu Asp Phe Ala Met Ser
            820                 825                 830

Thr Tyr Leu Leu Ser Val Tyr Arg Leu Glu Tyr Met Arg Val Leu Arg
            835                 840                 845

Ser Thr Asp Pro Asp Arg Phe Gln Val Met Phe Cys Tyr Phe Glu Asp
850                 855                 860

Lys Ala Ile Gln Lys Asp Lys Ser Gly Met Met Gln Cys Val Ile Ala
865                 870                 875                 880

Val Ala Asp Lys Val Phe Asp Ala Phe Leu Asn Met Met Ala Asp Lys
            885                 890                 895

Ala Lys Thr Lys Glu Asn Glu Glu Leu Glu Arg His Ala Gln Phe
            900                 905                 910

Leu Leu Val Asn Phe Asn His Ile His Lys Arg Ile Arg Arg Val Ala
            915                 920                 925

Asp Lys Tyr Leu Ser Gly Leu Val Asp Lys Phe Pro His Leu Leu Trp
            930                 935                 940

Ser Gly Thr Val Leu Lys Thr Met Leu Asp Ile Leu Gln Thr Leu Ser
945                 950                 955                 960

Leu Ser Leu Ser Ala Asp Ile His Lys Asp Gln Pro Tyr Tyr Asp Ile
            965                 970                 975

Pro Asp Ala Pro Tyr Arg Ile Thr Val Pro Asp Thr Tyr Glu Ala Arg
            980                 985                 990
```

```
Glu Ser Ile Val Lys Asp Phe Ala  Ala Arg Cys Gly Met  Ile Leu Gln
        995              1000                 1005

Glu Ala  Met Lys Trp Ala Pro  Thr Val Thr Lys Ser  His Leu Gln
    1010             1015                 1020

Glu Tyr  Leu Asn Lys His Gln  Asn Trp Val Ser Gly  Leu Ser Gln
    1025             1030                 1035

His Thr  Gly Leu Ala Met Ala  Thr Glu Ser Ile Leu  His Phe Ala
    1040             1045                 1050

Gly Tyr  Asn Lys Gln Asn Thr  Thr Leu Gly Ala Thr  Gln Leu Ser
    1055             1060                 1065

Glu Arg  Pro Ala Cys Val Lys  Lys Asp Tyr Ser Asn  Phe Met Ala
    1070             1075                 1080

Ser Leu  Asn Leu Arg Asn Arg  Tyr Ala Gly Glu Val  Tyr Gly Met
    1085             1090                 1095

Ile Arg  Phe Ser Gly Thr Thr  Gly Gln Met Ser Asp  Leu Asn Lys
    1100             1105                 1110

Met Met  Val Gln Asp Leu His  Ser Ala Leu Asp Arg  Ser His Pro
    1115             1120                 1125

Gln His  Tyr Thr Gln Ala Met  Phe Lys Leu Thr Ala  Met Leu Ile
    1130             1135                 1140

Ser Ser  Lys Asp Cys Asp Pro  Gln Leu Leu His His  Leu Cys Trp
    1145             1150                 1155

Gly Pro  Leu Arg Met Phe Asn  Glu His Gly Met Glu  Thr Ala Leu
    1160             1165                 1170

Ala Cys  Trp Glu Trp Leu Leu  Ala Gly Lys Asp Gly  Val Glu Val
    1175             1180                 1185

Pro Phe  Met Arg Glu Met Ala  Gly Ala Trp His Met  Thr Val Glu
    1190             1195                 1200

Gln Lys  Phe Gly Leu Phe Ser  Ala Glu Ile Lys Glu  Ala Asp Pro
    1205             1210                 1215

Leu Ala  Ala Ser Glu Ala Ser  Gln Pro Lys Pro Cys  Pro Pro Glu
    1220             1225                 1230

Val Thr  Pro His Tyr Ile Trp  Ile Asp Phe Leu Val  Gln Arg Phe
    1235             1240                 1245

Glu Ile  Ala Lys Tyr Cys Ser  Ser Asp Gln Val Glu  Ile Phe Ser
    1250             1255                 1260

Ser Leu  Leu Gln Arg Ser Met  Ser Leu Asn Ile Gly  Gly Ala Lys
    1265             1270                 1275

Gly Ser  Met Asn Arg His Val  Ala Ala Ile Gly Pro  Arg Phe Lys
    1280             1285                 1290

Leu Leu  Thr Leu Gly Leu Ser  Leu Leu His Ala Asp  Val Val Pro
    1295             1300                 1305

Asn Ala  Thr Ile Arg Asn Val  Leu Arg Glu Lys Ile  Tyr Ser Thr
    1310             1315                 1320

Ala Phe  Asp Tyr Phe Ser Cys  Pro Pro Lys Phe Pro  Thr Gln Gly
    1325             1330                 1335

Glu Lys  Arg Leu Arg Glu Asp  Ile Ser Ile Met Ile  Lys Phe Trp
    1340             1345                 1350

Thr Ala  Met Phe Ser Asp Lys  Lys Tyr Leu Thr Ala  Ser Gln Leu
    1355             1360                 1365

Val Pro  Pro Asp Asn Gln Asp  Thr Arg Ser Asn Leu  Asp Ile Thr
    1370             1375                 1380

Val Gly  Ser Arg Gln Gln Ala  Thr Gln Gly Trp Ile  Asn Thr Tyr
```

```
            1385                1390                1395

Pro Leu Ser Ser Gly Met Ser Thr Ile Ser Lys Lys Ser Gly Met
    1400                1405                1410

Ser Lys Lys Thr Asn Arg Gly Ser Gln Leu His Lys Tyr Tyr Met
    1415                1420                1425

Lys Arg Arg Thr Leu Leu Leu Ser Leu Leu Ala Thr Glu Ile Glu
    1430                1435                1440

Arg Leu Ile Thr Trp Tyr Asn Pro Leu Ser Ala Pro Glu Leu Glu
    1445                1450                1455

Leu Asp Gln Ala Gly Glu Asn Ser Val Ala Asn Trp Arg Ser Lys
    1460                1465                1470

Tyr Ile Ser Leu Ser Glu Lys Gln Trp Lys Asp Asn Val Asn Leu
    1475                1480                1485

Ala Trp Ser Ile Ser Pro Tyr Leu Ala Val Gln Leu Pro Ala Arg
    1490                1495                1500

Phe Lys Asn Thr Glu Ala Ile Gly Asn Glu Val Thr Arg Leu Val
    1505                1510                1515

Arg Leu Asp Pro Gly Ala Val Ser Asp Val Pro Glu Ala Ile Lys
    1520                1525                1530

Phe Leu Val Thr Trp His Thr Ile Asp Ala Asp Ala Pro Glu Leu
    1535                1540                1545

Ser His Val Leu Cys Trp Ala Pro Thr Asp Pro Thr Gly Leu
    1550                1555                1560

Ser Tyr Phe Ser Ser Met Tyr Pro Pro His Pro Leu Thr Ala Gln
    1565                1570                1575

Tyr Gly Val Lys Val Leu Arg Ser Phe Pro Pro Asp Ala Ile Leu
    1580                1585                1590

Phe Tyr Ile Pro Gln Ile Val Gln Ala Leu Arg Tyr Asp Lys Met
    1595                1600                1605

Gly Tyr Val Arg Glu Tyr Ile Leu Trp Ala Ala Ser Lys Ser Gln
    1610                1615                1620

Leu Leu Ala His Gln Phe Ile Trp Asn Met Lys Thr Asn Ile Tyr
    1625                1630                1635

Leu Asp Glu Glu Gly His Gln Lys Asp Pro Asp Ile Gly Asp Leu
    1640                1645                1650

Leu Asp Gln Leu Val Glu Glu Ile Thr Gly Ser Leu Ser Gly Pro
    1655                1660                1665

Ala Lys Asp Phe Tyr Gln Arg Glu Phe Asp Phe Phe Asn Lys Ile
    1670                1675                1680

Thr Asn Val Ser Ala Ile Ile Lys Pro Tyr Pro Lys Gly Asp Glu
    1685                1690                1695

Arg Lys Lys Ala Cys Leu Ser Ala Leu Ser Glu Val Lys Val Gln
    1700                1705                1710

Pro Gly Cys Tyr Leu Pro Ser Asn Pro Glu Ala Ile Val Leu Asp
    1715                1720                1725

Ile Asp Tyr Lys Ser Gly Thr Pro Met Gln Ser Ala Ala Lys Ala
    1730                1735                1740

Pro Tyr Leu Ala Lys Phe Lys Val Lys Arg Cys Gly Val Ser Glu
    1745                1750                1755

Leu Glu Lys Glu Gly Leu Arg Cys Arg Ser Asp Ser Glu Asp Glu
    1760                1765                1770

Cys Ser Thr Gln Glu Ala Asp Gly Gln Lys Ile Ser Trp Gln Ala
    1775                1780                1785
```

-continued

```
Ala Ile Phe Lys Val Gly Asp Asp Cys Arg Gln Asp Met Leu Ala
    1790            1795                1800

Leu Gln Ile Ile Asp Leu Phe Lys Asn Ile Phe Gln Leu Val Gly
1805            1810                1815

Leu Asp Leu Phe Val Phe Pro Tyr Arg Val Val Ala Thr Ala Pro
1820            1825                1830

Gly Cys Gly Val Ile Glu Cys Ile Pro Asp Cys Thr Ser Arg Asp
1835            1840                1845

Gln Leu Gly Arg Gln Thr Asp Phe Gly Met Tyr Asp Tyr Phe Thr
1850            1855                1860

Arg Gln Tyr Gly Asp Glu Ser Thr Leu Ala Phe Gln Gln Ala Arg
1865            1870                1875

Tyr Asn Phe Ile Arg Ser Met Ala Ala Tyr Ser Leu Leu Leu Phe
1880            1885                1890

Leu Leu Gln Ile Lys Asp Arg His Asn Gly Asn Ile Met Leu Asp
1895            1900                1905

Lys Lys Gly His Ile Ile His Ile Asp Phe Gly Phe Met Phe Glu
1910            1915                1920

Ser Ser Pro Gly Gly Asn Leu Gly Trp Glu Pro Asp Ile Lys Leu
1925            1930                1935

Thr Asp Glu Met Val Met Ile Met Gly Gly Lys Met Glu Ala Thr
1940            1945                1950

Pro Phe Lys Trp Phe Met Glu Met Cys Val Arg Gly Tyr Leu Ala
1955            1960                1965

Val Arg Pro Tyr Met Asp Ala Val Val Ser Leu Val Thr Leu Met
1970            1975                1980

Leu Asp Thr Gly Leu Pro Cys Phe Arg Gly Gln Thr Ile Lys Leu
1985            1990                1995

Leu Lys His Arg Phe Ser Pro Asn Met Thr Glu Arg Glu Ala Ala
2000            2005                2010

Asn Phe Ile Met Lys Val Ile Gln Ser Cys Phe Leu Ser Asn Arg
2015            2020                2025

Ser Arg Thr Tyr Asp Met Ile Gln Tyr Tyr Gln Asn Asp Ile Pro
2030            2035                2040

Tyr
```

<210> SEQ ID NO 4
<211> LENGTH: 421
<212> TYPE: PRT
<213> ORGANISM: Homo sapiens
<220> FEATURE:
<221> NAME/KEY: MISC_FEATURE
<222> LOCATION: (32)..(37)
<223> OTHER INFORMATION: peptide identified by mass spectrometry
<220> FEATURE:
<221> NAME/KEY: MISC_FEATURE
<222> LOCATION: (82)..(109)
<223> OTHER INFORMATION: peptide identified by mass spectrometry
<220> FEATURE:
<221> NAME/KEY: MISC_FEATURE
<222> LOCATION: (113)..(140)
<223> OTHER INFORMATION: peptide identified by mass spectrometry
<220> FEATURE:
<221> NAME/KEY: MISC_FEATURE
<222> LOCATION: (151)..(204)
<223> OTHER INFORMATION: peptide identified by mass spectrometry
<220> FEATURE:
<221> NAME/KEY: MISC_FEATURE
<222> LOCATION: (227)..(248)
<223> OTHER INFORMATION: peptide identified by mass spectrometry
<220> FEATURE:
<221> NAME/KEY: MISC_FEATURE
<220> FEATURE:
<221> NAME/KEY: MISC_FEATURE
<222> LOCATION: (251)..(265)
<223> OTHER INFORMATION: peptide identified by mass spectrometry
<220> FEATURE:
<221> NAME/KEY: MISC_FEATURE
<222> LOCATION: (269)..(292)
<223> OTHER INFORMATION: peptide identified by mass spectrometry
<220> FEATURE:
<221> NAME/KEY: MISC_FEATURE
<222> LOCATION: (341)..(365)
<223> OTHER INFORMATION: peptide identified by mass spectrometry
<220> FEATURE:
<221> NAME/KEY: MISC_FEATURE
<222> LOCATION: (394)..(410)
<223> OTHER INFORMATION: peptide identified by mass spectrometry
<220> FEATURE:
<221> NAME/KEY: MISC_FEATURE
<222> LOCATION: (412)..(421)
<223> OTHER INFORMATION: peptide identified by mass spectrometry

<400> SEQUENCE: 4

```
Met Ala Ser Ser Val Pro Pro Ala Thr Val Ser Ala Ala Thr Ala
  1               5                  10                  15

Gly Pro Gly Pro Gly Phe Gly Phe Ala Ser Lys Thr Lys Lys His
                 20                  25                  30

Phe Val Gln Gln Lys Val Lys Val Phe Arg Ala Ala Asp Pro Leu Val
             35                  40                  45

Gly Val Phe Leu Trp Gly Val Ala His Ser Ile Asn Glu Leu Ser Gln
 50                  55                  60

Val Pro Pro Pro Val Met Leu Leu Pro Asp Asp Phe Lys Ala Ser Ser
 65                  70                  75                  80

Lys Ile Lys Val Asn Asn His Leu Phe His Arg Glu Asn Leu Pro Ser
                 85                  90                  95

His Phe Lys Phe Lys Glu Tyr Cys Pro Gln Val Phe Arg Asn Leu Arg
            100                 105                 110

Asp Arg Phe Gly Ile Asp Asp Gln Asp Tyr Leu Val Ser Leu Thr Arg
            115                 120                 125

Asn Pro Pro Ser Glu Ser Glu Gly Ser Asp Gly Arg Phe Leu Ile Ser
130                 135                 140

Tyr Asp Arg Thr Leu Val Ile Lys Glu Val Ser Ser Glu Asp Ile Ala
145                 150                 155                 160

Asp Met His Ser Asn Leu Ser Asn Tyr His Gln Tyr Ile Val Lys Cys
                165                 170                 175

His Gly Asn Thr Leu Leu Pro Gln Phe Leu Gly Met Tyr Arg Val Ser
            180                 185                 190

Val Asp Asn Glu Asp Ser Tyr Met Leu Val Met Arg Asn Met Phe Ser
            195                 200                 205

His Arg Leu Pro Val His Arg Lys Tyr Asp Leu Lys Gly Ser Leu Val
210                 215                 220

Ser Arg Glu Ala Ser Asp Lys Glu Lys Val Lys Glu Leu Pro Thr Leu
225                 230                 235                 240

Lys Asp Met Asp Phe Leu Asn Lys Asn Gln Lys Val Tyr Ile Gly Glu
                245                 250                 255

Glu Glu Lys Lys Ile Phe Leu Glu Lys Leu Lys Arg Asp Val Glu Phe
            260                 265                 270

Leu Val Gln Leu Lys Ile Met Asp Tyr Ser Leu Leu Leu Gly Ile His
            275                 280                 285

Asp Ile Ile Arg Gly Ser Glu Pro Glu Glu Glu Gly Pro Val Arg Glu
            290                 295                 300

Asp Glu Ser Glu Val Asp Gly Asp Cys Ser Leu Thr Gly Pro Pro Ala
305                 310                 315                 320
```

Leu Val Gly Ser Tyr Gly Thr Ser Pro Glu Gly Ile Gly Tyr Ile
            325                 330                 335

His Ser His Arg Pro Leu Gly Pro Gly Glu Phe Glu Ser Phe Ile Asp
            340                 345                 350

Val Tyr Ala Ile Arg Ser Ala Glu Gly Ala Pro Gln Lys Glu Val Tyr
            355                 360                 365

Phe Met Gly Leu Ile Asp Ile Leu Thr Gln Tyr Asp Ala Lys Lys Lys
    370                 375                 380

Ala Ala His Ala Ala Lys Thr Val Lys His Gly Ala Gly Ala Glu Ile
385                 390                 395                 400

Ser Thr Val His Pro Glu Gln Tyr Ala Lys Arg Phe Leu Asp Phe Ile
            405                 410                 415

Thr Asn Ile Phe Ala
            420

<210> SEQ ID NO 5
<211> LENGTH: 1102
<212> TYPE: PRT
<213> ORGANISM: Homo sapiens
<220> FEATURE:
<221> NAME/KEY: MISC_FEATURE
<222> LOCATION: (78)..(102)
<223> OTHER INFORMATION: peptide identified by mass spectrometry
<220> FEATURE:
<221> NAME/KEY: MISC_FEATURE
<222> LOCATION: (131)..(140)
<223> OTHER INFORMATION: peptide identified by mass spectrometry
<220> FEATURE:
<221> NAME/KEY: MISC_FEATURE
<222> LOCATION: (215)..(251)
<223> OTHER INFORMATION: peptide identified by mass spectrometry
<220> FEATURE:
<221> NAME/KEY: MISC_FEATURE
<222> LOCATION: (274)..(288)
<223> OTHER INFORMATION: peptide identified by mass spectrometry
<220> FEATURE:
<221> NAME/KEY: MISC_FEATURE
<222> LOCATION: (367)..(375)
<223> OTHER INFORMATION: peptide identified by mass spectrometry
<220> FEATURE:
<221> NAME/KEY: MISC_FEATURE
<222> LOCATION: (426)..(437)
<223> OTHER INFORMATION: peptide identified by mass spectrometry
<220> FEATURE:
<221> NAME/KEY: MISC_FEATURE
<222> LOCATION: (445)..(455)
<223> OTHER INFORMATION: peptide identified by mass spectrometry
<220> FEATURE:
<221> NAME/KEY: MISC_FEATURE
<222> LOCATION: (491)..(501)
<223> OTHER INFORMATION: peptide identified by mass spectrometry
<220> FEATURE:
<221> NAME/KEY: MISC_FEATURE
<222> LOCATION: (598)..(606)
<223> OTHER INFORMATION: peptide identified by mass spectrometry
<220> FEATURE:
<221> NAME/KEY: MISC_FEATURE
<222> LOCATION: (713)..(722)
<223> OTHER INFORMATION: peptide identified by mass spectrometry
<220> FEATURE:
<221> NAME/KEY: MISC_FEATURE
<222> LOCATION: (769)..(800)
<223> OTHER INFORMATION: peptide identified by mass spectrometry
<220> FEATURE:
<221> NAME/KEY: MISC_FEATURE
<222> LOCATION: (876)..(883)
<223> OTHER INFORMATION: peptide identified by mass spectrometry
<220> FEATURE:
<221> NAME/KEY: MISC_FEATURE
<222> LOCATION: (891)..(912)
<223> OTHER INFORMATION: peptide identified by mass spectrometry
<220> FEATURE:

```
<221> NAME/KEY: MISC_FEATURE
<222> LOCATION: (974)..(980)
<223> OTHER INFORMATION: peptide identified by mass spectrometry
<220> FEATURE:
<221> NAME/KEY: MISC_FEATURE
<222> LOCATION: (983)..(1000)
<223> OTHER INFORMATION: peptide identified by mass spectrometry
<220> FEATURE:
<221> NAME/KEY: MISC_FEATURE
<222> LOCATION: (1009)..(1015)
<223> OTHER INFORMATION: peptide identified by mass spectrometry
<220> FEATURE:
<221> NAME/KEY: MISC_FEATURE
<222> LOCATION: (1046)..(1052)
<223> OTHER INFORMATION: peptide identified by mass spectrometry
<220> FEATURE:
<221> NAME/KEY: MISC_FEATURE
<222> LOCATION: (1067)..(1076)
<223> OTHER INFORMATION: peptide identified by mass spectrometry

<400> SEQUENCE: 5
```

```
Met Glu Leu Glu Asn Tyr Lys Gln Pro Val Leu Arg Glu Asp Asn
 1               5                  10                  15

Cys Arg Arg Arg Arg Met Lys Pro Arg Ser Ala Ala Ser Leu
            20                  25                  30

Ser Ser Met Glu Leu Ile Pro Ile Glu Phe Val Leu Pro Thr Ser Gln
        35                  40                  45

Arg Lys Cys Lys Ser Pro Glu Thr Ala Leu Leu His Val Ala Gly His
    50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
            115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
    210                 215                 220

His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270

Arg Val Cys Gly Arg Asp Glu Tyr Leu Val Gly Glu Thr Pro Ile Lys
        275                 280                 285

Asn Phe Gln Trp Val Arg His Cys Leu Lys Asn Gly Glu Glu Ile His
    290                 295                 300

Val Val Leu Asp Thr Pro Pro Asp Pro Ala Leu Asp Glu Val Arg Lys
```

-continued

```
             305                 310                 315                 320
Glu Glu Trp Pro Leu Val Asp Asp Cys Thr Gly Val Thr Gly Tyr His
            325                 330                 335

Glu Gln Leu Thr Ile His Gly Lys Asp His Glu Ser Val Phe Thr Val
            340                 345                 350

Ser Leu Trp Asp Cys Asp Arg Lys Phe Arg Val Lys Ile Arg Gly Ile
            355                 360                 365

Asp Ile Pro Val Leu Pro Arg Asn Thr Asp Leu Thr Phe Val Glu
370                 375                 380

Ala Asn Ile Gln His Gly Gln Gln Val Leu Cys Gln Arg Arg Thr Ser
385                 390                 395                 400

Pro Lys Pro Phe Thr Glu Glu Val Leu Trp Asn Val Trp Leu Glu Phe
            405                 410                 415

Ser Ile Lys Ile Lys Asp Leu Pro Lys Gly Ala Leu Leu Asn Leu Gln
            420                 425                 430

Ile Tyr Cys Gly Lys Ala Pro Ala Leu Ser Ser Lys Ala Ser Ala Glu
            435                 440                 445

Ser Pro Ser Ser Glu Ser Lys Gly Lys Val Gln Leu Leu Tyr Tyr Val
450                 455                 460

Asn Leu Leu Leu Ile Asp His Arg Phe Leu Leu Arg Arg Gly Glu Tyr
465                 470                 475                 480

Val Leu His Met Trp Gln Ile Ser Gly Lys Gly Glu Asp Gln Gly Ser
            485                 490                 495

Phe Asn Ala Asp Lys Leu Thr Ser Ala Thr Asn Pro Asp Lys Glu Asn
            500                 505                 510

Ser Met Ser Ile Ser Ile Leu Leu Asp Asn Tyr Cys His Pro Ile Ala
            515                 520                 525

Leu Pro Lys His Gln Pro Thr Pro Asp Pro Glu Gly Asp Arg Val Arg
            530                 535                 540

Ala Glu Met Pro Asn Gln Leu Arg Lys Gln Leu Glu Ala Ile Ile Ala
545                 550                 555                 560

Thr Asp Pro Leu Asn Pro Leu Thr Ala Glu Asp Lys Glu Leu Leu Trp
            565                 570                 575

His Phe Arg Tyr Glu Ser Leu Lys His Pro Lys Ala Tyr Pro Lys Leu
            580                 585                 590

Phe Ser Ser Val Lys Trp Gly Gln Gln Glu Ile Val Ala Lys Thr Tyr
            595                 600                 605

Gln Leu Leu Ala Arg Arg Glu Val Trp Asp Gln Ser Ala Leu Asp Val
            610                 615                 620

Gly Leu Thr Met Gln Leu Leu Asp Cys Asn Phe Ser Asp Glu Asn Val
625                 630                 635                 640

Arg Ala Ile Ala Val Gln Lys Leu Glu Ser Leu Glu Asp Asp Val
                645                 650                 655

Leu His Tyr Leu Leu Gln Leu Val Gln Ala Val Lys Phe Glu Pro Tyr
            660                 665                 670

His Asp Ser Ala Leu Ala Arg Phe Leu Leu Lys Arg Gly Leu Arg Asn
            675                 680                 685

Lys Arg Ile Gly His Phe Leu Phe Trp Phe Leu Arg Ser Glu Ile Ala
            690                 695                 700

Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
            725                 730                 735
```

```
Gln Val Ile Glu Met Leu Gln Lys Val Thr Leu Asp Ile Lys Ser Leu
                740                 745                 750

Ser Ala Glu Lys Tyr Asp Val Ser Gln Val Ile Ser Gln Leu Lys
            755                 760                 765

Gln Lys Leu Glu Asn Leu Gln Asn Ser Gln Leu Pro Glu Ser Phe Arg
770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Pro Leu Trp Leu Glu Phe Lys
                805                 810                 815

Cys Ala Asp Pro Thr Ala Leu Ser Asn Glu Thr Ile Gly Ile Ile Phe
                820                 825                 830

Lys His Gly Asp Asp Leu Arg Gln Asp Met Leu Ile Leu Gln Ile Leu
            835                 840                 845

Arg Ile Met Glu Ser Ile Trp Glu Thr Glu Ser Leu Asp Leu Cys Leu
850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
            930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys Thr Ser Pro His Phe Gln Lys
        995                 1000                1005

Phe Gln Asp Ile Cys Val Lys Ala Tyr Leu Ala Leu Arg His His
    1010                1015                1020

Thr Asn Leu Leu Ile Ile Leu Phe Ser Met Met Leu Met Thr Gly
    1025                1030                1035

Met Pro Gln Leu Thr Ser Lys Glu Asp Ile Glu Tyr Ile Arg Asp
    1040                1045                1050

Ala Leu Thr Val Gly Lys Asn Glu Glu Asp Ala Lys Lys Tyr Phe
    1055                1060                1065

Leu Asp Gln Ile Glu Val Cys Arg Asp Lys Gly Trp Thr Val Gln
    1070                1075                1080

Phe Asn Trp Phe Leu His Leu Val Leu Gly Ile Lys Gln Gly Glu
    1085                1090                1095

Lys His Ser Ala
    1100

<210> SEQ ID NO 6
<211> LENGTH: 1044
<212> TYPE: PRT
<213> ORGANISM: Homo sapiens
<220> FEATURE:
<221> NAME/KEY: MISC_FEATURE
<222> LOCATION: (39)..(46)
```

-continued

```
<223> OTHER INFORMATION: peptide identified by mass spectrometry
<220> FEATURE:
<221> NAME/KEY: MISC_FEATURE
<222> LOCATION: (88)..(100)
<223> OTHER INFORMATION: peptide identified by mass spectrometry
<220> FEATURE:
<221> NAME/KEY: MISC_FEATURE
<222> LOCATION: (111)..(140)
<223> OTHER INFORMATION: peptide identified by mass spectrometry
<220> FEATURE:
<221> NAME/KEY: MISC_FEATURE
<222> LOCATION: (143)..(153)
<223> OTHER INFORMATION: peptide identified by mass spectrometry
<220> FEATURE:
<221> NAME/KEY: MISC_FEATURE
<222> LOCATION: (189)..(195)
<223> OTHER INFORMATION: peptide identified by mass spectrometry
<220> FEATURE:
<221> NAME/KEY: MISC_FEATURE
<222> LOCATION: (211)..(222)
<223> OTHER INFORMATION: peptide identified by mass spectrometry
<220> FEATURE:
<221> NAME/KEY: MISC_FEATURE
<222> LOCATION: (230)..(246)
<223> OTHER INFORMATION: peptide identified by mass spectrometry
<220> FEATURE:
<221> NAME/KEY: MISC_FEATURE
<222> LOCATION: (287)..(332)
<223> OTHER INFORMATION: peptide identified by mass spectrometry
<220> FEATURE:
<221> NAME/KEY: MISC_FEATURE
<222> LOCATION: (341)..(386)
<223> OTHER INFORMATION: peptide identified by mass spectrometry
<220> FEATURE:
<221> NAME/KEY: MISC_FEATURE
<222> LOCATION: (390)..(400)
<223> OTHER INFORMATION: peptide identified by mass spectrometry
<220> FEATURE:
<221> NAME/KEY: MISC_FEATURE
<222> LOCATION: (438)..(490)
<223> OTHER INFORMATION: peptide identified by mass spectrometry
<220> FEATURE:
<221> NAME/KEY: MISC_FEATURE
<222> LOCATION: (534)..(548)
<223> OTHER INFORMATION: peptide identified by mass spectrometry
<220> FEATURE:
<221> NAME/KEY: MISC_FEATURE
<222> LOCATION: (621)..(631)
<223> OTHER INFORMATION: peptide identified by mass spectrometry
<220> FEATURE:
<221> NAME/KEY: MISC_FEATURE
<222> LOCATION: (643)..(673)
<223> OTHER INFORMATION: peptide identified by mass spectrometry
<220> FEATURE:
<221> NAME/KEY: MISC_FEATURE
<222> LOCATION: (685)..(691)
<223> OTHER INFORMATION: peptide identified by mass spectrometry
<220> FEATURE:
<221> NAME/KEY: MISC_FEATURE
<222> LOCATION: (694)..(700)
<223> OTHER INFORMATION: peptide identified by mass spectrometry
<220> FEATURE:
<221> NAME/KEY: MISC_FEATURE
<222> LOCATION: (706)..(720)
<223> OTHER INFORMATION: peptide identified by mass spectrometry
<220> FEATURE:
<221> NAME/KEY: MISC_FEATURE
<222> LOCATION: (803)..(870)
<223> OTHER INFORMATION: peptide identified by mass spectrometry
<220> FEATURE:
<221> NAME/KEY: MISC_FEATURE
<222> LOCATION: (895)..(920)
<223> OTHER INFORMATION: peptide identified by mass spectrometry
<220> FEATURE:
<221> NAME/KEY: MISC_FEATURE
<222> LOCATION: (928)..(955)
<223> OTHER INFORMATION: peptide identified by mass spectrometry
<220> FEATURE:
<221> NAME/KEY: MISC_FEATURE
<222> LOCATION: (983)..(1013)
```

```
<223> OTHER INFORMATION: peptide identified by mass spectrometry
<220> FEATURE:
<221> NAME/KEY: MISC_FEATURE
<222> LOCATION: (1017)..(1024)
<223> OTHER INFORMATION: peptide identified by mass spectrometry
<220> FEATURE:
<221> NAME/KEY: MISC_FEATURE
<222> LOCATION: (1031)..(1040)
<223> OTHER INFORMATION: peptide identified by mass spectrometry

<400> SEQUENCE: 6
```

Met Pro Pro Gly Val Asp Cys Pro Met Glu Phe Trp Thr Lys Glu Glu
1               5                   10                  15

Asn Gln Ser Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
            35                  40                  45

Leu Trp His Arg Ala Gln Tyr Glu Pro Leu Phe His Met Leu Ser Gly
        50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Val Pro Leu Ala Leu Met Ala Cys Ala Leu Arg Lys Lys
    210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
            260                 265                 270

His Leu Thr Met Val His Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Ser Val Cys Ser Glu
        355                 360                 365

-continued

```
Pro Val Trp Lys Gln Arg Leu Glu Phe Asp Ile Asn Ile Cys Asp Leu
    370                 375                 380
Pro Arg Met Ala Arg Leu Cys Phe Ala Leu Tyr Ala Val Ile Glu Lys
385                 390                 395                 400
Ala Lys Lys Ala Arg Ser Thr Lys Lys Ser Lys Lys Ala Asp Cys
                405                 410                 415
Pro Ile Ala Trp Ala Asn Leu Met Leu Phe Asp Tyr Lys Asp Gln Leu
            420                 425                 430
Lys Thr Gly Glu Arg Cys Leu Tyr Met Trp Pro Ser Val Pro Asp Glu
        435                 440                 445
Lys Gly Glu Leu Leu Asn Pro Thr Gly Thr Val Arg Ser Asn Pro Asn
    450                 455                 460
Thr Asp Ser Ala Ala Leu Leu Ile Cys Leu Pro Glu Val Ala Pro
465                 470                 475                 480
His Pro Val Tyr Tyr Pro Ala Leu Glu Lys Ile Leu Glu Leu Gly Arg
                485                 490                 495
His Ser Glu Cys Val His Val Thr Glu Glu Gln Leu Gln Leu Arg
            500                 505                 510
Glu Ile Leu Glu Arg Arg Gly Ser Gly Glu Leu Tyr Glu His Glu Lys
        515                 520                 525
Asp Leu Val Trp Lys Leu Arg His Glu Val Gln Glu His Phe Pro Glu
    530                 535                 540
Ala Leu Ala Arg Leu Leu Leu Val Thr Lys Trp Asn Lys His Glu Asp
545                 550                 555                 560
Val Ala Gln Met Leu Tyr Leu Leu Cys Ser Trp Pro Glu Leu Pro Val
                565                 570                 575
Leu Ser Ala Leu Glu Leu Leu Asp Phe Ser Phe Pro Asp Cys His Val
            580                 585                 590
Gly Ser Phe Ala Ile Lys Ser Leu Arg Lys Leu Thr Asp Asp Glu Leu
        595                 600                 605
Phe Gln Tyr Leu Leu Gln Leu Val Gln Val Leu Lys Tyr Glu Ser Tyr
    610                 615                 620
Leu Asp Cys Glu Leu Thr Lys Phe Leu Leu Asp Arg Ala Leu Ala Asn
625                 630                 635                 640
Arg Lys Ile Gly His Phe Leu Phe Trp His Leu Arg Ser Glu Met His
                645                 650                 655
Val Pro Ser Val Ala Leu Arg Phe Gly Leu Ile Leu Glu Ala Tyr Cys
            660                 665                 670
Arg Gly Ser Thr His His Met Lys Val Leu Met Lys Gln Gly Glu Ala
        675                 680                 685
Leu Ser Lys Leu Lys Ala Leu Asn Asp Phe Val Lys Leu Ser Ser Gln
    690                 695                 700
Lys Thr Pro Lys Pro Gln Thr Lys Glu Leu Met His Leu Cys Met Arg
705                 710                 715                 720
Gln Glu Ala Tyr Leu Glu Ala Leu Ser His Leu Gln Ser Pro Leu Asp
                725                 730                 735
Pro Ser Thr Leu Leu Ala Glu Val Cys Val Glu Gln Cys Thr Phe Met
            740                 745                 750
Asp Ser Lys Met Lys Pro Leu Trp Ile Met Tyr Ser Asn Glu Glu Ala
        755                 760                 765
Gly Ser Gly Gly Ser Val Gly Ile Ile Phe Lys Asn Gly Asp Asp Leu
    770                 775                 780
Arg Gln Asp Met Leu Thr Leu Gln Met Ile Gln Leu Met Asp Val Leu
```

-continued

```
              785              790              795              800
Trp Lys Gln Glu Gly Leu Asp Leu Arg Met Thr Pro Tyr Gly Cys Leu
                805              810              815
Pro Thr Gly Asp Arg Thr Gly Leu Ile Glu Val Val Leu Arg Ser Asp
                820              825              830
Thr Ile Ala Asn Ile Gln Leu Asn Lys Ser Asn Met Ala Ala Thr Ala
                835              840              845
Ala Phe Asn Lys Asp Ala Leu Leu Asn Trp Leu Lys Ser Lys Asn Pro
            850              855              860
Gly Glu Ala Leu Asp Arg Ala Ile Glu Glu Phe Thr Leu Ser Cys Ala
865              870              875              880
Gly Tyr Cys Val Ala Thr Tyr Val Leu Gly Ile Gly Asp Arg His Ser
                885              890              895
Asp Asn Ile Met Ile Arg Glu Ser Gly Gln Leu Phe His Ile Asp Phe
                900              905              910
Gly His Phe Leu Gly Asn Phe Lys Thr Lys Phe Gly Ile Asn Arg Glu
                915              920              925
Arg Val Pro Phe Ile Leu Thr Tyr Asp Phe Val His Val Ile Gln Gln
930              935              940
Gly Lys Thr Asn Asn Ser Glu Lys Phe Glu Arg Phe Arg Gly Tyr Cys
945              950              955              960
Glu Arg Ala Tyr Thr Ile Leu Arg Arg His Gly Leu Leu Phe Leu His
                965              970              975
Leu Phe Ala Leu Met Arg Ala Ala Gly Leu Pro Glu Leu Ser Cys Ser
                980              985              990
Lys Asp Ile Gln Tyr Leu Lys Asp  Ser Leu Ala Leu Gly  Lys Thr Glu
                995              1000             1005
Glu Glu  Ala Leu Lys His Phe  Arg Val Lys Phe Asn  Glu Ala Leu
    1010             1015             1020
Arg Glu  Ser Trp Lys Thr Lys  Val Asn Trp Leu Ala  His Asn Val
    1025             1030             1035
Ser Lys Asp Asn Arg Gln
    1040
```